(12) United States Patent
Penichet et al.

(10) Patent No.: US 12,595,310 B2
(45) Date of Patent: Apr. 7, 2026

(54) COMPOSITIONS AND METHODS FOR TRANSFERRIN RECEPTOR 1 TARGETING

(71) Applicant: THE REGENTS OF THE UNIVERSITY OF CALIFORNIA, Oakland, CA (US)

(72) Inventors: Manuel L. Penichet, Los Angeles, CA (US); Tracy R. Wells, Los Angeles, CA (US); Pierre V. Candelaria, Los Angeles, CA (US); Juan C. Almagro, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 957 days.

(21) Appl. No.: 17/775,167

(22) PCT Filed: Nov. 6, 2020

(86) PCT No.: PCT/US2020/059532
§ 371 (c)(1),
(2) Date: May 6, 2022

(87) PCT Pub. No.: WO2021/092482
PCT Pub. Date: May 14, 2021

(65) Prior Publication Data
US 2022/0411527 A1 Dec. 29, 2022

Related U.S. Application Data

(60) Provisional application No. 62/931,570, filed on Nov. 6, 2019.

(51) Int. Cl.
| | | |
|---|---|---|
| *C07K 16/28* | (2006.01) | |
| *A61K 39/395* | (2006.01) | |
| *A61K 45/06* | (2006.01) | |
| *A61P 35/00* | (2006.01) | |
| *A61K 39/00* | (2006.01) | |

(52) U.S. Cl.
CPC ...... *C07K 16/2881* (2013.01); *A61K 39/3955* (2013.01); *A61K 45/06* (2013.01); *A61P 35/00* (2018.01); *A61K 2039/505* (2013.01); *C07K 2317/24* (2013.01); *C07K 2317/94* (2013.01)

(58) Field of Classification Search
CPC .................... C07K 16/2881; A61K 2039/505; A61P 35/00
See application file for complete search history.

(56) References Cited

U.S. PATENT DOCUMENTS

| | | |
|---|---|---|
| 6,329,508 B1 | 12/2001 | Friden |
| 8,734,799 B2 | 5/2014 | Penichet et al. |
| 2019/0274291 A1 | 9/2019 | Dennis et al. |

FOREIGN PATENT DOCUMENTS

| | | | |
|---|---|---|---|
| WO | WO 1993/010819 | 6/1993 | |
| WO | WO-2008068048 A2 * | 6/2008 | .............. A61P 31/10 |
| WO | WO 2011/130164 | 10/2011 | |
| WO | WO 2014/189973 | 11/2014 | |
| WO | WO 2016/081643 | 5/2016 | |
| WO | WO 2016/207240 | 12/2016 | |
| WO | WO 2017/013230 | 1/2017 | |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*
Kussie et al. A single engineered amino acid substitution changes antibody fine specificity.J Immunol. Jan. 1, 1994;152(1):146-52. (Year: 1994).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
Almagro, J. et al., "Humanization of Antibodies", *J. Frontiers in Bioscience*, 1(13), 1619-1633, 2008.
Daniels et al., "An Antibody-based Multifaceted Approach Targeting the Human Transferrin Receptor for the Treatment of B-cell Malignancies", *J. Immunother.*, 34(6), 500-508, 2011.
Daniels-Wells et al., "Efficacy of an Anti-transferrin Receptor Antibody Against AIDS-related non-Hodgkin Lymphoma: A Brief Communication", *Journal Immunotherapy*, 38(8), 307-310, 2015.
Daniels-Wells et al., "Insights into the mechanism of cell death induced by saporin delivered into cancer cells by an antibody fusion protein targeting the transferrin receptor 1", *Toxicology In Vitro*, 27(1), 220-231, 2013.
Daniels-Wells et al., "Transferrin receptor 1: a target for antibody-mediated cancer therapy", *Immunotherapy*, 8(9), 991-994, 2016.
International Search Report for corresponding PCT Application No. PCT/US2020/059532, mailed Apr. 7, 2021.
Leoh, et al., "Gene delivery in malignant B cells using the combination of lentiviruses conjugated to anti-transferrin receptor antibodies and an immunoglobulin promoter" *Journal of Gene Medicine*, 16(1-2), 11-27, 2014.

(Continued)

*Primary Examiner* — Aurora M Fontainhas
*Assistant Examiner* — Jennifer A Benavides
(74) *Attorney, Agent, or Firm* — Norton Rose Fulbright US LLP

(57) ABSTRACT

Aspects of the disclosure relate to transferrin receptor 1 (TfR1)-binding proteins. In some cases, humanized TfR1-binding proteins are described. Embodiments include methods for treating one or more conditions, for example cancer, using a humanized TfR1-binding protein. In some embodiments, the disclosed methods and compositions involve one or more antibodies that are capable of binding TfR1. Certain aspects relate to humanized antibodies and antibody-like molecules comprising one or more amino acid substitutions (e.g., backmutations). Additional aspects relate to combination treatments with TfR1-binding proteins and one or more additional therapeutics.

20 Claims, 11 Drawing Sheets

Specification includes a Sequence Listing.

(56)     References Cited

OTHER PUBLICATIONS

Sun et al., "Blockade of a Laminin-411—Notch Axis with CRISPR/
Cas9 or a Nanobioconjugate Inhibits Glioblastoma Growth through
Tumor-Microenvironment Cross-talk", *Can. Res.*, 79(6), 1239-
1251, 2019.
Sade, H. et al., "A Human Blood-Brain Barrier Transcytosis Influ-
enced by pH-Dependent Receptor Binding", *PLOS ONE*, 9(4); p.
e96340, 2014.
Supplementary Search Report issued in corresponding European
Patent Application No. 201885635.1, dated Apr. 24, 2024.

* cited by examiner

Light Chain Variable Regions

| | FR1 | CDR1 | FR2 | CDR2 | FR3 | CDR3 | FR4 |
|---|---|---|---|---|---|---|---|
| ch128.1L | QIVLTQSPAIMSVSPGEKVTMTC | SASSSIRYIH | WYQQRPGTSPKRWIY | DTSNLASGVP | ARFSGSGSGTSYSLTISSMEAEDAATYYC | HQRNSYPWT | FGGGTRLEIR |
| L1(3-11*01/1) | EIVLTQSPATLSLSPGERATLSC | SASSSIRYIH | WYQQRPGQAPRLLIY | DTSNLASGVP | ARFSGSGSGTDFTLTISSLEPEDFAVYYC | HQRNSYPWT | FGQGTKVEIK |
| L2(3-11*01/1) | EIVLTQSPATLSVSPGERATLSC | SASSSIRYIH | WYQQRPGQAPRLLIY | DTSNLASGVP | ARFSGSGSGTDFTLTISSLEPEDFAVYYC | HQRNSYPWT | FGQGTKVEIK |
| L3(6-21*02/1) | EIVLTQSPDFQSVTPKEKVTITC | SASSSIRYIH | WYQQRPDQSPKLLIY | DTSNLASGVP | SRFSGSGSGTDFTLTINSLEAEDAATYYC | HQRNSYPWT | FGQGTKVEIK |
| L4(3-11*01/1) | EIVLTQSPATLSVSPGERATLSC | SASSSIRYIH | WYQQRPGQAPRLLIY | DTSNLASGVP | SRFSGSGSGTDFTLTISSLEPEDFAVYYC | HQRNSYPWT | FGQGTKVDIK |
| L5(3-11*01/1) | EIVLTQSPATLSLSPGERATLSC | SASSSIRYIH | WYQQRPGQAPRRWIY | DTSNLASGTP | ARFSGSGSGTDFTLTISSLEPEDFAVYYC | HQRNSYPWT | FGPGTKVDIK |
| L6(6-21*02/1) | EIVLTQSPDFQSVTPKEKVTITC | SASSSIRYIH | WYQQRPDQSPKRWIY | DTSNLASGTP | ARFSGSGSGTDFTLTINSLEAEDAATYYC | CQRNSYPWT | FGQGTKVEIK |
| L7(3-11*01/1) | EIVLTQSPATLSLSPGERATLSC | SASSSIRYIH | WYQQRPGQAPRRWIY | DTSNLASGTP | ARFSGSGSGTSYSLTISSLEPEDFAVYYC | HQRNSYPWT | FGQGTKVEIK |
| L8(6-21*02/1) | EIVLTQSPDFQSVTPKEKVTITC | SASSSIRYIH | WYQQRPDQSPKRWIY | DTSNLASGVP | SRFSGSGSGTSYSLTINSLEAEDAATYYC | HQRNSYPWT | FGQGTKVEIK |
| L9(3-11*01/1) | EIVLTQSPATLSLSPGERATLSC | SASSSIRYIH | WYQQRPGQAPRRWIY | DTSNLASGVP | SRFSGSGSGTSYSLTISSLEPEDFAVYYC | HQRNSYPWT | FGQGTKVEIK |
| L10(6-21*02/1) | EIVLTQSPDFQSVTPKEKVTITC | SASSSIRYIH | WYQQRPDQSPKRWIY | DTSNLASGVP | SRFSGSGSGTSYSLTINSLEAEDAATYYC | HQRNSYPWT | FGQGTKVEIK |
| L11(3-11*01/1) | EIVLTQSPATLSLSPGERATLSC | SASSSIRYIH | WYQQRPGQAPRLLIY | DTSNLASGVP | SRFSGSGSGTSYSLTISSLEPEDFAVYYC | HQRNSYPWT | FGQGTKVEIK |
| L12(6-21*02/1) | EIVLTQSPDFQSVTPKEKVTITC | SASSSIRYIH | WYQQRPDQSPKLLIY | DTSNLASGVP | SRFSGSGSGTSYSLTINSLEAEDAATYYC | HQRNSYPWT | FGQGTKVEIK |

Heavy Chain Variable Regions

| | FR1 | CDR1* | FR2 | CDR2 | FR3 | CDR3 | FR4 |
|---|---|---|---|---|---|---|---|
| ch128.1H | EVQLQQSGPELVKPGASMKISCKASGYSFTGYTMNWVKQSHGENLEWIGRINPHNGGTDYNQKFKDKAPLTVDKSSNTAYMELLSLTSGDSAVYYCARG | YYYSLLDYWGQGTSVTVSS |
| H1(1-2*05/4) | QVQLVQSGAEVKKPGASVKVSCKASGYSFTGYTMNWVRQAPGQGLEWMGRINPHNGGTDYNQKFKDRVTMTRDTSISTAYMELSRLRSDDTVVYYCARG | YYYSLLDYWGQGTLVTVSS |
| H2(1-2*05/4) | QVQLVQSGAEVKKPGASMKVSCKASGYSFTGYTMNWVRQAPGENLEWMGRINPHNGGTDYNQKFKDRVPMTRDTSINTAYMELSRLRSGDSVVYYCARG | YYYSLLDYWGQGTSVTVSS |
| H3(1-69*02/4) | QVQLVQSGAEVKKPGASMKVSCKASGYSFTGYTMNWVRQAPGENLEWMGRINPHNGGTDYNQKFKDRVPITADKSTNTAYMELSLRSGDSAVYYCARG | YYYSLLDYWGQGTLVTVSS |
| H4(3-30*01/4) | QVQLVESGGGVVQPGRSMRLSCAASGYSFTGYTMNWVRQAPGENLEWVARINPHNGGTDYNQKFKDRFPISRDNSKNTLYLQMNSLRAGDSAVYYCARG | YYYSLLDYWGQGTTVTVSS |
| H5(1-69*01/4) | QVQLVQSGAEVKKPGSSVKVSCKASGYSFTGYTMNWVRQAPGQGLEWMGRINPHNGGTDYAQKFQDRVITADESTSTAYMELSLRSEDTAVYYCARG | YYYSLLDYWGQGTLVTVSS |
| H6(5-51*01/4) | EVQLVQSGAEVKKPGESLKISCKGSGYSFTGYTMNWVRQMPGKGLEWMGRINPHNGGTDYNQKFKDQVTISADKSISTAYLQWSSLKASDTAMYCARG | YYYSLLDYWGQGTLVTVSS |
| H7(1-69*02/4) | QVQLVQSGAEVKKPGSSVKVSCKASGYSFTGYTMNWVRQAPGQGLEWMGRINPHNGGTDYNQKFKDRVITADKSTSTAYMELSSLRSEDTAVYYCARG | YYYSLLDYWGQGTLVTVSS |
| H8(3-30*01/4) | QVQLVESGGGVVQPGRSLRLSCAASGYSFTGYTMNWVRQAPGNGLEWVARINPHNGGTDYNQKFKDRFTISRDNSKNTLYLQMNSLRAEDTAVYYCARG | YYYSLLDYWGQGTTVTVSS |

Human germline genes used as FR donors are in parenthesis (IGV/IGJ)

CDRs (Kabat's definition)

CDR1* (Kabat's + Chothia's definitions)

Backmutations

Human mutations in the mouse CDRs

*Mutations based on structural analysis*

*FIG. 1*

| Antibody | Average Tm (°C) |
|----------|----------------|
| ch128.1 | 62.7 |
| H6L7 | 68.2 |
| H6L9 | 69.2 |
| H8L9 | 61.7 |
| H8L10 | 61.9 |

| Treatment Groups | Median Survival (Days) | p-value vs. isotype control | p-value vs. ch128.1 |
|---|---|---|---|
| Isotype control (n = 7) | 34 | - | |
| ch128.1 (n = 7) | Undefined | 0.0001 | - |
| H6L7 (n = 7) | Undefined | 0.0001 | 0.2775 |
| H6L9 (n = 7) | Undefined | 0.0001 | 0.7307 |
| H8L9 (n = 7) | Undefined | 0.0001 | 0.9683 |
| H8L10 (n = 7) | Undefined | 0.0001 | 0.6281 |

| Treatment Groups | Median Survival (Days) | p-value vs. buffer | p-value vs. isotype control | p-value vs. ch128.1 |
|---|---|---|---|---|
| Buffer (n = 8) | 33 | - | - | - |
| Isotype control (n = 8) | 33 | 0.5548 | - | - |
| ch128.1 (n = 8) | 44 | 0.0019 | 0.0027 | - |
| H6L7 (n = 9) | 57 | 0.0002 | 0.0004 | 0.6011 |
| H6L9 (n = 9) | 45 | 0.0005 | 0.0004 | 0.3106 |
| H8L9 (n = 9) | 55 | 0.0010 | 0.0015 | 0.5923 |
| H8L10 (n = 9) | 40 | 0.0108 | 0.0113 | 0.6512 |

| Treatment Groups | Median Survival (Days) | *p*-value vs. isotype control | *p*-value vs. ch128.1 |
|---|---|---|---|
| Isotype control (*n* = 9) | 35 | - | - |
| ch128.1 (*n* = 9) | 47 | 0.0001 | - |
| H6L7 (*n* = 9) | 47 | < 0.0001 | 0.4398 |

| Treatment Groups | Median Survival (Days) | p-value vs. buffer | p-value vs. isotype control |
|---|---|---|---|
| Buffer ($n = 9$) | 23 | - | - |
| Isotype control ($n = 10$) | 24 | 0.9024 | - |
| H6L7 ($n = 10$) | 42 | < 0.0001 | < 0.0001 |

| Treatment Groups | Median Survival (Days) | *p*-value vs. isotype control |
|---|---|---|
| Isotype control (*n* = 10) | 47 | - |
| H6L7 (*n* = 10) | 119 | 0.0064 |

COMPOSITIONS AND METHODS FOR TRANSFERRIN RECEPTOR 1 TARGETING

CROSS-REFERENCE TO RELATED APPLICATIONS

This application is a national phase application under 35 U.S.C. § 371 of International Application No PCT/US2020/059532, filed Nov. 6, 2020, which claims priority of U.S. Provisional Patent Application No. 62/931,570, filed Nov. 6, 2019, both of which are hereby incorporated by reference in their entirety.

This invention was made with government support under Grant Number CA196266 awarded by the National Institutes of Health. The government has certain rights in the invention.

BACKGROUND OF THE DISCLOSURE

Field of the Invention

This invention relates generally to the fields of molecular biology, immunology, immunotherapy, and medicine.

Background

Transferrin receptor 1 (TfR1), or CD71, is a cell surface protein responsible for facilitating iron uptake into cells via binding to iron-loaded transferrin. TfR1 expression is increased on a wide variety of cancer cells, including hematopoietic cancers. In some cases, such as in chronic lymphocytic leukemia (CLL) and non-Hodgkin lymphoma (NHL), its expression can be correlated with tumor stage or prognosis. Additionally, TfR1 is expressed on endothelial cells of the blood-brain barrier (BBB) and is used by certain viruses for cell entry See Daniels et al. *Clin. Immunol.*, 121(2):144-158 (2006); Daniels et al., *Biochim. Biophys. Acta.*, 1820(3):291-317 (2012); and Helguera et al., *J. Virol.*, 86(7):4024-4028 (2012).

Chimeric antibodies targeting TfR1 have been developed and demonstrate efficacy against malignancies and viral infections. Chimeric antibodies contain non-human variable regions, such as those from mice, combined with human constant regions to generate molecules with approximately 70% human content. Although chimeric antibodies have been shown to be more efficacious and less immunogenic in humans than murine antibodies, they often elicit a "human anti-chimeric antibody" (HACA) immune response because these antibodies retain approximately 30% non-human content. The HACA response may lead to the inactivation and elimination of the antibody, preventing its use for multiple administrations. In addition, this unwanted response may be associated with adverse reactions, ranging from mild to severe, which can further hamper the use of chimeric antibodies (Almagro et al., *Front. Immunol.* 8: Article 1751 (2018) and Scherer et al., *J. Dtsch. Dermatol. Ges.*, 8(6): 411-426 (2010)). Humanized antibodies, which on an average have more than 70% human content (e.g., 85% human content or more), are generally more desirable as a therapeutic in humans.

There remains a need for humanized antibodies targeting TfR1 with efficacy in treatment of TfR1-associated disorders (e.g., disorders in which TfR1 is overexpressed).

SUMMARY

The methods and compositions disclosed herein are based on generation of humanized antibodies targeting TfR1 that at least retain the binding affinity, while enhancing the developability profile of the engineered antibodies, when compared to the parental TfR1 antibody. In particular, disclosed herein are complementarity determining region (CDR)-grafted antibody variants with developable framework regions (FRs) as well as FR residues which are particularly relevant to retain TfR1 binding. These humanized antibodies (hu128.1) also retain the anti-tumor activity of the chimeric counterpart (ch128.1). Further, the disclosed humanized antibodies exhibit adequate monomericity (i.e., lack of high molecular weight aggregates), high solubility, and superior thermal stability as compared to ch128.1. Since it has been observed (Gilliland et al., *Methods Mol. Biol.*, 841:321-349 (2012)) that a high thermal stability leads to better expression, less aggregation and better long-term stability, it is expected that some of the hu128.1 antibodies disclosed herein will result in more developable therapeutic molecules than the parental chimeric antibody (ch128.1).

Embodiments of the present disclosure include, inter alia, antigen-binding proteins (e.g., antibodies, antibody-like molecules, or fragments thereof) comprising a heavy chain variable region and a light chain variable region having at least 80% identity with SEQ ID NO: 1. In some embodiments, the disclosed antigen-binding proteins, antibodies, antibody-like molecules, and fragments thereof are TfR1-binding proteins (i.e., are capable of binding to TfR1). In some embodiments, disclosed herein are humanized TfR1-binding proteins. Antigen-binding proteins described herein may be used in treating one or more conditions associated with expression or activity of a TfR1 protein such as, for example, cancer, autoimmune disorders, and certain viral infections. In addition, TfR1-binding proteins of the disclosure may be used to treat neurological conditions in which expression of TfR1 on the BBB may facilitate delivery of a therapeutic. Humanized TfR1-binding proteins may be used in treating one or more TfR1-associated conditions with reduced risk of toxicity and improved efficacy as compared to previously disclosed TfR1-binding proteins.

Embodiments include compositions comprising one or more antigen-binding proteins (e.g., TfR1-binding proteins). Embodiments include an antigen-binding protein comprising one or more regions (e.g., heavy chain variable region, light chain variable region, etc.). Embodiments include humanized antibodies or antibody-like molecules. Embodiments also include nucleic acid molecules encoding for one or more antigen-binding proteins or portions thereof. Embodiments include recombinant, transformed or modified cells, vectors, and/or expression cassettes comprising such nucleic acid molecules. In some embodiments, the compositions contemplated herein can comprise 1, 2, 3, 4, 5, or more of the following components: an antigen-binding protein, a nucleic acid, a vector, a cell, a polypeptide, an oligonucleotide, a light chain variable region, a heavy chain variable region, a complementarity determining region, a light chain constant region, and a heavy chain constant region. Any one or more of these components may be excluded from the disclosed compositions.

Embodiments also include methods of generating an antigen-binding protein, methods of producing an antigen-binding protein, methods of expressing an antigen-binding protein, methods of humanizing a chimeric antigen-binding protein, methods of detecting TfR1, methods of treating one or more conditions, methods of purifying TfR1, methods of treating cancer, methods of treating a neurological condition, methods of treating an autoimmune disease or condition, methods of treating an infection, such as a viral infection, and methods of eliminating one or more cells expressing TfR1. The steps and embodiments discussed in this disclosure are contemplated as part of any of these methods. In some embodiments, the methods contemplated herein can comprise or exclude 1, 2, 3, 4, 5, or more of the following steps: providing an antigen-binding protein, providing a nucleic acid to a cell, subjecting a cell to conditions sufficient to express a nucleic acid, providing an additional therapeutic, covalently attaching a therapeutic to an antigen-binding protein, non-covalently attaching a therapeutic to an antigen-binding protein, expressing a vector in a cell, and providing a pharmaceutical composition to a subject. Any one or more of these steps may be excluded from the disclosed methods.

In some embodiments, the antigen-binding protein has or lacks one or more post-translational modifications such as myristoylation, palmitoylation, isoprenylation or pre-nylation, farnesylation, geranylgeranylation, glypiation, acylation, acetylation, formylation, alkylation, methylation, amide bond formation, amidation at C-terminus, argin-ylation, polyglutamylation, polyglycylation, butyrylation, glycosylation, glycation, polysialylation, malonylation, hydroxylation, iodination, phosphorylation, adenylylation, propionylation, S-glutathionylation, S-nitrosylation, S-sulfenylation (aka S-sulphenylation), succinylation, sul-fation, biotinylation, PEGylation, SUMOylation, ubiquitina-tion, neddylation, pupylation, disulfide bridges, or racem-ization. In other embodiments, the antigen-binding protein has reduced or increased amounts of one or more post-translational modifications as compared to the same antigen-binding protein expressed in the cell that is native to the encoded gene. The reduction or increase may be by at least or at most 25, 50, 60, 70, 80, 90, 100, 150, 200, 250, 300, 350, 400, 450, 500% or more (or any range derivable therein).

In some aspects, the disclosure relates to a TfR1-binding protein comprising (a) a light chain variable region having at least 70% identity with SEQ ID NO: 1, wherein the light chain variable region comprises an amino acid substitution at position 45 or position 46 relative to SEQ ID NO: 1 and (b) a heavy chain variable region. In some embodiments, the light chain variable region has at least 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99%, or 100% sequence identity, or any range or value derivable therein, with SEQ ID NO: 1. In some embodiments, the amino acid substitution is at posi-tion 45 relative to SEQ ID NO: 1. In some embodiments, the light chain variable region comprises an arginine, a lysine, or a histidine at position 45 relative to SEQ ID NO: 1. In some embodiments, the light chain variable region com-prises an arginine at position 45 relative to SEQ ID NO: 1. In some embodiments, the amino acid substitution is at position 46 relative to SEQ ID NO: 1. In some embodiments, the light chain variable region comprises a tryptophan, a phenylalanine, a methionine, a valine, an isoleucine, a glycine, or an alanine at position 46 relative to SEQ ID NO: 1. In some embodiments, the light chain variable region comprises a tryptophan at position 46 relative to SEQ ID NO: 1. In some embodiments, the light chain variable region comprises an amino acid substitution at position 45 and position 46 relative to SEQ ID NO: 1. In some embodiments, the light chain variable region comprises (i) an arginine, a lysine, or a histidine at position 45 relative to SEQ ID NO: 1 and (ii) a tryptophan, a phenylalanine, a methionine, a valine, an isoleucine, a glycine, or an alanine at position 46 relative to SEQ ID NO: 1. In some embodiments, the light chain variable region comprises (i) an arginine at position 45 relative to SEQ ID NO: 1 and (ii) a tryptophan at position 46 relative to SEQ ID NO: 1. In some embodiments, the light chain variable region comprises SEQ ID NO: 5, SEQ ID NO: 6, SEQ ID NO: 7, SEQ ID NO: 8, SEQ ID NO: 9, or SEQ ID NO: 10.

Certain embodiments are directed to a TfR1-binding protein comprising (a) a light chain variable region com-prising, in order, (i) a first sequence having at least 50% identity with SEQ ID NO: 27, (ii) a second sequence having at least 80% identity with SEQ ID NO: 21, (iii) a third sequence having at least 50% identity with SEQ ID NO: 28, (iv) a fourth sequence having at least 80% identity with SEQ ID NO: 22, (v) a fifth sequence having at least 50% identity with SEQ ID NO: 29, (vi) a sixth sequence having at least 80% identity with SEQ ID NO: 23, and (vii) a seventh sequence having at least 50% identity with SEQ ID NO: 30, and (b) a heavy chain variable region.

In some embodiments, the third sequence comprises an amino acid substitution at position 12 or position 13 relative to SEQ ID NO: 28. In some embodiments, the amino acid substitution is at position 12 relative to SEQ ID NO: 28. In some embodiments, the third sequence comprises an argi-nine, a lysine, or a histidine at position 12 relative to SEQ ID NO: 28. In some embodiments, the third sequence comprises an arginine at position 12 relative to SEQ ID NO: 28. In some embodiments, the amino acid substitution is at position 13 relative to SEQ ID NO: 28. In some embodi-ments, the third sequence comprises a tryptophan, a phe-nylalanine, a methionine, a valine, an isoleucine, a glycine, or an alanine at position 13 relative to SEQ ID NO: 28. In some embodiments, the third sequence comprises a trypto-phan at position 13 relative to SEQ ID NO: 28. In some embodiments, the light chain variable region comprises an amino acid substitution at position 12 and position 13 relative to SEQ ID NO: 28. In some embodiments, the third sequence comprises (i) an arginine, a lysine, or a histidine at position 13 relative to SEQ ID NO: 28 and (ii) a tryptophan, a phenylalanine, a methionine, a valine, an isoleucine, a glycine, or an alanine at position 13 relative to SEQ ID NO: 28. In some embodiments, the third sequence comprises (i) an arginine at position 12 relative to SEQ ID NO: 28 and (ii) a tryptophan at position 13 relative to SEQ ID NO: 28. In some embodiments, the light chain variable region com-prises SEQ ID NO: 5, SEQ ID NO: 6, SEQ ID NO: 7, SEQ ID NO: 8, SEQ ID NO: 9, or SEQ ID NO: 10. In some embodiments, the first sequence comprises SEQ ID NO: 43, SEQ ID NO: 47, SEQ ID NO: 51, SEQ ID NO: 55, SEQ ID NO: 59, or SEQ ID NO: 63. In some embodiments, the third sequence comprises SEQ ID NO: 44, SEQ ID NO: 48, SEQ ID NO: 52, SEQ ID NO: 56, SEQ ID NO: 60, or SEQ ID NO: 64. In some embodiments, the fifth sequence comprises SEQ ID NO: 45, SEQ ID NO: 49, SEQ ID NO: 53, SEQ ID NO: 57, SEQ ID NO: 61, or SEQ ID NO: 65. In some embodiments, the seventh sequence comprises SEQ ID NO: 46, SEQ ID NO: 50, SEQ ID NO: 54, SEQ ID NO: 58, SEQ ID NO: 62, or SEQ ID NO: 66. In some embodiments, the second sequence comprises SEQ ID NO: 21. In some embodiments, the fourth sequence comprises SEQ ID NO: 22. In some embodiments, the sixth sequence comprises SEQ ID NO: 23 or SEQ ID NO: 109.

In some embodiments, the heavy chain variable region has at least 70% identity with SEQ ID NO: 13. In some embodiments, the heavy chain variable region has 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99% or 100% sequence identity, or any range or value derivable therein, with SEQ ID NO: 13. In some embodiments, the heavy chain variable region comprises SEQ ID NO: 13, SEQ ID NO: 17, SEQ ID NO: 18, SEQ ID NO: 19, or SEQ ID NO: 20. In some embodiments, the heavy chain variable region has at least 95% identity with SEQ ID NO: 13, SEQ ID NO: 17, SEQ ID NO: 18, SEQ ID NO: 19, or SEQ ID NO: 20 and the light chain variable region has at least 95% identity with SEQ ID NO: 5, SEQ ID NO: 6, SEQ ID NO: 7, SEQ ID NO: 8, SEQ ID NO: 9, or SEQ ID NO: 10. In some embodiments, the heavy chain variable region has at least 95% identity with SEQ ID NO: 18 and the light chain variable region has at least 95% identity with SEQ ID NO: 5, SEQ ID NO: 6, SEQ ID NO: 7, SEQ ID NO: 8, SEQ ID NO: 9, or SEQ ID NO: 10. In some embodiments, the heavy chain variable region has at least 95% identity with SEQ ID NO: 20 and the light chain variable region has at least 95% identity with SEQ ID NO: 5, SEQ ID NO: 6, SEQ ID NO: 7, SEQ ID NO: 8, SEQ ID NO: 9, or SEQ ID NO: 10. It is contemplated that any of the amino acid substitutions discussed herein, including, but not limited to the preceding paragraphs, can be implemented in the context of these percent identity limitations.

In some embodiments, the amino acid substitution is a nonconservative substitution. In some embodiments, the amino acid substitution is a conservative substitution. In some embodiments, the heavy chain variable region and the light chain variable region are on the same polypeptide. In some embodiments, the heavy chain variable region and the light chain variable region are on different polypeptides.

In some embodiments, the TfR1-binding protein has an affinity for TfR1 of between 0.001 and 1000 nM. In some embodiments, the TfR1-binding protein has a binding affinity for TfR1 of between 0.01 and 100 nM. In some embodiments, the TfR1-binding protein has a binding affinity for a TfR1 protein of between 0.1 and 20 nM. In some embodiments, the TfR1-binding protein has a binding affinity for a TfR1 protein of between 1 and 10 nM. In some embodiments, the TfR1-binding protein has a binding affinity for a TfR1 protein of at most, at least, or about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 20.5, 21, 21.5, 22, 22.5, 23, 23.5, 24, 24.5, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, or 1000 nM, or any range derivable therein.

In some embodiments, the TfR1-binding protein is an antibody, an antibody-like molecule, or a fragment thereof. In some embodiments, the TfR1-binding protein is an antibody, a nanobody, a minibody, a scFv fragment, or an Fab fragment.

Certain aspects are directed to a composition comprising a TfR1-binding protein, such as a TfR1-binding protein described herein, and an additional therapeutic. In some embodiments, the additional therapeutic is covalently attached to the TfR1-binding protein. In some embodiments, the additional therapeutic is non-covalently attached to the TfR1-binding protein. In some embodiments, the additional therapeutic is a chemotherapeutic drug, a nucleic acid (e.g., an antisense oligonucleotide, a small interfering RNA (siRNA), or a CRISPR-based gene therapy), a protein (e.g., a toxin or an enzyme), a viral vector, or a nanodrug.

Other embodiments are directed to a use of the composition comprising the TfR1-binding protein, which in some embodiments is linked to a therapeutic agent, in the manufacture of a medicament for the treatment or prevention of cancer, a neurological condition, an autoimmune or inflammatory disorder, or a viral infection. Certain embodiments are directed to use of the composition comprising the TfR1-binding protein in the manufacture of a medicament for the treatment or prevention of cancer.

Some embodiments are directed to a pharmaceutical composition comprising (i) a TfR1-binding protein, such as a TfR1-binding protein described herein, and (ii) a pharmaceutically acceptable excipient. Some embodiments are directed to a nucleic acid encoding for the TfR1-binding protein. Also disclosed is a vector comprising the nucleic acid. Certain aspects are directed to a cell comprising the TfR1-binding protein, the composition, the nucleic acid, and/or the vector. In some embodiments, the cell comprises the TfR1-binding protein and is capable of secreting the TfR1-binding protein outside the cell. In some embodiments, the cell is a B cell. In some embodiments, the cell is a hybridoma. In some embodiments, the cell comprises the TfR1-binding protein and the TfR1-binding protein is attached to a surface of the cell. In some embodiments, the TfR1-binding protein is a chimeric antigen receptor (CAR). In some embodiments, the cell is a T cell. In some embodiments, the cell is a natural killer (NK) cell. In some embodiments, the cell is a macrophage.

Some aspects are directed to a method for generating a TfR1-binding protein, such as a TfR1-binding protein described herein, comprising (a) providing to a cell a nucleic acid encoding for the TfR1-binding protein; and (b) subjecting the cell to conditions sufficient to express the TfR1-binding protein encoded by the nucleic acid in the cell.

A further embodiment is directed to a TfR1-binding protein prepared by a method described herein.

In some embodiments, provided herein is a method for treating cancer in a subject comprising providing to the subject a therapeutically effective amount of a TfR1-binding protein, such as a TfR1-binding protein described herein. In some embodiments, the method comprises eliminating malignant cells from the subject. In some embodiments, the method comprises eliminating pre-malignant cells from the subject. In some embodiments, the method comprises inhibiting proliferation of malignant cells in the subject. In some embodiments, provided herein is a method for treating a benign tumor in a subject comprising providing to the subject a therapeutically effective amount of a TfR1-binding protein, such as a TfR1-binding protein described herein. In some embodiments, provided herein is a method for treating a neurological condition in a subject comprising providing to the subject a therapeutically effective amount of the TfR1-binding protein. In some embodiments, the neurological condition is parkinsonism (e.g., primary parkinsonism or secondary parkinsonism). In some embodiments, the TfR1-binding protein is conjugated to one or more therapeutic agents capable of treating parkinsonism. In some embodiments, provided herein is a method for treating an autoimmune disorder in a subject comprising providing to the subject a therapeutically effective amount of the TfR1-binding protein. In some embodiments, provided herein is a method for treating a viral infection (e.g., an arenavirus infection) in a subject comprising providing to the subject a therapeutically effective amount of the TfR1-binding protein. In some embodiments, the method further comprises providing to the subject one or more additional therapeutics. In some embodiments, the one or more additional therapeutics are covalently attached to the TfR1-binding protein. In some embodiments, the one or more additional therapeutics are non-covalently attached to the TfR1-binding protein. In some embodiments, the one or more additional therapeutics comprise a chemotherapeutic drug, a nucleic acid (e.g., an antisense oligonucleotide, a siRNA, or a CRISPR-based gene therapy), a protein (e.g., a toxin or an enzyme), a viral vector, or a nanodrug.

Some embodiments are directed to a humanized antibody or antibody-like molecule comprising (a) a heavy chain variable region ($V_H$) comprising SEQ ID NO: 13, SEQ ID NO: 17, SEQ ID NO: 18, SEQ ID NO: 19, or SEQ ID NO: 20; and (b) a light chain variable region ($V_L$) comprising SEQ ID NO: 5, SEQ ID NO: 6, SEQ ID NO: 7, SEQ ID NO: 8, SEQ ID NO: 9, or SEQ ID NO: 10. In some embodiments, the heavy chain variable region comprises SEQ ID NO: 13. In some embodiments, the heavy chain variable region comprises SEQ ID NO: 17. In some embodiments, the heavy chain variable region comprises SEQ ID NO: 18. In some embodiments, the heavy chain variable region comprises SEQ ID NO: 19. In some embodiments, the heavy chain variable region comprises SEQ ID NO: 20. In some embodiments, the light chain variable region comprises SEQ ID NO: 5. In some embodiments, the light chain variable region comprises SEQ ID NO: 6. In some embodiments, the light chain variable region comprises SEQ ID NO: 7. In some embodiments, the light chain variable region comprises SEQ ID NO: 8. In some embodiments, the light chain variable region comprises SEQ ID NO: 9. In some embodiments, the light chain variable region comprises SEQ ID NO: 10.

Certain aspects relate to methods of treating a disorder comprising providing to a subject a TfR1-binding protein and an additional therapeutic.

It is contemplated that any method or composition described herein can be implemented with respect to any other method or composition described herein and that different embodiments may be combined.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Use of the one or more sequences or compositions may be employed based on any of the methods described herein. Other embodiments are discussed throughout this application. Any embodiment discussed with respect to one aspect of the disclosure applies to other aspects of the disclosure as well and vice versa. For example, any step in a method described herein can apply to any other method. Moreover, any method described herein may have an exclusion of any step or combination of steps. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows alignments (top) for the mouse $V_1$ region of 128.1 (ch128.1L) and humanized $V_L$ sequences (L1-L12), as well as alignments of the mouse $V_H$ region of 128.1 (ch128.1H) and humanized $V_H$ (H1-H8) sequences. The sequences provides in FIG. 1 are as follows: ch128.1L is SEQ ID NO: 107, L1 is SEQ ID NO: 1, L2 is SEQ ID NO: 2, L3 is SEQ ID NO: 3, L4 is SEQ ID NO: 4, L5 is SEQ ID NO: 5, L6 is SEQ ID NO: 6, L7 is SEQ ID NO: 7, L8 is SEQ ID NO: 8, L9 is SEQ ID NO: 9, L10 is SEQ ID NO: 10, L11 is SEQ ID NO: 11, L12 is SEQ ID NO: 12, ch128.1H is SEQ ID NO: 108, H1 is SEQ ID NO: 13, H2 is SEQ ID NO: 14, H3 is SEQ ID NO: 15, H4 is SEQ ID NO: 16, H5 is SEQ ID NO: 17, H6 is SEQ ID NO: 18, H7 is SEQ ID NO: 19, H8 is SEQ ID NO: 20.

FIG. 2A shows a derivative plot for each antibody in quadruplicate. FIG. 2B shows the estimated average Tm for each antibody calculated from the quadruplicate samples.

FIG. 3A shows binding of antibodies to human TfR1 obtained from the California Institute of Technology (CalTech, Pasadena, CA, USA). FIG. 3B shows binding of antibodies to cynomolgus monkey (Macaca fascicularis) TfR1 obtained from Sino Biological, Inc. (Bejing, China). FIG. 3C shows binding of antibodies to human TfR1 obtained from Kerafast, Inc. (Boston, MA, USA).

FIG. 4A shows binding of chimeric antibody ch128.1. FIG. 4B shows binding for antibody H6L7. FIG. 4C shows binding for antibody H6L9. FIG. 4D shows binding for antibody H8L9. FIG. 4E shows binding for antibody H8L10. Black histograms indicate cells incubated with each antibody and gray histograms indicate cells incubated with an isotype, negative control antibody.

DETAILED DESCRIPTION

Figures 2A, 2B:
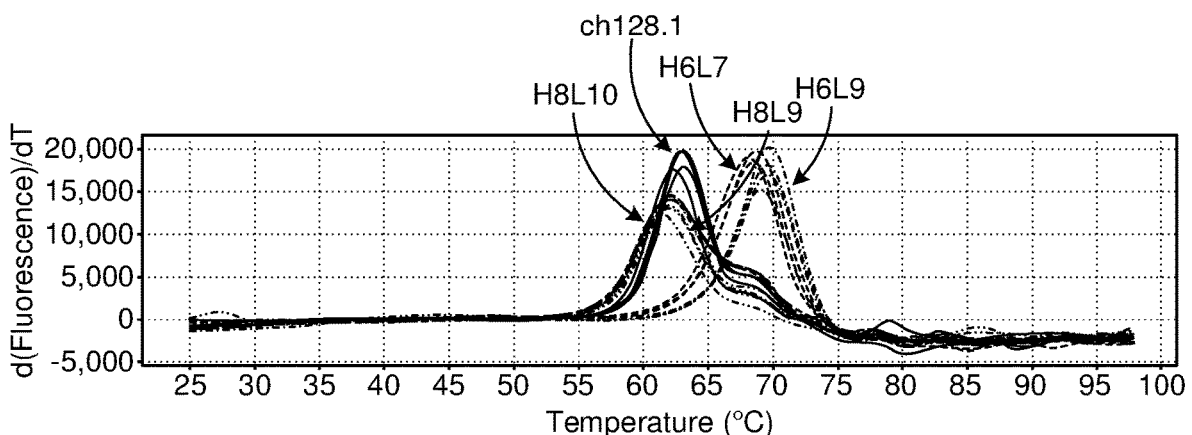
FIGS. 2A-2B shows the average melting temperature (Tm) for each of the antibodies H6L7, H6L9, H8L9, and H8L10 from the thermal stability analysis described in Example 3.
Figure 3A:
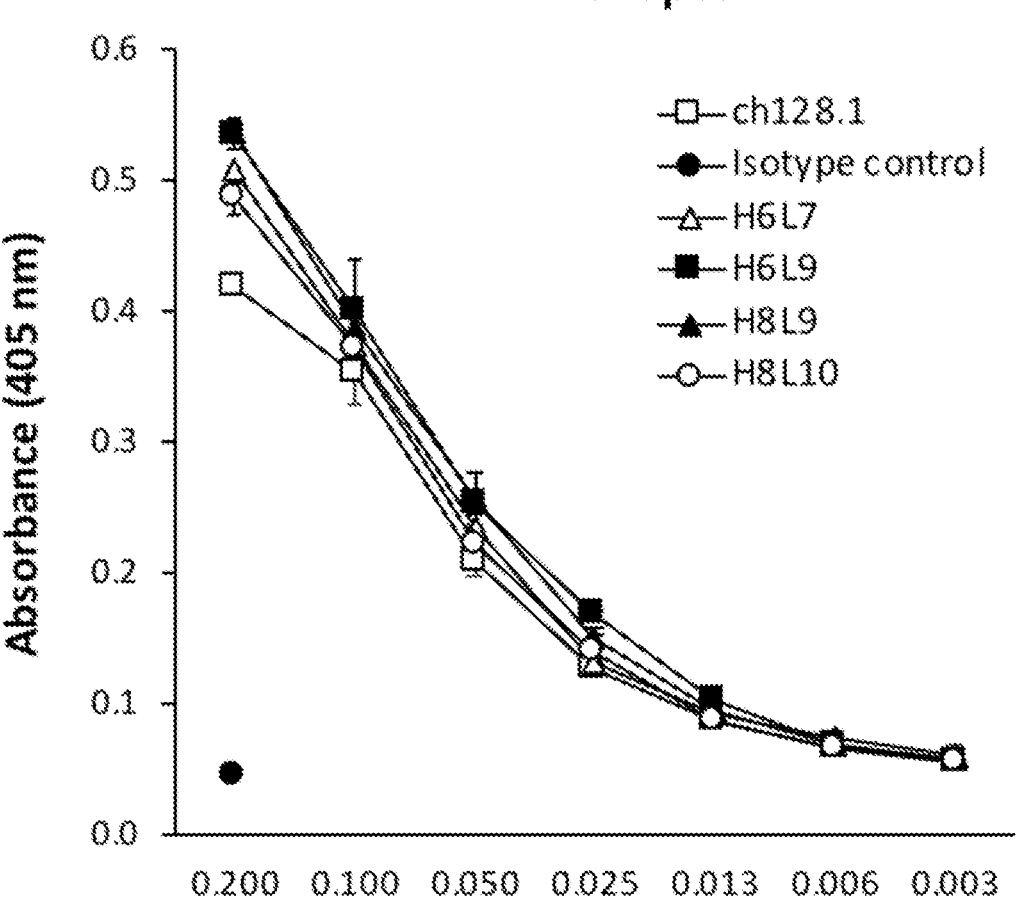
FIGS. 3A-3C show results from antigen-binding analysis of antibodies H6L7, H6L9, H8L9, and H8L10 using ELISA described in Example 4.
Figure 3B:
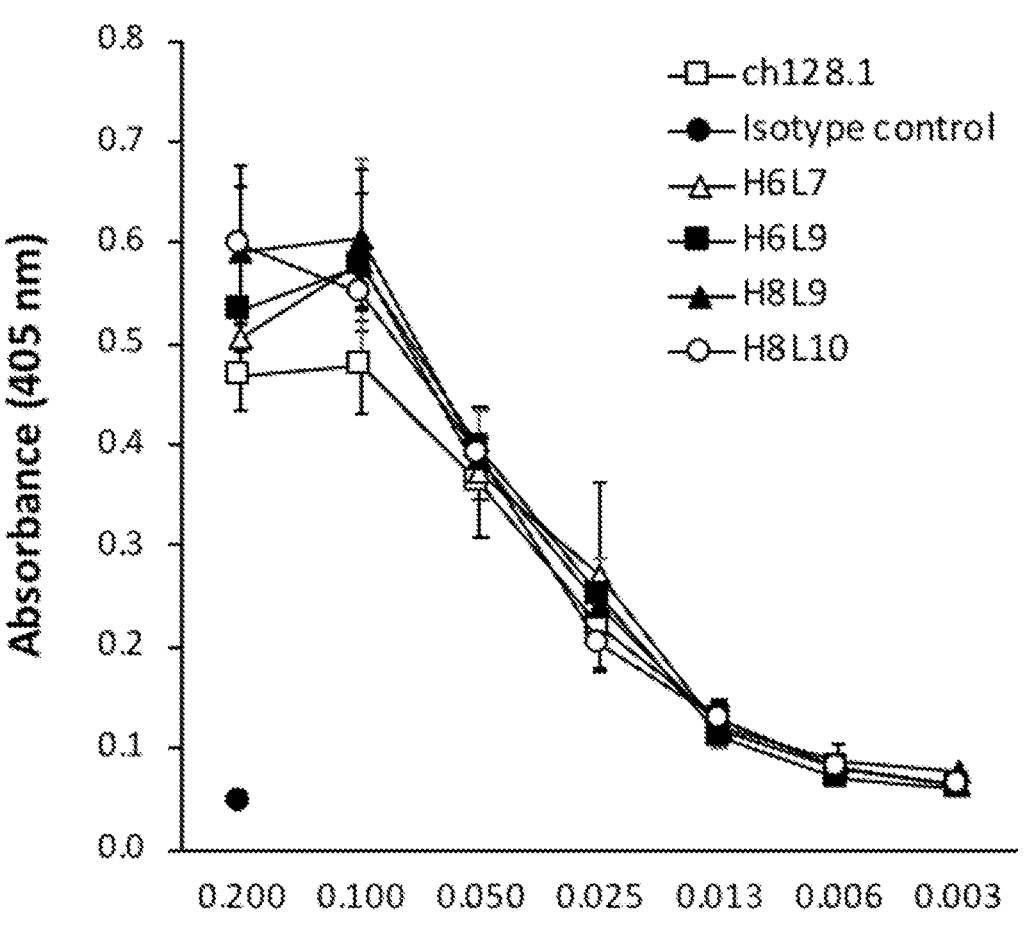
Figure 3C:
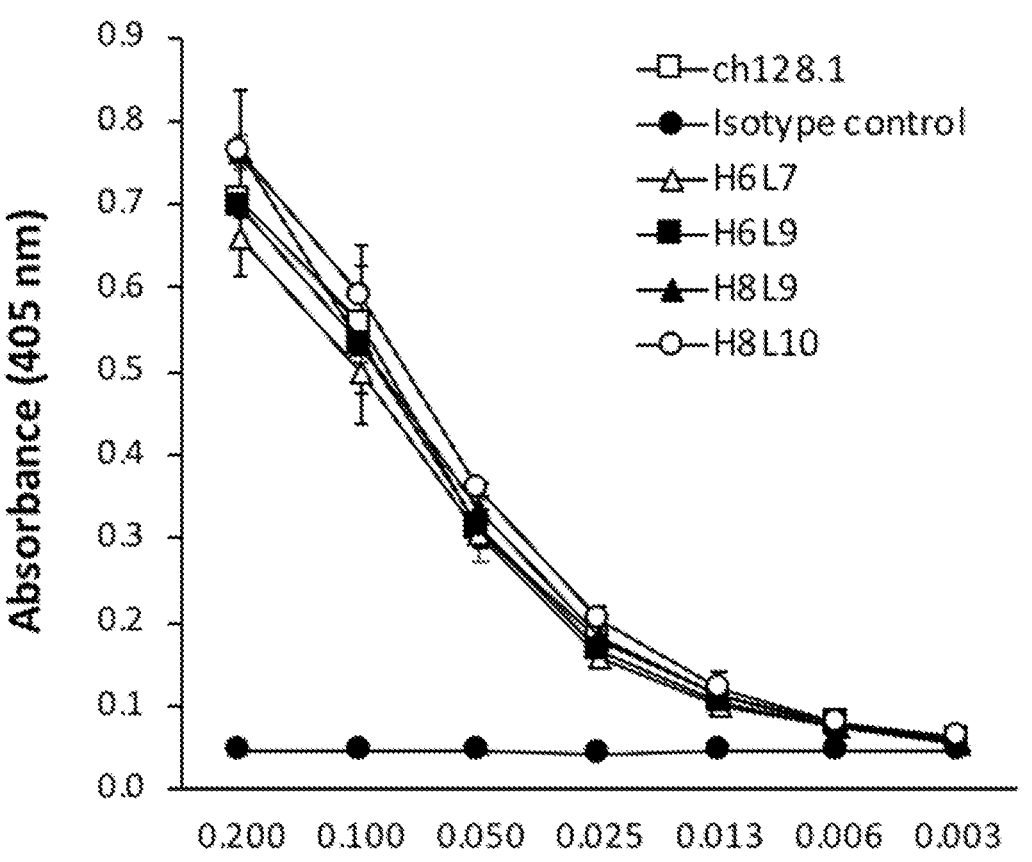
Figures 4A, 4B, 4C, 4D, 4E:
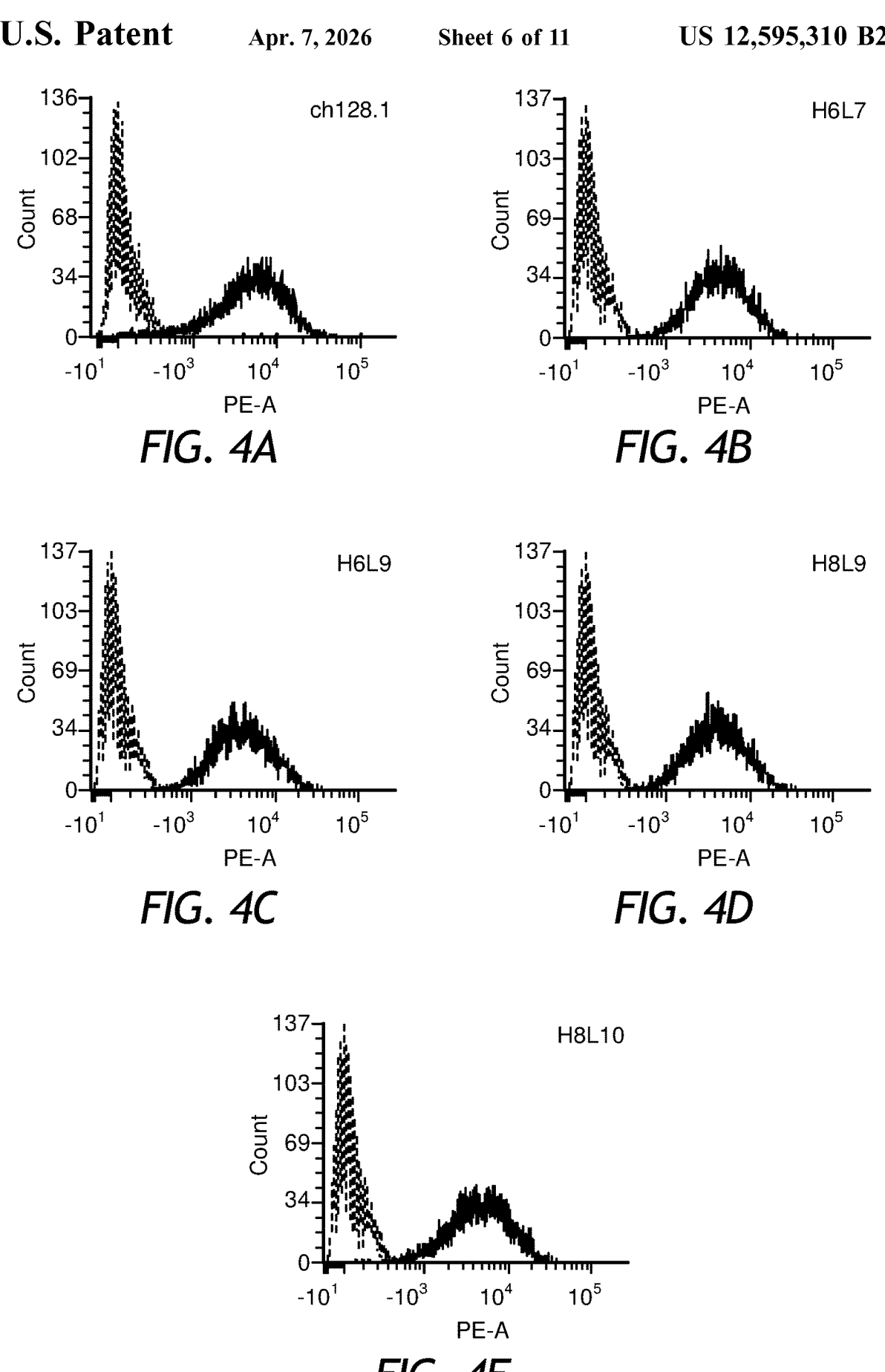
FIGS. 4A-4E show results from antigen-binding analysis of antibodies H6L7, H6L9, H8L9, and H8L10 using MM.1S cells and flow cytometry as described in Example 4.

Antibodies targeting TfR1 may provide various benefits in treating conditions such as cancer and viral infections. As described above, chimeric antibodies targeting TfR1 have been developed (see, e.g., Daniels et al., *J. Immunother.*, 34(6):500-8 (2012); Helguera et al., *J. Virol.*, 86(7):4024-8 (2012); and Leoh et al., *J. Immunol.*, 200(10):3485-3494 (2012)). Mouse/human chimeric IgG3/kappa and IgG1/kappa antibodies targeting human TfR1, also known as CD71, have been developed for therapeutic uses including, for example, as cancer therapies (see, e.g., Daniels-Wells et al., *Toxicol. In Vitro*, 27(1):220-31 (2013); Daniels-Wells et al., *J. Immunother.*, 38(8):307-10 (2015); Daniels-Wells et al., *Immunotherapy*, 8(9):991-4 (2016); Leoh et al., *J. Gene Med.*, 16(1-2):11-27 (2014); and Sun et al., *Can. Res.*, 79(6):1239-51 (2019)). These chimeric antibodies (ch128.1/IgG3 and ch128.1/IgG1) contain the variable regions of the murine monoclonal antibody 128.1 (Daniels et al., *J. Immunother.*, 34(6):500-8 (2011)).

It is known that chimeric antibodies are more efficacious and less immunogenic than mouse antibodies when used in human therapy (Almagro et al., *Front. Immunol.*, 8: Article 1751 (2018). However, chimeric antibodies still elicit "human anti-chimeric antibody" (HACA) responses (Hwang et al., *Methods*, 36(1):3-10 (2005)). Thus, to increase the human content of therapeutic antibodies and minimize an unwanted immunogenic response, several humanization methods have been developed in the last four decades (Almagro et al., *J. Front Biosci.*, 1(13):1619-33 (2008)). One of the most widely used methods is known in the art as CDR-grafting. This method was developed in the second half of the 1980s and comprises combining the CDRs from an antibody with the FRs of another antibody so that the specificity and affinity of CDRs donor antibody is transferred into the antibody proving the FRs. CDR grafting has successfully been applied to optimize as many as eight out of the 21 FDA-approved therapeutic antibodies to treat cancer (Almagro et al., *Front Immunol.*, 8: Article 1751 (2018)).

Humanization poses various challenges. First, it is not always possible to retain the binding profile of the parental chimeric antibody after the humanization process (Almagro et al., *J. Front. Biosci.*, 1(13):1619-33 (2008)). In such cases, amino acids from the mouse FR may be transferred into the human FRs. These mutations, known as backmutations, are carefully designed based, for example, on the three-dimensional structure—or computational models—of the mouse antibody. Other methods for designing backmutations have also been reported, such as looking at the conservation profile of amino acids in an alignment of related antibody sequences. In this case, if the amino acids in a certain position of the sequence alignment diverge from the humanized antibody, mutations similar to the ones seen in that position in the alignment of related antibody sequences can be engineered into the humanized molecule. Nevertheless, the impact of such mutations on the binding affinity is unpredictable and several variants must be designed and tested experimentally. Second, not all human FRs used to generate the humanized antibodies are developable (Gilliland et al., *Methods Mol. Biol.*, (841):321-349 (2012)). In other words, the humanized molecules in some instances cannot be formulated at the needed concentrations for therapeutic settings, do not express well in the manufacturing cells, tend to aggregate, and/or are not stable, leading to degradation products, which can be less effective and potentially toxic when used as therapeutic molecules.

As more antibodies have progressed from preclinical development to clinical trials, it has been realized that, in addition to affinity and in vitro activity, antibodies must be amenable to further development; a concept known in the art as developability (Almagro et al., *Front. Immunol.*, 8: Article 1751 (2018)). For instance, therapeutic antibodies should have good production yield in the cell lines intended for manufacturing, should be homogeneous (monomeric) preparations after purification, should be concentrated at meaningful therapeutic doses, and should be able to be produced as stable molecules to achieve the desired therapeutic effect. For instance, posttranslational amino acid modifications such as deamidation of asparagine, oxidation of methionine, isomerization of aspartic acid, and glycation can lead to heterogenicities in the drug and/or lack of potency if these amino acids are involved in the interaction with the target. Other amino acids such as tryptophan can induce aggregation and thus immunogenicity or lack of solubility at concentrations required for the therapeutic indication, thus impairing the further development of the product. Therefore, identification of these amino acids and removal when possible and or selection of molecules with the proper developability profile during the early discovery or optimization, e.g., humanization, are now part of antibody engineering processes intended to increase the success rate in preclinical and clinical development.

Chimeric antibodies targeting TfR1 for use in therapeutic methods (e.g., anti-cancer, anti-viral, etc.) have been developed. These chimeric antibodies possess human constant regions and non-human variable regions. However, there remains a need for further humanized antibodies targeting TfR1. Disclosed herein are humanized antibodies capable of targeting TfR1. In particular, FR residues important for antigen binding are described. Humanized antibodies of the present disclosure, and derivatives thereof (e.g., antibody fragments, antibody-like molecules, etc.), may be useful in the treatment of various conditions including, for example, cancer, neurological disorders, autoimmune disorders, and viral infections. In some embodiments, humanized antibodies of the present disclosure are useful in the treatment of cancer.

I. DEFINITIONS

"Individual, "subject," and "patient" are used interchangeably and can refer to a human or non-human.

The terms "lower," "lowered," "reduce," "reduced," "reduction," "decrease," "decreased," "inhibit," "inhibited," or "inhibition" are all used herein generally to mean a decrease by a statistically significant amount. However, for avoidance of doubt, "lower," "lowered," "reduce," "reduced," "reduction," "decrease," "decreased," "inhibit," "inhibited," or "inhibition" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e., absent level as compared to a reference sample), or any decrease between 10-100% as compared to a reference level.

The terms "increased," "increase," "enhanced," "enhance," "activated," or "activate" are all used herein to generally mean an increase by a statically significant amount; for the avoidance of any doubt, "increased," "increase," "enhanced," "enhance," "activated," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' end of the DNA/RNA corresponding to the (amino) terminus (N-terminus) of the protein and a translation stop codon at the 3' end of the DNA/RNA whose prior codon corresponds to the (carboxy) terminus (C-terminus). A gene can include, but is not limited to, cDNA from prokaryotic or eukaryotic mRNA, genomic DNA sequences from prokaryotic or eukaryotic DNA, and synthetic DNA sequences. A transcription termination sequence will be located 3' to the gene sequence.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention. With respect to pharmaceutical compositions, the term "consisting essentially of" includes the active ingredients recited, excludes any other active ingredients, but does not exclude any pharmaceutical excipients or other components that are not therapeutically active.

The term "consisting of" refers to compositions, methods, and respective components thereof as described herein, which are exclusive of any element not recited in that description of the embodiment.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive "or".

Throughout this application, the term "about" is used to indicate that a value includes the inherent variation of error for the measurement or quantitation method.

II. ANTIBODIES

Aspects of the disclosure relate to antibodies comprising a light chain variable region having at least 70% identity with SEQ ID NO:1 and/or a heavy chain variable region having at least 70% identity with SEQ ID NO:13. In some embodiments, a light chain variable region of the disclosure comprises an amino acid substitution at position 45 and/or position 46 relative to SEQ ID NO:1.

The term "antibody" refers to an intact immunoglobulin of any class or isotype, or a fragment thereof that can compete with the intact antibody for specific binding to the target antigen, and includes chimeric, humanized, and fully human antibodies. Also contemplated are antibodies having specificity for more than one antigen or target, including bispecific antibodies, trispecific antibodies, tetraspecific antibodies, and other multispecific antibodies. As used herein, the terms "antibody" or "immunoglobulin" are used interchangeably and refer to any of several classes of structurally related proteins that function as part of the immune response of an animal, including IgM, IgD, IgG, IgA, IgE, and related proteins, as well as polypeptides comprising antibody CDRs that retain antigen-binding activity.

The term "antigen" refers to a molecule or a portion of a molecule capable of being bound by a selective binding agent, such as an antibody. An antigen may possess one or more epitopes that are capable of interacting with different antibodies.

The term "epitope" includes any region or portion of molecule capable of binding to an immunoglobulin (antibody) or to a T-cell receptor. Epitope determinants may include chemically active surface groups such as amino acids, sugar side chains, phosphoryl or sulfonyl groups, and may have specific three-dimensional structural characteristics and/or specific charge characteristics. Generally, antibodies specific for a particular target antigen would recognize an epitope on the target antigen within a complex mixture.

The epitope regions of a given polypeptide can be identified using many different epitope mapping techniques well known in the art, including: x-ray crystallography, nuclear magnetic resonance spectroscopy, site-directed mutagenesis mapping, protein display arrays, and hydrogen-deuterium exchange see, e.g., Rockberg and Nilvebrant (Eds.), *Epitope Mapping Protocols*, Humana Press, New York, NY, USA (2018). Such techniques are known in the art and described in, e.g., U.S. Pat. No. 4,708,871; Geysen et al. *Proc. Natl. Acad. Sci., USA* 81:3998-4002 (1984); Geysen et al. *Proc. Natl. Acad. Sci., USA* 82:178-182 (1985); and Geysen et al. *Mol. Immunol.,* 23:709-715 (1986), each of which is incorporated by reference herein in their entirety. Additionally, antigenic regions of proteins can also be predicted and identified using standard antigenicity and hydropathy plots.

The term "immunogenic sequence" means a molecule that includes an amino acid sequence of at least one epitope such that the molecule is capable of stimulating the production of antibodies in an appropriate host. The term "immunogenic composition" means a composition that comprises at least one immunogenic molecule (e.g., an antigen).

An intact antibody is generally composed of two full-length heavy chains and two full-length light chains, but in some instances may include fewer chains, such as antibodies naturally occurring in camelids that may comprise only heavy chains. Antibodies as disclosed herein may be derived solely from a single source or may be "chimeric," that is, different portions of the antibody may be derived from two different species. For example, for chimeric antibodies, the variable regions may be derived from a rat or murine source, while the constant region is derived from a different animal source, such as a human. The antibodies or antigen-binding fragments may be produced in hybridomas, by recombinant DNA techniques, or by enzymatic or chemical cleavage of intact antibodies. Unless otherwise indicated, the term "antibody" includes derivatives, variants, fragments, and muteins thereof, examples of which are described below (Sela-Culang et al., *Front. Immunol.,* 4: Article 302 (2013)).

The term "light chain" may describe a full-length light chain or fragments thereof. A full-length light chain has a molecular weight of around 25,000 Daltons and includes a variable region domain (abbreviated herein as $V_L$), and a constant region domain (abbreviated herein as $C_L$). There are two classifications of light chains, identified as kappa (κ) and lambda (λ). The term "$V_L$ fragment" means a fragment of the light chain of a monoclonal antibody that includes all or part of the light chain variable region, including CDRs. The variable region domain of the light chain is at the amino-terminus of the polypeptide.

The term "heavy chain" may describe a full-length heavy chain or fragments thereof. For example, a full-length heavy chain for human IgG1 has a molecular weight of around 50,000 Daltons and includes a variable region domain (abbreviated herein as $V_H$), and three constant region domains (abbreviated herein as $C_H1$, $C_H2$, and $C_H3$). The term "$V_H$ fragment" means a fragment of the heavy chain of a monoclonal antibody that includes all or part of the heavy chain variable region, including CDRs. The number of heavy chain constant region domains will depend on the class. The class of an antibody can be IgM, IgD, IgG, IgA, or IgE and is defined by the heavy chains present of which there are five classifications: mu (μ), delta (δ), gamma (γ), alpha (α), or epsilon (ε) chains, respectively. Human IgG has several subclasses (isotypes), including, IgG1, IgG2, IgG3, and IgG4.

A. Types of Antibodies

Antibodies can be whole immunoglobulins of any class or isotype or classification, chimeric antibodies, or hybrid antibodies with specificity to two or more antigens. They may also be fragments (e.g., F(ab')2, Fab', Fab, Fv, and the like), including hybrid fragments. An immunoglobulin also includes natural, synthetic, or genetically engineered proteins that act like an antibody by binding to specific antigens to form a complex. The term antibody includes genetically engineered or otherwise modified forms of immunoglobulins.

The term "monomer" means an antibody containing only one immunoglobulin unit. Monomers are the basic functional units of antibodies. The term "dimer" means an antibody containing two immunoglobulin units attached to one another via constant domains of the antibody heavy chains (the Fc, or fragment crystallizable, region). The complex may be stabilized by a joining (J) chain protein. The term "multimer" means an antibody containing more than two immunoglobulin units attached to one another via constant domains of the antibody heavy chains (the Fc region). The complex may be stabilized by a joining (J) chain protein.

The term "bivalent antibody" means an antibody that comprises two antigen-binding sites. The two binding sites may have the same antigen specificities or they may be bi-specific, meaning the two antigen-binding sites have different antigen specificities.

Bispecific antibodies are a class of antibodies that have paratopes (i.e., antigen-binding sites) for two distinct epitopes. In some embodiments, bispecific antibodies can be biparatopic, wherein a bispecific antibody may specifically recognize a different epitope from the same antigen. In some embodiments, bispecific antibodies can be constructed from a pair of different single domain antibodies termed "nanobodies". Single domain antibodies may be sourced and modified from cartilaginous fish and camelids. Nanobodies can be joined together by a linker using techniques typical to a person skilled in the art; such methods for selection and joining of nanobodies are described in PCT Publication Nos. WO2015044386A1 and WO2010037838A2 and Bever et al., *Anal. Chem.,* 86:7875-7882 (2014), each of which are specifically incorporated herein by reference in their entirety.

Bispecific antibodies can be constructed as: a whole IgG, Fab'2, Fab'PEG, a diabody, or alternatively as a scFv. Diabodies and scFvs can be constructed without an Fc region, using only variable domains. Bispecific antibodies may be produced by a variety of methods including, but not limited to, fusion of hybridomas or linking of Fab' fragments. See, e.g., Songsivilai et al., *Clin. Exp. Immunol.,* 79:315-321 (1990); Kostelny et al., *J. Immunol.,* 148:1547-1553 (1992), each of which are specifically incorporated by reference in their entirety.

In certain aspects, the antigen-binding fragment may be multispecific or heterospecific by multimerizing with $V_H$ and $V_L$ region pairs that bind a different antigen. For example, the antibody may bind to, or interact with, (a) a cell surface antigen, (b) an Fc receptor on the surface of an effector cell, or (c) at least one other component. Accordingly, aspects may include, but are not limited to, bispecific, trispecific, tetraspecific, and other multispecific antibodies or antigen-binding fragments thereof that are directed to epitopes and to other targets, such as Fc receptors on effector cells.

In some embodiments, multispecific antibodies can be used and directly linked via a short flexible polypeptide chain, using routine methods known in the art. One such example is diabodies that are bivalent, bispecific antibodies in which the $V_H$ and $V_L$ domains are expressed on a single polypeptide chain, and utilize a linker that is too short to allow for pairing between domains on the same chain, thereby forcing the domains to pair with complementary domains of another chain creating two antigen-binding sites. The linker functionality is applicable for embodiments of triabodies, tetrabodies, and higher order antibody multimers. (see, e.g., Hollinger et al., *Proc. Natl. Acad. Sci., USA*, 90:6444-6448 (1993); Polijak et al., *Structure*, 2:1121-1123 (1994); and Todorovska et al., *J. Immunol. Methods*, 248: 47-66 (2001), each of which is incorporated herein by reference in their entirety).

The part of the Fv fragment of an antibody molecule that binds specifically to an epitope of the antigen is referred to herein as the "paratope." The paratope consists of the amino acid residues that contact the epitope of an antigen to facilitate antigen recognition. Each of the two Fv fragments of an antibody is composed of the two variable domains, $V_H$ and $V_L$, in dimerized configuration. The primary structure of each of the variable domains includes three hypervariable loops separated by, and flanked by, framework regions (FRs). The hypervariable loops are the regions of highest primary sequences variability among the antibody molecules from any mammal. The term hypervariable loop is sometimes used interchangeably with the term "complementarity determining region (CDR)." The length of the hypervariable loops (or CDRs) varies between antibody molecules. The consensus of FRs from different antiboides— typically from the same species—can be used by one skilled in the art to identify both the FRs and the hypervariable loops (or CDRs) which are interspersed among the FRs. The hypervariable loops are given identifying names which distinguish their position within the polypeptide, and on which domain they occur. CDRs in the $V_L$ domain are identified as L1 (also CDR-L1), L2 (also CDR-L2), and L3 (also CDR-L3), with L1 occurring at the most distal end with respect to the $C_L$ domain and L3 occurring closest to the $C_L$ domain. The CDRs may also be given the names CDR1, CDR2, and CDR3. The L3 (CDR3) is generally the region of highest variability in the $V_L$ domain among all antibody molecules produced by a given organism. The CDRs are regions of the polypeptide chain arranged linearly in the primary structure and separated from each other by FRs. The amino terminal (N-terminal) end of the $V_L$ chain is named FR1. The region identified as FR2 occurs between L1 and L2 hypervariable loops. FR3 occurs between L2 and L3 hypervariable loops, and the FR4 region is closest to the $C_L$ domain. This structure and nomenclature is repeated for the $V_H$ chain, which includes three CDRs identified as H1 (also CDR-H1), H2 (also CDR-H2), and H3 (also CDR-H3). The H3 (CDR-H3) is generally the region of highest variability in the antibody molecules produced by a given organism. The majority of amino acid residues in the variable domains, or Fv fragments ($V_H$ and $V_L$), are part of the FRs (approximately 85%).

Several methods have been developed and can be used by one skilled in the art to identify the amino acids that constitute each of these regions. This can be done using any of a number of multiple sequence alignment methods and algorithms, which identify the conserved amino acid residues that make up the FRs, therefore identifying the CDRs that may vary in length but are located between FRs. Three commonly used numberings have been developed for identification of the CDRs of antibodies: Kabat (as described in Wu and Kabat, *J. Exp. Med.*, 132(2): 211-250 (1970)); Chothia (as described in Chothia et al., *Nature*, 342(6252): 877-883 (1989)); and IMGT (as described in Lefranc et al., *Dev. Comp. Immunol.*, 27(1): 55-77 (2003)). These methods each include unique numbering systems for the identification of the amino acid residues that constitute the variable regions. In most antibody molecules, the amino acid residues that actually contact the epitope of the antigen occur in the CDRs, although in some cases, residues within the FRs contribute to antigen-binding. Depending on the type and size of the antigen, different CDR residues may contact the antigen. See Almagro, *J. Mol. Recognit.*, 17(2):132-43 (2004), incorporated herein by reference.

One skilled in the art can use any of several methods to determine the paratope of an antibody. These methods include:

1) Computational predictions of the tertiary structure of the antibody/epitope binding interactions based on the chemical nature of the amino acid sequence of the antibody variable region and composition of the epitope.

2) Hydrogen-deuterium exchange and mass spectroscopy.

3) Polypeptide fragmentation and peptide mapping approaches in which one generates multiple overlapping peptide fragments from the full length of the polypeptide and evaluates the binding affinity of these peptides for the epitope.

4) Antibody Phage Display Library analysis in which the antibody Fab fragment encoding genes of the mammal are expressed by bacteriophage in such a way as to be incorporated into the coat of the phage. This population of Fab expressing phage are then allowed to interact with the antigen which has been immobilized or may be expressed in by a different exogenous expression system. Non-binding Fab fragments are washed away, thereby leaving only the specific binding Fab fragments attached to the antigen. The binding Fab fragments can be readily isolated and the genes which encode them determined. This approach can also be used for smaller regions of the Fab fragment including Fv fragments or specific $V_H$ and $V_L$ domains as appropriate.

5) X-ray crystallography.

6) Alanine scanning mutagenesis.

In certain aspects, affinity matured antibodies are enhanced with one or more modifications in one or more CDRs thereof (and/or one or more FRs thereof) that result in an improvement in the affinity of the antibody for a target antigen as compared to a parent antibody that does not possess those alteration(s). Certain affinity matured antibodies will have nanomolar or picomolar affinities for the target antigen. Affinity matured antibodies are produced by procedures known in the art, e.g., Marks et al., *Biotechnology*, 10(7):779-783 (1992) describes affinity maturation by $V_H$ and $V_L$ domain shuffling, random mutagenesis of CDR and/or FRs employed in phage display is described by Rajpal et al., *Proc. Natl. Acad. Sci. USA*, 102(24): 8466-8471 (2005) and Thie et al., *Methods Mol Biol.*, 525:309-322 (2009) in conjugation with computation methods as demonstrated in Tiller et al., *Front. Immunol.*, 8:986 (2017), each of which references are incorporated herein by reference in their entirety.

Chimeric immunoglobulins are the products of fused genes derived from different species; "humanized" antibodies generally have the FRs from human immunoglobulins and one or more CDRs are from a non-human source (e.g., murine).

In some embodiments, minimizing the antibody polypeptide sequence from the non-human species optimizes chimeric antibody function and reduces immunogenicity. Specific amino acid residues of the non-human antibody are modified to be homologous to corresponding residues in a human antibody. One example is the "CDR-grafted" antibody, in which an antibody comprises one or more CDRs from a particular species or belonging to a specific antibody class or subclass, while the remainder of the antibody chain(s) is identical or homologous to a corresponding sequence in antibodies derived from another species or belonging to another antibody class or subclass. In some instances, corresponding non-human (e.g., murine) residues replace FR region residues of the human immunoglobulin. Replacement of human FR region residues with non-human FR region residues may serve to improve and/or restore antigen-binding. Furthermore, humanized antibodies may comprise residues that are not found in the recipient anti-body or in the donor antibody to further refine performance. The humanized antibody may also comprise at least a portion of an immunoglobulin constant region, typically that of a human immunoglobulin.

Intrabodies are intracellularly localized immunoglobulins that bind to intracellular antigens as opposed to secreted antibodies, which bind antigens in the extracellular space.

Polyclonal antibody preparations typically include differ-ent antibodies against different determinants (epitopes). In order to produce polyclonal antibodies, a host, such as a rabbit or goat, is immunized with the antigen or antigen fragment, generally with an adjuvant and, if necessary, coupled to a carrier. Antibodies to the antigen are subse-quently collected from the sera of the host. The polyclonal antibody can be affinity purified against the antigen render-ing it monospecific.

A monoclonal antibody or "mAb" refers to an antibody obtained from a population of homogeneous antibodies from an exclusive parental cell, e.g., the population is identical except for naturally occurring mutations that may be present in minor amounts. Each monoclonal antibody is directed against a single antigenic determinant (epitope).

Also contemplated herein, in some embodiments, are activatable antibodies and antigen-binding fragments thereof. As used herein, "activatable" antibodies describe antibodies having a reduced affinity for an antigen (e.g., by the presence of a masking moiety) and which may be activated under appropriate conditions (e.g., by removal of a masking moiety via enzymatic cleavage), thereby signifi-cantly increasing the affinity of the antibody for the antigen. One example of an activatable antibody is a pro-antibody (or "probody"), examples of which are described in U.S. Pat. No. 10,179,817 and Autio et al., *Clin. Cancer Res.*, 26(5): 984-989 (2020).

B. Functional Antibody Fragments and Antigen-Binding Fragments

1. Antigen-Binding Fragments

Certain aspects relate to antibody fragments, such as antibody fragments that bind to antigen. The term functional antibody fragment includes antigen-binding fragments of an antibody that retain the ability to specifically bind to an antigen. These fragments are constituted of various arrange-ments of the variable region heavy chain ($V_H$) and/or light chain ($V_L$); and in some embodiments, include constant region heavy chain 1 ($C_H1$) and light chain ($C_L$). In some embodiments, they lack the Fc region constituted of heavy chain 2 ($C_H2$) and 3 ($C_H3$) domains. Embodiments of antigen-binding fragments and the modifications thereof may include: (i) the Fab fragment type constituted with the $V_L$, $V_H$, $C_L$, and $C_H1$ domains; (ii) the Fd fragment type constituted with the $V_H$ and $C_H1$ domains; (iii) the Fv fragment type constituted with the $V_H$ and $V_L$ domains; (iv) the single domain fragment type, dAb, (Holt et al., *Trends Biotechnol.*, 21(11):484-490 (2003)) constituted with a single $V_H$ or $V_L$ domain; (v) isolated CDRs. Such terms are described, for example, in Harlow and Lane (Eds.), *Anti-bodies: A Laboratory Manual*, Cold Spring Harbor Labora-tory, New York, NY, USA (1988); *Molecular Biology and*

18

*Biotechnology: A Comprehensive Desk Reference*, Meyers (Ed.), Wiley-VCH Publisher, Inc., New York, NY, USA (1995); Huston et al., *Cell Biophys.*, 22(1-3):189-224 (1993); and Pluckthun et al., *Methods Enzymol.*, 178:497-515 (1989), each of which are incorporated by reference in their entirety.

Antigen-binding fragments also include fragments of an antibody that retain exactly, at least, or at most 1, 2, or 3 CDRs from a light chain variable region. Fusions of CDR-containing sequences to an Fc region (or a $C_H2$ or $C_H3$ region thereof) are included within the scope of this defini-tion including, for example, scFv fused, directly or indi-rectly, to an Fc region are included herein.

The term Fab fragment means a monovalent antigen-binding fragment of an antibody containing the variable ($V_L$ and $V_H$) and the constant ($C_L$ and $C_H1$) domains. The term Fab' fragment means a monovalent antigen-binding frag-ment of a monoclonal antibody that is larger than an Fab fragment. For example, an Fab' fragment includes the $V_L$, $V_H$, $C_L$, and $C_H1$ domains and all or part of the hinge region. The term F(ab')2 fragment means a bivalent antigen-binding fragment of a monoclonal antibody comprising two Fab' fragments linked by a disulfide bridge at the hinge region. An F(ab')2 fragment includes, for example, all or part of the two $V_H$ and $V_L$ domains and can further include all or part of the two $C_L$ and $C_H1$ domains.

The term Fd fragment means a fragment of the heavy chain of a monoclonal antibody, which includes all or part of the $V_H$, including the CDRs. An Fd fragment can further include $C_H1$ region sequences.

The term Fv fragment means a monovalent antigen-binding fragment of a monoclonal antibody, including all or part of the $V_L$ and $V_H$, and absent of the $C_L$ and $C_H1$ domains. The $V_L$ and $V_H$ include, for example, the CDRs. Single-chain antibodies (sFv or scFv) are Fv molecules in which the $V_L$ and $V_H$ regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorpo-rated by reference. The term (scFv)$_2$ means bivalent or bispecific sFv polypeptide chains that include oligomeriza-tion domains at their C-termini, separated from the sFv by a hinge region. The oligomerization domain comprises self-associating α-helices, e.g., leucine zippers, which can be further stabilized by additional disulfide bonds. (scFv)$_2$ fragments are also known as "miniantibodies" or "minibod-ies."

A single domain antibody is an antigen-binding fragment containing only a $V_H$ or the $V_L$ domain. In some instances, two or more $V_H$ regions are covalently joined with a peptide linker to create a bivalent domain antibody. The two $V_H$ regions of a bivalent domain antibody may target the same or different antigens.

2. Fragment Crystallizable (Fc) Region

An Fc region contains two heavy chain fragments com-prising the $C_H2$ and $C_H3$ domains of an antibody. The two heavy chain fragments are held together by two or more disulfide bonds and by hydrophobic interactions of the $C_H3$ domains. The term "Fc polypeptide" as used herein includes native and mutein forms of polypeptides derived from the Fc region of an antibody. Truncated forms of such polypeptides containing a hinge region that promotes dimerization are included.

3. Cell Surface Receptors

Antigen-binding proteins of the present disclosure may be expressed on the surface of a cell. In some embodiments, antigen-binding proteins are cell surface receptors comprising antigen-binding domains (e.g., TfR1-binding domains) disclosed herein. In some embodiments, described herein are cell surface receptors comprising a TfR1-binding domain and one or more additional components or domains. Examples of cell surface receptors of the present disclosure include CARs. A TfR1-specific cell surface receptor may comprise one or more of an antigen-binding domain, a signal peptide, an extracellular spacer, a transmembrane domain, a cytoplasmic region, and a linker. In some embodiments, a cell surface receptor of the present disclosure comprises an antigen-binding domain having at least 70%, at least 75%, at least 80%, at least 85%, at least 90%, at least 95%, or 100% sequence identity with one or more of SEQ ID NOs:1-110. Cells expressing a TfR1-specific cell surface receptor may be useful in treating one or more TfR1-associated conditions, or as a means to transport a therapeutic to a compartment or tissue to treat the disease, as described elsewhere herein.

C. Polypeptides with Antibody CDRs and Scaffolding Domains that Display the CDRs Antigen-binding peptide scaffolds, such as CDRs, are used to generate protein-binding molecules in accordance with the embodiments. Generally, a person skilled in the art can determine the type of protein scaffold on which to graft at least one of the CDRs. It is known that scaffolds, optimally, must meet a number of criteria such as: good phylogenetic conservation; known three-dimensional structure; small size; few or no post-transcriptional modifications; and/or be easy to produce, express, and purify. Skerra, *J. Mol. Recognit.,* 13(4):167-187 (2000).

The protein scaffolds can be sourced from, but not limited to: fibronectin type III FN3 domain (known as "monobodies"), fibronectin type III domain 10, lipocalin, anticalin, Z-domain of protein A of *Staphylococcus aureus*, thioredoxin A or proteins with a repeated motif such as the "ankyrin repeat", the "armadillo repeat", the "leucine-rich repeat", and the "tetratricopeptide repeat". Such proteins are described in US Patent Publication Nos. 2010/0285564, 2006/0058510, 2006/0088908, 2005/0106660, and PCT Publication No. WO2006/056464, each of which are specifically incorporated herein by reference in their entirety. Scaffolds derived from toxins from scorpions, insects, plants, mollusks, etc., and the protein inhibitors of neuronal nitric oxide synthase (PIN) may also be used.

D. Antibody Binding

The term "selective binding agent", "antigen-binding agent", or "antigen-binding protein" refers to a molecule that binds to an antigen. Non-limiting examples include antibodies, antigen-binding fragments, scFv, Fab, Fab', F(ab')2, single chain antibodies, peptides, peptide fragments, and proteins.

The term "binding" refers to a direct association between two molecules, due to, for example, covalent, electrostatic, hydrophobic, and ionic and/or hydrogen-bond interactions, including interactions such as salt bridges and water bridges. "Immunologically reactive" means that the selective binding agent or antibody of interest will bind with antigens present in a biological sample. The term "immune complex" refers the combination formed when an antibody or selective binding agent binds to an epitope on an antigen.

1. Affinity/Avidity

The term "affinity" refers the strength with which an antibody or selective binding agent binds an epitope. In antibody-binding reactions, this is expressed as the affinity constant (Ka or ka sometimes referred to as the association constant) for any given antibody or selective binding agent. Affinity is measured as a comparison of the binding strength of the antibody to its antigen relative to the binding strength of the antibody to an unrelated amino acid sequence. The terms "immunoreactive" and "preferentially binds" are used interchangeably herein with respect to antibodies and/or selective binding agent.

There are several experimental methods that can be used by one skilled in the art to evaluate the binding affinity of any given antibody or selective binding agent for its antigen. This is generally done by measuring the equilibrium dissociation constant ($K_D$ or Kd), using the equation $K_D$=koff/kon=[A][B]/[AB]. The term koff is the rate of dissociation between the antibody and antigen per unit time, and is related to the concentration of antibody and antigen present in solution in the unbound form at equilibrium. The term kon is the rate of antibody and antigen association per unit time, and is related to the concentration of the bound antigen-antibody complex at equilibrium. The units used for measuring the $K_D$ are mol/L (molarity, or M), or concentration. The Ka of an antibody is the inverse of the $K_D$, and is determined by the equation Ka=1/$K_D$. Examples of some experimental methods that can be used to determine the $K_D$ value are: enzyme-linked immunosorbent assays (ELISA), isothermal titration calorimetry (ITC), fluorescence anisotropy, surface plasmon resonance (SPR), and affinity capillary electrophoresis (ACE).

Antibodies deemed useful in certain embodiments may have an equilibrium dissociation constant of about, at least about or at most about $10^{-6}$ M, $10^{-7}$ M, $10^{-8}$ M, $10^{-9}$ M, $10^{-10}$ M, $10^{-11}$ M, $10^{-12}$ M, or any range derivable therein.

2. Epitope Specificity

The epitope of an antigen is the specific region of the antigen for which an antibody has binding affinity. In the case of protein or polypeptide antigens, the epitope is the specific residues (or specified amino acids or protein segment) that the antibody binds with high affinity. An antibody does not necessarily contact every residue within the protein. Nor does every single amino acid substitution or deletion within a protein necessarily affect binding affinity. For purposes of this specification and the accompanying claims, the terms "epitope" and "antigenic determinant" are used interchangeably to refer to the site on an antigen to which B- and/or T-cell receptors respond or recognize. Polypeptide epitopes can be formed from both contiguous amino acids and noncontiguous amino acids juxtaposed by tertiary folding of a polypeptide. In some embodiments, an epitope includes at least 3, for example 5-10 amino acids, in a unique spatial conformation.

Epitope specificity of an antibody can be determined in a variety of ways. One approach, for example, involves testing a collection of overlapping peptides of about 15 amino acids spanning the full sequence of the protein and differing in increments of a small number of amino acids (e.g., 3 to 30 amino acids). The peptides are immobilized in separate wells of a microtiter dish. Immobilization can be accomplished, for example, by biotinylating one terminus of the peptides. This process may affect the antibody affinity for the epitope, therefore different samples of the same peptide can be biotinylated at the N- and C-terminus and immobilized in separate wells for the purposes of comparison. This is useful for identifying end-specific antibodies. Optionally, additional peptides can be included terminating at a particular amino acid of interest. This approach is useful for identifying end-specific antibodies to internal fragments. An antibody or antigen-binding fragment is screened for binding to each of the various peptides. The epitope is defined as a segment of amino acids that is common to all peptides to which the antibody shows high affinity binding.

3. Modification of Antigen-Binding Domains

It is understood that the antibodies of the present disclosure may be modified, such that they are substantially identical to the antibody polypeptide sequences, or fragments thereof, and still bind the epitopes of the present disclosure. Polypeptide sequences are "substantially identical" when optimally aligned using such programs as Clustal Omega, IGBLAST, GAP, or BESTFIT using default gap weights, they share at least 80% sequence identity, at least 90% sequence identity, at least 95% sequence identity, at least 96% sequence identity, at least 97% sequence identity, at least 98% sequence identity, or at least 99% sequence identity or any range therein.

As discussed herein, minor variations in the amino acid sequences of antibodies or antigen-binding regions thereof are contemplated as being encompassed by the present disclosure, providing that the variations in the amino acid sequence maintain at least 75%, more preferably at least 80%, at least 90%, at least 95%, at least 96%, at least 97%, at least 98%, and most preferably at least 99% sequence identity. In some embodiments, conservative amino acid replacements are contemplated.

Conservative replacements (also "conservative substitutions" or "conservative amino acid substitutions") are those that take place within a family of amino acids that possess similar biochemical properties, including charge, hydrophobicity, and size. Genetically encoded amino acids are generally divided into families based on the chemical nature of the side chain; e.g., acidic (aspartate, glutamate), basic (lysine, arginine, histidine), nonpolar (alanine, valine, leucine, isoleucine, proline, phenylalanine, methionine, tryptophan), and uncharged polar (glycine, asparagine, glutamine, cysteine, serine, threonine, tyrosine). Thus, a conservative replacement may comprise replacement of an amino acid in one family for an amino acid in the same family (e.g., replacement of a lysine with an arginine, replacement of an aspartate for a glutamate, etc.). Alternatively or in addition, amino acid similarity may be determined using a Blocks Substitution Matrix (BLOSUM), such as BLOSUM62 (Henikoff and Henikoff, *Proc. Natl. Acad. Sci.* USA, 89(22): 10915-9 (1992)). In this case, a conservative replacement may be a substitution of amino acids having a non-negative value on a BLOSUM62 matrix. Whether an amino acid change results in a functional peptide can readily be determined by assaying the specific activity of the polypeptide derivative. Standard ELISA, SPR, or other antibody-binding assays can be performed by one skilled in the art to make a quantitative comparison of antigen binging affinity between the unmodified antibody and any polypeptide derivatives with conservative substitutions generated through any of several methods available to one skilled in the art.

Fragments or analogs of antibodies or immunoglobulin molecules can be readily prepared by those skilled in the art. Certain preferred N- and C-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Standard methods to identify protein sequences that fold into a known three-dimensional structure are available to those skilled in the art; Dill and McCallum, *Science,* 338:1042-1046 (2012). Several algorithms for predicting protein structures and the gene sequences that encode these have been developed, and many of these algorithms can be found at the National Center for Biotechnology Information (on the World Wide Web at ncbi.nlm.nih.gov/guide/proteins/) and at the Bioinformatics Resource Portal (on the World Wide Web at expasy.org/proteomics). Thus, the foregoing examples demonstrate that those of skill in the art can recognize sequence motifs and structural conformations that may be used to define structural and functional domains in accordance with the invention.

It is also contemplated that the antigen-binding domain may be multispecific or multivalent by multimerizing the antigen-binding domain with $V_H$ and $V_L$ region pairs that bind either the same antigen (multi-valent) or a different antigen (multi-specific).

E. Enzymatic or Chemical Modification of Antibodies

In some aspects, also contemplated are glycosylation variants of antibodies, wherein the number and/or type of glycosylation sites have been altered compared to the amino acid sequences of the parent polypeptide. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861, incorporated herein by reference). In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked glycosylation sites are created.

Additional antibody variants include cysteine variants, wherein one or more cysteine residues in the parent or native amino acid sequence are deleted from or substituted with another amino acid (e.g., serine). Cysteine variants are useful, inter alia, when antibodies must be refolded into a biologically active conformation. Cysteine variants may have fewer cysteine residues than the native antibody and typically have an even number to minimize interactions resulting from unpaired cysteines.

In some aspects, the polypeptides can be PEGgylated to increase the biological half-life by reacting the polypeptide with polyethylene glycol (PEG) or a reactive ester or aldehyde derivative of PEG, under conditions in which one or more PEG groups become attached to the polypeptide. Polypeptide PEGylation may be carried out by an acylation reaction or an alkylation reaction with a reactive PEG molecule (or an analogous reactive water-soluble polymer). Methods for PEGylating proteins are known in the art and can be applied to the polypeptides of the disclosure to obtain PEGylated derivatives of antibodies. See, e.g., EP 0154316 and EP 0401384, incorporated herein by reference. In some aspects, the antibody is conjugated or otherwise linked to transthyretin (TTR) or a TTR variant. The TTR or TTR variant can be chemically modified with, for example, a chemical selected from the group consisting of dextran, poly(n-vinylpyrrolidone), polyethylene glycols, propropylene glycol homopolymers, polypropylene oxide/ethylene oxide co-polymers, polyoxyethylated polyols, and polyvinyl alcohols. As used herein, the term "polyethylene glycol" is intended to encompass any of the forms of PEG that have been used to derivatize other proteins.

1. Conjugation

Derivatives of the antibodies and antigen-binding fragments that are described herein are also provided. The derivatized antibody or fragment thereof may comprise any molecule or substance that imparts a desired property to the antibody or fragment. The derivatized antibody can comprise, for example, a detectable (or labeling) moiety (e.g., a radioactive, colorimetric, antigenic, or enzymatic molecule, or a detectable bead), a molecule that binds to another molecule (e.g., biotin/streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). In some embodiments, an antibody or fragment thereof is covalently attached to a molecule or substance, such as a labeling moiety or a therapeutic moiety. In some embodiments, an antibody or fragment thereof is non-covalently attached to a molecule or substance, such as a labeling moiety or a therapeutic moiety.

Optionally, an antibody or an antigen-binding fragment can be chemically conjugated to, or expressed as, a fusion protein with other proteins. In some aspects, polypeptides may be chemically modified by conjugating or fusing the polypeptide to serum protein, such as human serum albumin, to increase the half-life of the resulting molecule. See, e.g., EP 0322094 and EP 0486525. In some aspects, the polypeptides may be conjugated to a diagnostic agent and used diagnostically, for example, to monitor the development or progression of a disease and determine the efficacy of a given treatment regimen. In some aspects, the polypeptides may also be conjugated to a therapeutic agent to provide a therapy in combination with the therapeutic effect of the polypeptide. Additional suitable conjugated moleculars are a chemotherapeutic drug, a nucleic acid (e.g. an antisense oligonucleotide, a siRNA or a CRISPR-based gene therapy, etc.), a protein (e.g. a toxin, an enzyme, etc.), a viral vector, or a nanodrug. The functional nucleic acid molecules may act as effectors, inhibitors, modulators, and stimulators of a specific activity possessed by a target molecule, or the functional nucleic acid molecules may possess a de novo activity independent of any other molecules.

In some aspects, disclosed are antibodies and antibody-like molecules that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules include toxins, therapeutic enzymes, antibiotics, radiolabeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles, or ligands.

a. Conjugate Types

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to be detected, and/or further quantified if desired. Examples of detectable labels include, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., avidin and streptavidin) and the like. Particular examples of labels are, but not limited to, fluorescein, fluorescein isothiocyanate (FITC), rhodamine, dansyl, umbelliferone, dimethyl acridinium ester (DMAE), Texas red, phycoerythrin (PE), and luminol. Antibody conjugates include those intended primarily for use in vitro, where the antibody is linked to a secondary binding ligand and/or to an enzyme to generate a colored product upon contact with a chromogenic substrate. Examples of suitable enzymes include, but are not limited to, urease, alkaline phosphatase (AP), horseradish peroxidase (HRP), α- or ß-galactosidase, or glucose oxidase. Preferred secondary binding ligands are avidin and streptavidin compounds that are capable of binding biotin with high affinity. The uses of such labels is well known to those of skill in the art and are described, for example, in U.S. Pat. Nos. 3,817,837; 3,850,752; 3,939,350; 3,996,345; 4,277,437; 4,275,149; and 4,366,241, each incorporated herein by reference. Molecules containing azido groups may also be used to form covalent bonds to proteins through reactive nitrene intermediates that are generated by low intensity ultraviolet light.

In some aspects, contemplated are immunoconjugates comprising an antibody or antigen-binding fragment thereof conjugated (e.g., covalently attached) to a cytotoxic agent such as a chemotherapeutic agent, a drug, a nucleic acid (e.g., antisense oligonucleotide, siRNA, shRNA, etc.) a growth inhibitory agent, a toxin (e.g., an enzymatically active toxin of bacterial, fungal, plant, or animal origin, or fragments thereof), or a radioactive isotope (i.e., a radio-conjugate). In this way, the agent of interest can be targeted directly to cells bearing the targeted cell surface antigen. The antibody and the agent may be associated through non-covalent interactions such as through electrostatic forces, or by covalent bonds. Various linkers, known in the art, can be employed in order to form the immunoconjugate. Additionally, the immunoconjugate can be provided in the form of a genetic fusion protein. In one aspect, an antibody may be conjugated to various therapeutic substances in order to target the cell surface antigen. Examples of conjugated agents include, but are not limited to, metal chelate complexes, drugs, toxins and other effector molecules, such as cytokines, lymphokines, chemokines, immunomodulators, radiosensitizers, asparaginase, carboranes, and radioactive halogens.

In antibody drug conjugates (ADCs), an antibody is conjugated to one or more drug moieties (e.g., small molecule drugs such as chemotherapeutics) through a linker. The ADCs may be prepared by several routes, employing organic chemistry reactions, conditions, and reagents known to those skilled in the art, including: (1) reaction of a nucleophilic group of an antibody with a bivalent linker reagent, to form antibody-L, via a covalent bond, followed by reaction with a drug moiety D; and (2) reaction of a nucleophilic group of a drug moiety with a bivalent linker reagent, to form drug-linker (D-L), via a covalent bond, followed by reaction with the nucleophilic group of an antibody. ADCs may also be produced by modification of the antibody to introduce electrophilic moieties, which can react with nucleophilic substituents on the linker reagent or drug. Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In certain aspects, ADCs include covalent or aggregative conjugates of antibodies, or antigen-binding fragments thereof, with other proteins or peptides, such as by expression of recombinant fusion proteins comprising heterologous polypeptides fused to the N-terminus or C-terminus of an antibody polypeptide. For example, the conjugated peptide may be a heterologous signal (or leader) polypeptide, e.g., the yeast alpha-factor leader, or a peptide such as an epitope tag (e.g., V5-His). Antibody-containing fusion proteins may comprise peptides added to facilitate purification or identification of the antibody (e.g., poly-His). An antibody polypeptide also can be linked to the FLAG® (Sigma-Aldrich, St. Louis, MO, USA) peptide as described in Hopp et al., *Bio/Technology*, 6:1204-1210 (1988) and U.S. Pat. No. 5,011,912.

Also contemplated herein are activatable immunoconjugates comprising an antibody or antigen binding fragment thereof conjugated to a therapeutic agent, and further comprising a masking moiety, wherein the masking moiety reduces the ability of the antibody or antigen-binding fragment thereof to bind to an antigen (e.g., TfR1). A masking moiety may be conjugated to an antigen-binding protein of the disclosure via a linker having a protease cleavage site, where the masking moiety is removed via protease activity in a tumor microenvironment, thereby activating the antigen-binding protein. Certain non-limiting examples of activatable antibodies, antibody fragments, and immunoconjugates (e.g., ADCs) are described in U.S. Pat. No. 10,179,817, incorporated herein by reference. In some embodiments, disclosed is an activatable anti-TfR1 antibody or antigen-binding fragment thereof.

b. Conjugation Methodology

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates may also be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate dihydrochloride), active esters (such as disuccinimidyl suberate), aldehydes (such as glutaraldehyde), bis-azido compounds (such as bis(p-azidobenzoyl) hexanediamine), bis-diazonium derivatives (such as bis(p-diazoniumbenzoyl)-ethylenediamine), diisocyanates (such as toluene 2,6-diisocyanate), and bis-active fluorine compounds (such as 1,5-difluoro-2,4-dinitrobenzene). In some aspects, derivatization of immunoglobulins by selectively introducing sulfhydryl groups in the Fc region of an immunoglobulin, using reaction conditions that do not alter the antibody combining site, are contemplated. Antibody conjugates produced according to this methodology are disclosed to exhibit improved longevity, specificity, and sensitivity (U.S. Pat. No. 5,196,066, incorporated herein by reference). Site-specific attachment of effector or reporter molecules, wherein the reporter or effector molecule is conjugated to a carbohydrate residue in the Fc region has also been disclosed in the literature (O'Shannessy et al., *J. Immunol. Methods*, 99(2):153-61 (1987)).

F. Proteins

As used herein, a "protein" or "polypeptide" refers to a molecule comprising at least five amino acid residues. As used herein, the term "wild-type" refers to the endogenous version of a molecule that occurs naturally in an organism. In some embodiments, wild-type versions of a protein or polypeptide are employed, however, in many embodiments of the disclosure, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

Where a protein is specifically mentioned herein, it is in general a reference to a native, wild-type, or recombinant (modified or unmodified) protein or, optionally, a protein in which any signal sequence has been removed. The protein may be isolated directly from the organism of which it is native, produced by recombinant DNA/exogenous expression methods, produced by solid-phase peptide synthesis (SPPS) or other in vitro methods. In particular embodiments, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino acid residues or greater, and any range derivable therein, or derivative of a corresponding amino sequence described or referenced herein. It is contemplated that polypeptides may be mutated by truncation, rendering them shorter than their corresponding wild-type form, also, they might be altered by fusing or conjugating a heterologous protein or polypeptide sequence with a particular function (e.g., for targeting or localization, for enhanced immunogenicity, for purification purposes, etc.). As used herein, the term "domain" refers to any distinct functional or structural unit of a protein or polypeptide, and generally refers to a sequence of amino acids with a structure or function recognizable by one skilled in the art.

The polypeptides or proteins of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) or more variant amino acids (e.g., amino acid substitutions) or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or more contiguous amino acids or nucleic acids, or any range derivable therein, of any of SEQ ID NOs: 1-110.

In some embodiments, the protein or polypeptide may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 (or any derivable range therein) of any of SEQ ID NOs: 1-110.

In some embodiments, the protein or polypeptide may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 (or any derivable range therein) contiguous amino acids of any of SEQ ID NOs: 1-110.

In some embodiments, the polypeptide or protein may comprise at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 (or any derivable range therein) contiguous amino acids that are at least, at most, or exactly 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any derivable range therein) similar, identical, or homologous with one of any of SEQ ID NOs: 1-110.

In some aspects there is a polypeptide starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 of any of SEQ ID NOS: 1-110 and comprising at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 (or any derivable range therein) contiguous amino acids or nucleotides of any of SEQ ID NOs: 1-110.

Nucleotide as well as protein, polypeptide, and peptide sequences for various genes have been previously disclosed, and may be found in the recognized computerized databases.

Two commonly used databases are the National Center for Biotechnology Information's Genbank and GenPept databases (on the World Wide Web at ncbi.nlm.nih.gov) and The Universal Protein Resource (UniProt; on the World Wide Web at uniprot.org). The coding regions for these genes may be amplified and/or expressed using the techniques disclosed herein or as would be known to those of ordinary skill in the art.

It is contemplated that in compositions of the disclosure, there is between about 0.001 mg and about 10 mg of total polypeptide per ml. The concentration of polypeptide in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein).

1. Sequences

Amino acid sequences from 12 light chain variable regions from the TfR1-binding proteins (e.g., humanized antibodies) of the present disclosure are provided in SEQ ID NOs: 1-12 and SEQ ID NO: 107 as follows and in Table 1: L1 (SEQ ID NO: 1), L2 (SEQ ID NO: 2), L3 (SEQ ID NO: 3), L4 (SEQ ID NO: 4), L5 (SEQ ID NO: 5), L6 (SEQ ID NO: 6), L7 (SEQ ID NO: 7), L8 (SEQ ID NO: 8), L9 (SEQ ID NO: 9), L10 (SEQ ID NO: 10), L11 (SEQ ID NO: 11), L12 (SEQ ID NO: 12), and ch128.1L (SEQ ID NO: 107).

TABLE 1

| Poly-peptide | SEQ ID NO: | Sequence |
|---|---|---|
| L1 | 1 | EIVLTQSPATLSLSPGERATLSCSASSSIRYIHWYQQKPGQAPRL LIYDTSNLASGTPARFSGSGSGTDFTLTISSLEPEDFAVYYCHQR NSYPWTFGQGTKVEIK |

TABLE 1-continued

| Poly-peptide | SEQ ID NO: | Sequence |
|---|---|---|
| L2 | 2 | EIVLTQSPATLSVSPGERATLSCSASSSIRYIHWYQQRPGQAPRL<br>LIYDTSNLASGTPARFSGSGSGTDFTLTISSLEPEDFAVYYCHQR<br>NSYPWTFGQGTKVEIK |
| L3 | 3 | EIVLTQSPDFQSVTPKEKVTITCSASSSIRYIHWYQQRPDQSPKL<br>LIYDTSNLASGVPSRFSGSGSGTDFTLTINSLEAEDAATYYCHQR<br>NSYPWTFGQGTKVEIK |
| L4 | 4 | EIVLTQSPATLSVSPGERATLSCSASSSIRYIHWYQQRPGQAPRL<br>LIYDTSNLASGIPARFSGSGSGTDFTLTISSLEPEDFAVYYCHQR<br>NSYPWTFGPGTKVDIK |
| L5 | 5 | EIVLTQSPATLSLSPGERATLSCSASSSIRYIHWYQQKPGQAPRR<br>WIYDTSNLASGTPARFSGSGSGTSYSLTISSLEPEDFAVYYCQQR<br>NSYPWTFGQGTKVEIK |
| L6 | 6 | EIVLTQSPDFQSVTPKEKVTITCSASSSIRYIHWYQQRPDQSPKR<br>WIYDTSNLASGVPSRFSGSGSGTSYSLTINSLEAEDAATYYCQQ<br>RNSYPWTFGQGTKVEIK |
| L7 | 7 | EIVLTQSPATLSLSPGERATLSCSASSSIRYIHWYQQKPGQAPRR<br>WIYDTSNLASGTPARFSGSGSGTSYSLTISSLEPEDFAVYYCHQR<br>NSYPWTFGQGTKVEIK |
| L8 | 8 | EIVLTQSPDFQSVTPKEKVTITCSASSSIRYIHWYQQRPDQSPKR<br>WIYDTSNLASGVPSRFSGSGSGTSYSLTINSLEAEDAATYYCHQ<br>RNSYPWTFGQGTKVEIK |
| L9 | 9 | EIVLTQSPATLSLSPGERATLSCSASSSIRYIHWYQQKPGQAPRR<br>WIYDTSNLASGTPARFSGSGSGTDFTLTISSLEPEDFAVYYCHQR<br>NSYPWTFGQGTKVEIK |
| L10 | 10 | EIVLTQSPDFQSVTPKEKVTITCSASSSIRYIHWYQQRPDQSPKR<br>WIYDTSNLASGVPSRFSGSGSGTDFTLTINSLEAEDAATYYCHQ<br>RNSYPWTFGQGTKVEIK |
| L11 | 11 | EIVLTQSPATLSLSPGERATLSCSASSSIRYIHWYQQKPGQAPRL<br>LIYDTSNLASGTPARFSGSGSGTSYSLTISSLEPEDFAVYYCHQR<br>NSYPWTFGQGTKVEIK |
| L12 | 12 | EIVLTQSPDFQSVTPKEKVTITCSASSSIRYIHWYQQRPDQSPKL<br>LIYDTSNLASGVPSRFSGSGSGTSYSLTINSLEAEDAATYYCHQR<br>NSYPWTFGQGTKVEIK |
| ch128.1L | 107 | QIVLTQSPAIMSVSPGEKVTMTCSASSSIRYIHWYQQRPGTSPKR<br>WIYDTSNLASGVPARFSGSGSGTSYSLTISSMEAEDAATYYCHQ<br>RNSYPWTFGGGTRLEIR |

Amino acid sequences from CDRs from light chain variable regions disclosed herein are provided in SEQ ID NOs: 21-23 and 109 as follows and in Table 2: CDR1L (SEQ ID NO: 21), CDR2L (SEQ ID NO: 22), CDR3L (SEQ ID NO: 23), L5/L6 CDR3 (SEQ ID NO: 109).

TABLE 2

| Polypeptide | SEQ ID NO: | Sequence |
|---|---|---|
| CDR1L | 21 | SASSSIRYIH |
| CDR2L | 22 | DTSNLASGVPA |
| CDR3L | 23 | HQRNSYPW |
| L5/L6 CDR3 | 109 | QQRNSYPW |

Amino acid sequences from FRs from light chain variable regions disclosed herein are provided in SEQ ID NOs: 27-74 as follows and in Table 3: L1 FR1 (SEQ ID NO: 27), L1 FR2 (SEQ ID NO: 28), L1 FR3 (SEQ ID NO: 29), L1 FR4 (SEQ ID NO: 30), L2 FR1 (SEQ ID NO: 31), L2 FR2 (SEQ ID NO: 32), L2 FR3 (SEQ ID NO: 33), L2 FR4 (SEQ ID NO: 34), L3 FR1 (SEQ ID NO: 35), L3 FR2 (SEQ ID NO: 36), L3 FR3 (SEQ ID NO: 37), L3 FR4 (SEQ ID NO: 38), L4 FR1 (SEQ ID NO: 39), L4 FR2 (SEQ ID NO: 40), L4 FR3 (SEQ ID NO: 41), L4 FR4 (SEQ ID NO: 42), L5 FR1 (SEQ ID NO: 43), L5 FR2 (SEQ ID NO: 44), L5 FR3 (SEQ ID NO: 45), L5 FR4 (SEQ ID NO: 46), L6 FR1 (SEQ ID NO: 47), L6 FR2 (SEQ ID NO: 48), L6 FR3 (SEQ ID NO: 49), L6 FR4 (SEQ ID NO: 50), L7 FR1 (SEQ ID NO: 51), L7 FR2 (SEQ ID NO: 52), L7 FR3 (SEQ ID NO: 53), L7 FR4 (SEQ ID NO: 54), L8 FR1 (SEQ ID NO: 55), L8 FR2 (SEQ ID NO: 56), L8 FR3 (SEQ ID NO: 57), L8 FR4 (SEQ ID NO: 58), L9 FR1 (SEQ ID NO: 59), L9 FR2 (SEQ ID NO: 60), L9 FR3 (SEQ ID NO: 61), L9 FR4 (SEQ ID NO: 62), L10 FR1 (SEQ ID NO: 63), L10 FR2 (SEQ ID NO: 64), L10 FR3 (SEQ ID NO: 65), L10 FR4 (SEQ ID NO: 66), L11 FR1 (SEQ ID NO: 67), L11 FR2 (SEQ ID NO: 68), L11 FR3 (SEQ ID NO: 69), L11 FR4 (SEQ ID NO: 70), L12 FR1 (SEQ ID NO: 71), L12 FR2 (SEQ ID NO: 72), L12 FR3 (SEQ ID NO: 73), L12 FR4 (SEQ ID NO: 74).

TABLE 3

| Poly-peptide | SEQ ID NO: | Sequence |
|---|---|---|
| L1 FR1 | 27 | EIVLTQSPATLSLSPGERATLSC |
| L1 FR2 | 28 | WYQQKPGQAPRLLIY |
| L1 FR3 | 29 | RFSGSGSGTDFTLTISSLEPEDFAVYYC |
| L1 FR4 | 30 | TFGQGTKVEIK |
| L2 FR1 | 31 | EIVLTQSPATLSVSPGERATLSC |
| L2 FR2 | 32 | WYQQRPGQAPRLLIY |
| L2 FR3 | 33 | RFSGSGSGTDFTLTISSLEPEDFAVYYC |
| L2 FR4 | 34 | TFGQGTKVEIK |
| L3 FR1 | 35 | EIVLTQSPDFQSVTPKEKVTITC |
| L3 FR2 | 36 | WYQQRPDQSPKLLIY |
| L3 FR3 | 37 | RFSGSGSGTDFTLTINSLEAEDAATYYC |
| L3 FR4 | 38 | TFGQGTKVEIK |
| L4 FR1 | 39 | EIVLTQSPATLSVSPGERATLSC |
| L4 FR2 | 40 | WYQQRPGQAPRLLIY |
| L4 FR3 | 41 | RFSGSGSGTDFTLTISSLEPEDFAVYYC |
| L4 FR4 | 42 | TFGPGTKVDIK |
| L5 FR1 | 43 | EIVLTQSPATLSLSPGERATLSC |
| L5 FR2 | 44 | WYQQKPGQAPRRWIY |
| L5 FR3 | 45 | RFSGSGSGTSYSLTISSLEPEDFAVYYC |
| L5 FR4 | 46 | TFGQGTKVEIK |
| L6 FR1 | 47 | EIVLTQSPDFQSVTPKEKVTITC |
| L6 FR2 | 48 | WYQQRPDQSPKRWIY |
| L6 FR3 | 49 | RFSGSGSGTSYSLTINSLEAEDAATYYC |
| L6 FR4 | 50 | TFGQGTKVEIK |
| L7 FR1 | 51 | EIVLTQSPATLSLSPGERATLSC |
| L7 FR2 | 52 | WYQQKPGQAPRRWIY |
| L7 FR3 | 53 | RFSGSGSGTSYSLTISSLEPEDFAVYYC |

TABLE 3-continued

| Poly-peptide | SEQ ID NO: | Sequence |
|---|---|---|
| L7 FR4 | 54 | TFGQGTKVEIK |
| L8 FR1 | 55 | EIVLTQSPDFQSVTPKEKVTITC |
| L8 FR2 | 56 | WYQQRPDQSPKRWIY |
| L8 FR3 | 57 | RFSGSGSGTSYSLTINSLEAEDAATYYC |
| L8 FR4 | 58 | TFGQGTKVEIK |
| L9 FR1 | 59 | EIVLTQSPATLSLSPGERATLSC |
| L9 FR2 | 60 | WYQQKPGQAPRRWIY |
| L9 FR3 | 61 | RFSGSGSGTDFTLTISSLEPEDFAVYYC |
| L9 FR4 | 62 | TFGQGTKVEIK |
| L10 FR1 | 63 | EIVLTQSPDFQSVTPKEKVTITC |
| L10 FR2 | 64 | WYQQRPDQSPKRWIY |
| L10 FR3 | 65 | RFSGSGSGTDFTLTINSLEAEDAATYYC |
| L10 FR4 | 66 | TFGQGTKVEIK |
| L11 FR1 | 67 | EIVLTQSPATLSLSPGERATLSC |
| L11 FR2 | 68 | WYQQKPGQAPRLLIY |
| L11 FR3 | 69 | RFSGSGSGTSYSLTISSLEPEDFAVYYC |
| L11 FR4 | 70 | TFGQGTKVEIK |
| L12 FR1 | 71 | EIVLTQSPDFQSVTPKEKVTITC |
| L12 FR2 | 72 | WYQQRPDQSPKLLIY |
| L12 FR3 | 73 | RFSGSGSGTSYSLTINSLEAEDAATYYC |
| L12 FR4 | 74 | TFGQGTKVEIK |

Amino acid sequences from 8 heavy chain variable regions from the TfR1-binding proteins (e.g., humanized antibodies) of the present disclosure are provided in SEQ ID NOs: 13-20 and SEQ ID NO: 108 as follows and in Table 4: H1 (SEQ ID NO: 13), H2 (SEQ ID NO: 14), H3 (SEQ ID NO: 15), H4 (SEQ ID NO: 16), H5 (SEQ ID NO: 17), H6 (SEQ ID NO: 18), H7 (SEQ ID NO: 19), H8 (SEQ ID NO: 20), and ch128.1H (SEQ ID NO: 108).

TABLE 4

| Poly-peptide | SEQ ID NO: | Sequence |
|---|---|---|
| H1 | 13 | QVQLVQSGAEVKKPGASVKVSCKASGYSFTGYTMNWVRQAPGQGLEWMGRINPHNGGTDYNQKFKDRVTMTRDTSISTAYMELSRLRSDDTVVYYCARGYYYYSLDYWGQGTLVTVSS |
| H2 | 14 | QVQLVQSGAEVKKPGASMKVSCKASGYSFTGYTMNWVRQAPGENLEWMGRINPHNGGTDYNQKFKDRVPMTRDTSINTAYMELSRLRSGDSVVYYCARGYYYYSLDYWGQGTSVTVSS |
| H3 | 15 | QVQLVQSGAEVKKPGSSMKVSCKASGYSFTGYTMNWVRQAPGENLEWMGRINPHNGGTDYNQKFKDRVPITADKSTNTAYMELSSLRSGDSAVYYCARGYYYYSLDYWGQGTLVTVSS |
| H4 | 16 | QVQLVESGGGVVQPGRSMRLSCAASGYSFTGYTMNWVRQAPGENLEWVARINPHNGGTDYNQKFKDRFPISRDNSKNTLYLQMNSLRAGDSAVYYCARGYYYYSLDYWGQGTTVTVSS |

TABLE 4-continued

| Poly-peptide | SEQ ID NO: | Sequence |
|---|---|---|
| H5 | 17 | QVQLVQSGAEVKKPGSSVKVSCKASGYSFTGYTMNWVRQAPG QGLEWMGRINPHNGGTDYAQKFQDRVTITADESTSTAYMELSS LRSEDTAVYYCARGYYYYSLDYWGQGTLVTVSS |
| H6 | 18 | EVQLVQSGAEVKKPGESLKISCKGSGYSFTGYTMNWVRQMPG KGLEWMGRINPHNGGTDYNQKFKDQVTISADKSISTAYLQWSS LKASDTAMYYCARGYYYYSLDYWGQGTLVTVSS |
| H7 | 19 | QVQLVQSGAEVKKPGSSVKVSCKASGYSFTGYTMNWVRQAPG QGLEWMGRINPHNGGTDYNQKFKDRVTITADKSTSTAYMELSS LRSEDTAVYYCARGYYYYSLDYWGQGTLVTVSS |
| H8 | 20 | QVQLVESGGGVVQPGRSLRLSCAASGYSFTGYTMNWVRQAPG NGLEWVARINPHNGGTDYNQKFKDRFTISRDNSKNTLYLQMNS LRAEDTAVYYCARGYYYYSLDYWGQGTTVTVSS |
| ch128.1H | 108 | EVQLQQSGPELVKPGASMKISCKASGYSFTGYTMNWVKQSHG ENLEWIGRINPHNGGTDYNQKFKDKAPLTVDKSSNTAYMELLS LTSGDSAVYYCARGYYYYSLDYWGQGTSVTVSS |

Amino acid sequences from CDRs from heavy chain variable regions disclosed herein are provided in SEQ ID NOs: 24-26 and 110 as follows and in Table 5: CDR1H (SEQ ID NO: 24), CDR2H (SEQ ID NO: 25), CDR3H (SEQ ID NO: 26), H5 CDR2H (SEQ ID NO: 110).

TABLE 5

| Polypeptide | SEQ ID NO: | Sequence |
|---|---|---|
| CDR1H | 24 | GYSFTGYTMN |
| CDR2H | 25 | RINPHNGGTDYNQKFKD |
| CDR3H | 26 | GYYYYSLDY |
| H5 CDR2 | 110 | RINPHNGGTDYAQKFQD |

Amino acid sequences from FRs from heavy chain variable regions disclosed herein are provided in SEQ ID NOs: 75-106 as follows and in Table 6: H1 FR1 (SEQ ID NO: 75), H1 FR2 (SEQ ID NO: 76), H1 FR3 (SEQ ID NO: 77), H1 FR4 (SEQ ID NO: 78), H2 FR1 (SEQ ID NO: 79), H2 FR2 (SEQ ID NO: 80), H2 FR3 (SEQ ID NO: 81), H2 FR4 (SEQ ID NO: 82), H3 FR1 (SEQ ID NO: 83), H3 FR2 (SEQ ID NO: 84), H3 FR3 (SEQ ID NO: 85), H3 FR4 (SEQ ID NO: 86), H4 FR1 (SEQ ID NO: 87), H4 FR2 (SEQ ID NO: 88), H4 FR3 (SEQ ID NO: 89), H4 FR4 (SEQ ID NO: 90), H5 FR1 (SEQ ID NO: 91), H5 FR2 (SEQ ID NO: 92), H5 FR3 (SEQ ID NO: 93), H5 FR4 (SEQ ID NO: 94), H6 FR1 (SEQ ID NO: 95), H6 FR2 (SEQ ID NO: 96), H6 FR3 (SEQ ID NO: 97), H6 FR4 (SEQ ID NO: 98), H7 FR1 (SEQ ID NO: 99), H7 FR2 (SEQ ID NO: 100), H7 FR3 (SEQ ID NO: 101), H7 FR4 (SEQ ID NO: 102), H8 FR1 (SEQ ID NO: 103), H8 FR2 (SEQ ID NO: 104), H8 FR3 (SEQ ID NO: 105), H8 FR4 (SEQ ID NO: 106).

TABLE 6

| Poly-peptide | SEQ ID NO: | Sequence |
|---|---|---|
| H1 FR1 | 75 | QVQLVQSGAEVKKPGASVKVSCKAS |
| H1 FR2 | 76 | WVRQAPGQGLEWMG |
| H1 FR3 | 77 | RVTMTRDTSISTAYMELSRLRSDDTVVYYCAR |

TABLE 6-continued

| Poly-peptide | SEQ ID NO: | Sequence |
|---|---|---|
| H1 FR4 | 78 | WGQGTLVTVSS |
| H2 FR1 | 79 | QVQLVQSGAEVKKPGASMKVSCKAS |
| H2 FR2 | 80 | WVRQAPGENLEWMG |
| H2 FR3 | 81 | RVPMTRDTSINTAYMELSRLRSGDSVVYYCAR |
| H2 FR4 | 82 | WGQGTSVTVSS |
| H3 FR1 | 83 | QVQLVQSGAEVKKPGSSMKVSCKAS |
| H3 FR2 | 84 | WVRQAPGENLEWMG |
| H3 FR3 | 85 | RVPITADKSTNTAYMELSSLRSGDSAVYYCAR |
| H3 FR4 | 86 | WGQGTLVTVSS |
| H4 FR1 | 87 | QVQLVESGGGVVQPGRSMRLSCAAS |
| H4 FR2 | 88 | WVRQAPGENLEWVA |
| H4 FR3 | 89 | RFPISRDNSKNTLYLQMNSLRAGDSAVYYCAR |
| H4 FR4 | 90 | WGQGTTVTVSS |
| H5 FR1 | 91 | QVQLVQSGAEVKKPGSSVKVSCKAS |
| H5 FR2 | 92 | WVRQAPGQGLEWMG |
| H5 FR3 | 93 | RVTITADESTSTAYMELSSLRSEDTAVYYCAR |
| H5 FR4 | 94 | WGQGTLVTVSS |
| H6 FR1 | 95 | EVQLVQSGAEVKKPGESLKISCKGS |
| H6 FR2 | 96 | WVRQMPGKGLEWMG |
| H6 FR3 | 97 | QVTISADKSISTAYLQWSSLKASDTAMYYCAR |
| H6 FR4 | 98 | WGQGTLVTVSS |
| H7 FR1 | 99 | QVQLVQSGAEVKKPGSSVKVSCKAS |
| H7 FR2 | 100 | WVRQAPGQGLEWMG |
| H7 FR3 | 101 | RVTITADKSTSTAYMELSSLRSEDTAVYYCAR |

35

TABLE 6-continued

| Poly-peptide | SEQ ID NO: | Sequence |
|---|---|---|
| H7 FR4 | 102 | WGQGTLVTVSS |
| H8 FR1 | 103 | QVQLVESGGGVVQPGRSLRLSCAAS |
| H8 FR2 | 104 | WVRQAPGNGLEWVA |
| H8 FR3 | 105 | RFTISRDNSKNTLYLQMNSLRAEDTAVYYCAR |
| H8 FR4 | 106 | WGQGTTVTVSS |

FIG. 1 shows sequence alignments for light chain variable regions and heavy chain variable regions from TfR1-binding proteins of the present disclosure.

2. Variant Polypeptides

The following is a discussion of changing the amino acid subunits of a protein to create an equivalent, or even improved, second-generation variant polypeptide or peptide. For example, certain amino acids may be substituted for other amino acids in a protein or polypeptide sequence with or without appreciable loss of interactive binding capacity with structures such as, for example, antigen-binding regions of antibodies or binding sites on substrate molecules. Since it is the interactive capacity and nature of a protein that defines its functional activity, certain amino acid substitutions can be made in a protein sequence and in its corresponding DNA coding sequence, and nevertheless produce a protein with similar or desirable properties.

The term "functionally equivalent codon" is used herein to refer to codons that encode the same amino acid, such as the six different codons for arginine. Also considered are "neutral substitutions" or "neutral mutations," which refers to a change in the codon or codons that encode biologically equivalent amino acids.

Amino acid sequence variants of the disclosure can be substitutional, insertional, or deletion variants. A variation in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the protein and polypeptide, as compared to wild-type. A variant can comprise an amino acid sequence that is at least 50%, 60%, 70%, 80%, or 90%, including all values and ranges there between, identical to any sequence provided or referenced herein. A variant can include 2, 3, 4, 5, 6, 7, 8, 9, 10, 11, 12, 13, 14, 15, 16, 17, 18, 19, 20, or more substitute amino acids.

It also will be understood that amino acid and nucleic acid sequences may include additional residues, such as additional N- or C-terminal amino acids, or 5' or 3' nucleic acid sequences, respectively, and yet still be essentially identical as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein.

Insertional mutants typically involve the addition of amino acid residues at a non-terminal point in the polypeptide. This may include the insertion of one or more amino acid residues. Terminal additions may also be generated and can include fusion proteins which are multimers or concatemers of one or more peptides or polypeptides described or referenced herein.

Substitutional variants typically contain the exchange of one amino acid for another at one or more sites within the protein or polypeptide, and may be designed to modulate one or more properties of the polypeptide, with or without the loss of other functions or properties. Substitutions may be conservative, that is, one amino acid is replaced with one of similar chemical properties. "Conservative amino acid substitutions" may involve exchange of a member of one amino acid class with another member of the same class. Conservative amino acid substitutions may encompass non-naturally occurring amino acid residues, which are typically incorporated by chemical peptide synthesis rather than by synthesis in biological systems. These include peptidomimetics or other reversed or inverted forms of amino acid moieties.

Alternatively, substitutions may be "non-conservative" (also "nonconservative") In some embodiments, a non-conservative substitution affects a function or activity of the polypeptide. In some embodiments, a non-conservative substitution does not affect a function or activity of the polypeptide. Non-conservative changes typically involve substituting an amino acid residue with one that is chemically dissimilar, such as a polar or charged amino acid for a nonpolar or uncharged amino acid, and vice versa. Non-conservative substitutions may involve the exchange of a member of one of the amino acid classes for a member from another class.

G. Nucleic Acids

In certain embodiments, nucleic acid sequences can exist in a variety of instances such as: isolated segments and recombinant vectors of incorporated sequences or recombinant polynucleotides encoding one or both chains of an antibody, or a fragment, derivative, mutein, or variant thereof, polynucleotides sufficient for use as hybridization probes, polymerase chain reaction (PCR) primers or sequencing primers for identifying, analyzing, mutating or amplifying a polynucleotide encoding a polypeptide, antisense oligonucleotides for inhibiting expression of a polynucleotide, and complementary sequences of the foregoing described herein. The nucleic acids can be single-stranded or double-stranded and can comprise RNA and/or DNA nucleotides and artificial variants thereof (e.g., peptide nucleic acids).

The term "polynucleotide" refers to a nucleic acid molecule that either is recombinant or has been isolated from total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, or at least 95% and above, identity to an amino acid sequence described herein, over the entire length of the sequence; or a nucleotide sequence complementary to said isolated polynucleotide.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. The nucleic acids can be of any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

1. Mutation

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at nonessential amino acid residues. Alternatively, one or more mutations can be introduced into a nucleic acid that selectively changes the biological activity of a polypeptide that it encodes. See, eg., Romain Studer et al., *Biochem. J.,* 449: 581-594 (2013), incorporated herein by reference. For example, the mutation can quantitatively or qualitatively change the biological activity. Examples of quantitative changes include increasing, reducing or eliminating the activity. Examples of qualitative changes include altering the antigen specificity of an antibody.

III. ANTIBODY PRODUCTION

A. Full-length Antibody Production

Methods for preparing and characterizing antibodies for use in diagnostic and detection assays, for purification, and for use as therapeutics are well known in the art as disclosed in, for example, U.S. Pat. Nos. 4,011,308; 4,722,890; 4,016,043; 3,876,504; 3,770,380; and 4,372,745, each incorporated herein by reference (see, e.g., Harlow and Lane (Eds.), *Antibodies: A Laboratory Manual,* Cold Spring Harbor Laboratory, New York, NY, USA (1988), incorporated herein by reference). These antibodies may be polyclonal or monoclonal antibody preparations, monospecific antisera, human antibodies, chimeric antibodies, humanized antibodies, altered antibodies, F(ab')2 fragments, Fab fragments, Fv fragments, single-domain antibodies, dimeric or trimeric antibody fragment constructs, minibodies, or functional fragments thereof which bind to the antigen in question. In certain aspects, polypeptides, peptides, and proteins and immunogenic fragments thereof for use in various embodiments can also be synthesized in solution or on a solid support in accordance with conventional techniques.

In an example, a polyclonal antibody is prepared by immunizing an animal with an antigen or a portion thereof and collecting antisera from that immunized animal. The antigen may be altered compared to an antigen sequence found in nature. In some embodiments, a variant or altered antigenic peptide or polypeptide is employed to generate antibodies. Inocula are typically prepared by dispersing the antigenic composition in a physiologically tolerable diluent to form an aqueous composition. Antisera is subsequently collected by methods known in the arts, and the serum may be used as-is for various applications or else the desired antibody fraction may be purified by well-known methods, such as affinity chromatography.

Methods of making monoclonal antibodies are also well known in the art (e.g., U.S. Pat. No. 4,196,265, herein incorporated by reference in its entirety for all purposes). Typically, this technique involves immunizing a suitable animal, such as a mouse, with a selected immunogenic composition, e.g., a purified or partially purified protein, polypeptide, peptide or domain. Resulting antibody-producing B-cells from the immunized animal, or all dissociated splenocytes, are then induced to fuse with cells from an immortalized cell line to form hybridomas. Myeloma cell lines suited for use in hybridoma-producing fusion procedures preferably are non-antibody-producing and have high fusion efficiency and enzyme deficiencies that render then incapable of growing in certain selective media that support the growth of only the desired fused cells (hybridomas). Typically, the fusion partner includes a property that allows selection of the resulting hybridomas using specific media. For example, fusion partners can be hypoxanthine/aminopterin/thymidine (HAT)-sensitive. Methods for generating hybrids of antibody-producing spleen or lymph node cells and myeloma cells usually comprise mixing somatic cells with myeloma cells in the presence of an agent or agents (chemical or electrical) that promote the fusion of cell membranes. Next, selection of hybridomas can be performed by culturing the cells by single-clone dilution in microtiter plates, followed by testing the individual clonal supernatants (after about two to three weeks) for the desired reactivity. Fusion procedures for making hybridomas, immunization protocols, and techniques for isolation of immunized splenocytes for fusion are known in the art.

Other techniques for producing monoclonal antibodies include the viral or oncogenic transformation of B-lymphocytes, a molecular cloning approach may be used to generate a nucleic acid or polypeptide, the selected lymphocyte antibody method (SLAM) (see, e.g., Babcook et al., *Proc. Natl. Acad. Sci. USA,* 93:7843-7848 (1996), the preparation of combinatorial immunoglobulin phagemid libraries from RNA isolated from the spleen of the immunized animal and selection of phagemids expressing appropriate antibodies, or producing a cell expressing an antibody from a genomic sequence of the cell comprising a modified immunoglobulin locus using Cre-mediated site-specific recombination (see, e.g., U.S. Pat. No. 6,091,001).

Monoclonal antibodies may be further purified using filtration, centrifugation, and various chromatographic methods such as high-performance liquid chromatography (HPLC). Monoclonal antibodies may be further screened or optimized for properties relating to specificity, avidity, half-life, immunogenicity, binding association, binding disassociation, or overall functional properties relative to being a treatment for infection. Thus, monoclonal antibodies may have alterations in the amino acid sequence of CDRs, including insertions, deletions, or substitutions with a conserved or non-conserved amino acid.

The immunogenicity of a particular immunogen composition can be enhanced by the use of non-specific stimulators of the immune response, known as adjuvants. Adjuvants that may be used in accordance with embodiments include, but are not limited to, interleukin-1 (IL-1), IL-2, IL-4, IL-7, IL-12, interferon-γ (INF-γ), granulocyte-macrophage colony-stimulating factor (GM-CSF), Bacillus Calmette-Guérin (BCG), aluminum hydroxide, muramyl dipeptide (MDP) compounds, muramyl tripeptide phosphatidyl ethanolamine (MTP-PE), lipid A, and monophosphoryl lipid A (MPL). Exemplary adjuvants may include complete Freund's adjuvant (a non-specific stimulator of the immune response containing killed *Mycobacterium tuberculosis*), incomplete Freund's adjuvants, and/or aluminum hydroxide adjuvant. In addition to adjuvants, it may be desirable to co-administer biologic response modifiers (BRM), such as but not limited to, cytokines such as INF-ß, IL-2, or IL-12, or genes encoding proteins involved in immune helper functions, such as B7-1 (CD80) or B7-2 (CD86). A phage-display system can be used to expand antibody molecule populations in vitro.

B. Antibody Fragment Production

Antibody fragments that retain the ability to recognize the antigen of interest will also find use herein. A number of antibody fragments are known in the art that comprise antigen-binding sites capable of exhibiting immunological binding properties of an intact antibody molecule and can be subsequently modified by methods known in the arts. Functional fragments, including only the variable regions of the heavy and light chains, can also be produced using standard techniques such as recombinant production or preferential proteolytic cleavage of immunoglobulin molecules. These fragments are known as Fv. See, e.g., Inbar et al., *Proc. Nat. Acad. Sci. USA,* 69(9):2659-2662 (1972); Hochman et al.,

*Biochem.,* 15(12):2706-2710 (1976); and Ehrlich et al., *Biochem.,* 19(17):4091-4096 (1980).

scFvs may be prepared by fusing DNA encoding a peptide linker between DNA molecules encoding the two variable domain polypeptides ($V_L$ and $V_H$). scFvs can form antigen-binding monomers, or they can form multimers (e.g., dimers, trimers, or tetramers), depending on the length of a flexible linker between the two variable domains. By combining different $V_L$- and $V_H$-comprising polypeptides, one can form multimeric scFvs that bind to different epitopes. Antigen-binding fragments are typically produced by recombinant DNA methods known to those skilled in the art. Although the two domains of the Fv fragment, $V_L$ and $V_H$, are coded for by separate genes, they can be joined using recombinant methods by a synthetic linker that enables them to be made as a single chain polypeptide (known as single chain Fv (sFv or scFv); see e.g., Bird et al., *Science,* 242(4877):423-426 (1988). Design criteria include determining the appropriate length to span the distance between the C-terminus of one chain and the N-terminus of the other, wherein the linker is generally formed from small hydrophilic amino acid residues that do not tend to coil or form secondary structures. Suitable linkers generally comprise polypeptide chains of alternating sets of glycine and serine residues, and may include glutamic acid and lysine residues inserted to enhance solubility. Antigen-binding fragments are screened for utility in the same manner as intact antibodies. Such fragments include those obtained by N-terminal and/or C-terminal deletions, where the remaining amino acid sequence is substantially identical to the corresponding positions in the naturally occurring sequence deduced, for example, from a full-length cDNA sequence.

Also contemplated herein are non-peptide compounds having properties analogous to those of a template peptide. These types of non-peptide compounds are termed "peptide mimetics" or "peptidomimetics".

Also contemplated are "antibody-like binding peptidomimetics" (ABiPs), which are peptide-like molecules that act as pared-down antibodies and have certain advantages of longer serum half-life as well as less cumbersome synthesis methods. These analogs can be peptides, non-peptides or combinations of peptide and non-peptide regions. Peptide mimetics that are structurally similar to therapeutically useful peptides may be used to produce a similar therapeutic or prophylactic effect. Such compounds are often developed with the aid of computerized molecular modeling. Generally, peptidomimetics of the disclosure are proteins that are structurally similar to an antibody displaying a desired biological activity, such as the ability to bind a protein, but have one or more peptide linkages optionally replaced by a linkage selected from: —CH2NH—, —CH2S—, —CH2-CH2-, —CH—CH— (cis and trans), —COCH2-, —CH(OH)CH2-, and —CH2SO— by methods well known in the art. Systematic substitution of one or more amino acids of a consensus sequence with a D-amino acid of the same type (e.g., D-lysine in place of L-lysine) may be used in certain embodiments of the disclosure to generate more stable proteins. In addition, constrained peptides comprising a consensus sequence or a substantially identical consensus sequence variation may be generated by methods known in the art (Rizo et al., *Ann. Rev. Biochem.,* 61:387 (1992), incorporated herein by reference), for example, by adding internal cysteine residues capable of forming intramolecular disulfide bridges which cyclize the peptide.

Once generated, a phage display library can be used to improve the immunological binding affinity of Fab molecules using known techniques. See, e.g., Figini et al., *J.*

*Mol. Biol.,* 239:68-78 (1994). The coding sequences for the heavy and light chain portions of the Fab molecules selected from the phage display library can be isolated or synthesized and cloned into any suitable vector or replicon for expression. Any suitable expression system can be used.

IV. OBTAINING ANTIBODIES

In some aspects, there are nucleic acid molecules encoding antibody or antibody-like polypeptides (e.g., heavy or light chain, variable domain only, or full-length). These may be generated by methods known in the art, e.g., isolated from B cells of mice that have been immunized and isolated, phage display, expressed in any suitable recombinant expression system and allowed to assemble to form antibody molecules.

A. Expression

The nucleic acid molecules may be used to express large quantities of recombinant antibodies, such as chimeric or humanized antibodies, single chain antibodies, antigen-binding fragments, immunoadhesins, diabodies, bi-specific antibodies, mutated antibodies, and other antibody derivatives. If the nucleic acid molecules are derived from a non-human, non-transgenic animal, the nucleic acid molecules may be used for antibody humanization.

1. Vectors

In some aspects, contemplated are expression vectors comprising a nucleic acid molecule encoding a polypeptide of the desired sequence or a portion thereof (e.g., a fragment containing one or more CDRs or one or more variable region domains). Expression vectors comprising the nucleic acid molecules may encode the heavy chain, light chain, or the antigen-binding portion thereof. In some aspects, expression vectors comprising nucleic acid molecules may encode fusion proteins, modified antibodies, antibody fragments, and/or probes thereof. In addition to control sequences that govern transcription and translation, vectors and expression vectors may contain nucleic acid sequences that serve other functions as well.

To express the antibodies, or antigen-binding fragments thereof, DNA encoding partial or full-length light and heavy chains are inserted into expression vectors such that the gene area is operatively linked to transcriptional and translational control sequences. In some aspects, a vector that encodes a functionally complete human $C_H$ or $C_L$ immunoglobulin sequence with appropriate restriction sites engineered so that any $V_H$ or $V_L$ sequence can be easily inserted and expressed. Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Such sequences and methods of using the same are well known in the art.

2. Expression Systems

Numerous expression systems exist that comprise at least a part or all of the expression vectors discussed above. Prokaryote- and/or eukaryote-based systems can be employed for use with an embodiment to produce nucleic acid sequences, or their cognate polypeptides, proteins and peptides. Commercially and widely available systems include, but are not limited to bacterial, mammalian, yeast, and insect cell systems. Different host cells have characteristic and specific mechanisms for the post-translational processing and modification of proteins. Appropriate cell lines or host systems can be chosen to ensure the correct modification and processing of the foreign protein expressed. Those skilled in the art are able to express a vector to produce a nucleic acid sequence or its cognate polypeptide using an appropriate expression system.

3. Methods of Gene Transfer

Suitable methods for nucleic acid delivery to effect expression of compositions are anticipated to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624; 5,981,274; 5,945,100; 5,780,448; 5,736,524; 5,702,932; 5,656,610; 5,589,466; and 5,580,859, each incorporated herein by reference), including microinjection (U.S. Pat. No. 5,789,215, incorporated herein by reference); by electroporation (U.S. Pat. No. 5,384,253, incorporated herein by reference); by calcium phosphate precipitation; by using DEAE dextran followed by polyethylene glycol; by direct sonic loading; by liposome mediated transfection; by microprojectile bombardment (PCT Publication Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG mediated transformation of protoplasts (U.S. Pat. Nos. 4,684,611 and 4,952,500, each incorporated herein by reference); by desiccation/inhibition mediated DNA uptake. Other methods include viral transduction, such as gene transfer by lentiviral or retroviral transduction.

4. Host Cells

In another aspect, contemplated are the use of host cells into which a recombinant expression vector has been introduced. Antibodies and antibody-like molecules can be expressed in a variety of cell types. An expression construct encoding an antibody can be transfected into cells according to a variety of methods known in the art. Vector DNA can be introduced into prokaryotic or eukaryotic cells via conventional transformation or transfection techniques. Some vectors may employ control sequences that allow it to be replicated and/or expressed in both prokaryotic and eukaryotic cells. In certain aspects, the antibody expression construct can be placed under control of a promoter that is linked to immune cell (e.g., T-cell) activation. Control of antibody expression allows immune cells, such as tumor-targeting immune cells, to sense their surroundings and perform real-time modulation of cytokine signaling, both in the T cells themselves and in surrounding endogenous immune cells. One of skill in the art would understand the conditions under which to incubate host cells to maintain them and to permit replication of a vector. Also understood and known are techniques and conditions that would allow large-scale production of vectors and their cognate polypeptides. Host cells which may be used to express antibodies and other antigen-binding proteins of the present disclosure include, for example, murine myeloma cells (e.g., NSO/1 cells, SP2/0-Ag14 cells, and P3X63Ag8.653 cells), Chinese hamster ovary (CHO) cells, baby hamster kidney 21 (BHK21) cells, human embryonic kidney 293 (HEK293) cells, fibrosarcoma HT-1080 cells, and PER.C6 cells.

For stable transfection of mammalian cells, it is known, depending upon the expression vector and transfection technique used, only a small fraction of cells may integrate the foreign DNA into their genome. In order to identify and select these integrants, a selectable marker (e.g., for resistance to antibiotics) is generally introduced into the host cells along with the gene of interest. Cells stably transfected with the introduced nucleic acid can be identified by drug selection (e.g., cells that have incorporated the selectable marker gene will survive, while the other cells die), among other methods known in the arts.

B. Isolation

The nucleic acid molecule encoding either or both of the entire heavy and light chains of an antibody or the variable regions thereof may be obtained from any source that produces antibodies. Methods of isolating mRNA encoding an antibody are well known in the art. The sequences of human heavy and light chain constant region genes are also known in the art. Nucleic acid molecules encoding the full-length heavy and/or light chains may then be expressed in a cell into which they have been introduced and the antibody isolated.

V. METHODS OF TREATMENT AND ADMINISTRATION OF THERAPEUTIC COMPOSITIONS

The therapy provided herein may comprise administration of a therapeutic agent (e.g., a TfR1-binding protein). In some embodiments, therapy provided herein comprises administration of a combination of therapeutic agents, such as a TfR1-binding protein and an additional therapeutic agent. An additional therapeutic may be an additional cancer therapeutic. An additional therapeutic may be a chemotherapy. The therapy or therapies may be administered in any suitable manner known in the art. For example, for a combination therapy, the TfR1-binding protein and the additional therapeutic agent may be administered sequentially (at different times) or concurrently (at the same time). In some embodiments, the TfR1-protein and the additional therapeutic agent are administered in a separate composition. In some embodiments, the TfR1-binding protein and the additional therapeutic agent are in the same composition.

Embodiments of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 mg/kg, mg/kg, μg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 μM to 150 μM. In another embodiment, the effective dose provides a blood level of about 4 μM to 100 μM.; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or μM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, or 12-week intervals, including all ranges there between.

A. General Pharmaceutical Compositions

In some embodiments, pharmaceutical compositions are administered to a subject. Different aspects may involve administering an effective amount of a composition to a subject. In some embodiments, an antibody or antigen-binding fragment capable of binding to TfR1 may be administered to the subject to protect against or treat a condition (e.g., cancer, a neurological condition, an autoimmune disorder, or a viral infection). Alternatively, an expression vector encoding one or more such antibodies or polypeptides or peptides may be given to a subject as a preventative treatment. Additionally, such compositions can be administered in combination with an additional therapeutic agent (e.g., a chemotherapeutic). Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, anti-bacterial and anti-fungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, subcutaneous, or intraperitoneal routes. Typically, such compositions can be prepared as either liquid solutions or suspensions; solid forms suitable for use to prepare solutions or suspensions upon the addition of a liquid prior to injection can also be prepared; and the preparations can also be emulsified.

The pharmaceutical forms suitable for injectable use include sterile aqueous solutions or dispersions; formulations including, for example, aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization or an equivalent procedure. Generally, dispersions are prepared by incorporating the various sterilized active ingredients into a sterile vehicle, which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral or intravenous administration. Alternatively, administration may be by orthotopic, intradermal, subcutaneous, intramuscular, intraperitoneal, or intranasal administration. Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are specific to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

B. Methods of Treatment

Compositions (e.g., antigen-binding proteins) or methods described herein may be administered to any patient having a condition in which targeting TfR1 may have therapeutic benefit. Conditions in which targeting TfR1 may have a therapeutic benefit include, for example, a condition associated with the increased expression of TfR1 and/or a condition in which targeting TfR1 may be used to specifically deliver a therapeutic or to block the cell entry of an infectious agent. Such conditions include, for example, cancer, neurological disorders, autoimmune or inflammatory disorders, and viral infections (e.g. arenaviruses). Also contemplated are methods for treatment of a condition by targeting a therapeutic to a cell or tissue that expresses TfR1. For example, the TfR1-binding proteins of the disclosure may be conjugated to a therapeutic and used to target the therapeutic to a particular cell or tissue type. As one example, a TfR1-binding protein may be used to target a nucleic acid therapeutic (e.g., antisense oligonucleotide, siRNA, etc.) to a cell for reducing expression of a gene, RNA, and/or protein in the cell. An example of such an approach is described in Sugo et al., *J Control Release,* 237:1-13 (2016), incorporated herein by reference.

The term "treatment" or "treating" means any treatment of a disease in a mammal, including:

(i) preventing the disease, that is, causing the clinical symptoms of the disease not to develop by administration of a protective composition prior to the induction of the disease;

(ii) suppressing the disease, that is, causing the clinical symptoms of the disease not to develop by administration of a protective composition after the inductive event but prior to the clinical appearance or reappearance of the disease;

(iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance.

1. Treatment of Cancer

Disclosed herein, in some embodiments, are methods for treating cancer comprising providing to a subject in need thereof a TfR1-binding protein disclosed herein. The cancer may be a solid tumor, metastatic cancer, non-metastatic cancer, or hematopoetic cancer. In certain embodiments, the cancer may originate in the bone marrow, bone, cartilage, brain, breast, bladder, kidney, ureter, uterus-endometrial, cervix-endocervix, esophagus, stomach, duodenum, small intestine, appendix, cecum, colon, rectum, anal canal, head and neck, salivary glands, thyroid, pancreatobilliary, spleen, liver, lung, oropharynx, larynx, ovary, fallopian tubes, prostate, testis, eye, skin, adipose tissue, synovium, nerve cell/sheath, or thymus.

The cancer may specifically be of one or more of the following tissue origin: glandular epithelium, superface epithelium, fibroblasts, cartilage/bone, striate muscle, smooth muscle, blood vessels, endothelium, fat, neuroectoderm, hepatocytes, and chorionic epithelium. There are different histological types of malignancies (non-epithelial tumors and epithelial tumors). The cancer may specifically be of one or more of the following histological types, though it is not limited to these: liposarcoma, fibrosarcoma, myxosarcoma, chondrosarcoma, osteosarcoma, synovial sarcoma, epithelioid sarcoma, epithelioid angiosarcoma, alveolar soft part sarcoma, malignant fibrous histiocytoma, leiomyosarcoma, rhabdomyosaroma, embryonal rhabdomyosarcoma, alveolar rhabdomyosarcoma, cystosarcoma phyllodes, angiosarcoma, lymphangiosarcoma, invasive meningioma, leukemias, Hodgkin lymphoma (HL) and non-Hodgkin lymphoma (NHL), multiple myeloma (MM) including plasma cell leukemia, mast cell leukemia/sarcoma, erytroleukemia, myeloid leukemia/sarcoma, basophilic leukemia, eosinophilic leukemia, monocytic leukemia, hairy cell leukemia, neurogenic sarcoma, Kaposi's sarcoma, granular cell tumor, gastrointestinal stromal tumor, neuroblastoma, medulloblastoma, retinoblastoma, melanoma includiding amelanotic, malignant teratomas, primitive neuroectodermal tumor, Ewing's sarcoma, glioblastoma, astrocytoma, neurofibrosarcoma, adamantinoma, chordoma, ependymoma, astrocytoma, oligoendroblastoma, cerebelar sarcoma, germ-cell tumors of ovary and testes (seminoma, dysgerminoma, gynandroblastoma), non-germ cell tumors (embryonic carcinoma, choriocarcinoma, yolk sac tumor, immature teratoma, teratocarcinoma, sex chord-stromal tumors (granulosa cell and Sertoli-Leydig cell tumors). Malignancies also include undifferentiated carcinoma, well-differentiated carcinoma, keratinizing and nonkeratinizing squamous cell carcinoma, basaloid squamous cell carcinoma, NUT midline carcinoma, spindle cell carcinoma, giant cell carcinoma, pleomorphic carcinoma, transitional cell carcinoma, adenocarcinoma, lepidic adenocarcinoma, acinar adenocarcinoma, papillary adenocarcinoma, solid adenocarcinoma, micropapillary adenocarcinoma, mucinous adenocarcinoma, epithelial myoepithelial carcinoma, adenosquamous carcinoma, basal cell carcinoma, large cell carcinoma, large cell neuroendocrine carcinoma, mucoepidermoid carcinoma, adenoid cystic carcinoma, acinic cell carcinoma, hepatocellular carcinoma, cholangiocarcinoma, choriocarcinoma, neuroendocrine carcinoma, lymphoepithelial carcinoma, thymoma, thymic carcinoma, thyroid carcinoma (anaplastic, hurthle cell, papillary, follicular, and medullary thyroid carcinoma), cutaneous squamous cell carcinoma, Paget's disease of the anus, clear cell renal cell carcinoma, cervical carcinoma, urothelial carcinoma, small and non-mall cell carcinoma of lung, endometrial adenocarcinoma, adrenocortical carcinoma, chromophobe renal cell carcinoma, granular cell carcinoma, malignant mesothelioma, skin appendages carcinoma (hair, nails, sebaceous glands, sweat glands and mammary glands), Merkel cell carcinoma, pilomatrix carcinoma, apocrine gland carcinoma, papillary eccrine carcinoma, sebaceous adenocarcinoma, mucoepidermoid carcinoma, invasive and noninvasive ductal/lobular carcinoma of breast, inflammatory breast carcinoma, Paget's disease of the breast/nipple and areola, medullary carcinoma, colloid (mucinous) carcinoma including signet ring variant, papillary carcinoma, tubular carcinoma, adenoid cytic carcinoma, secretory carcinoma, carcinoma with metaplasia, ovarian surface epithelium-stroma tumors including serous, mucinous, endometrioid, clear cell, Brunner cells, and transitional cells tumors. In some embodiments, methods for treating cancer comprise providing a TfR1-binding protein and an additional cancer therapeutic. References throughout the application to treatment of cancer may also, in some embodiments, be applied to methods for treatment of premalignant conditions, e.g., for the prevention of cancer development.

Methods may involve the determination, administration, or selection of an appropriate cancer "management regimen" and predicting the outcome of the same. As used herein the phrase "management regimen" refers to a management plan that specifies the type of examination, screening, diagnosis, surveillance, care, and treatment (such as dosage, schedule and/or duration of a treatment) provided to a subject in need thereof (e.g., a subject diagnosed with cancer).

The selected treatment regimen can be an aggressive one which is expected to result in the best clinical outcome (e.g., complete cure of the disease) or a more moderate one which may relieve symptoms of the disease yet results in incomplete cure of the disease. The type of treatment can include a surgical intervention, administration of a therapeutic drug such as a TfR1-binding protein, chemotherapy, immunotherapy, an exposure to radiation therapy and/or any combination thereof. The dosage, schedule and duration of treatment can vary, depending on the severity of disease and the selected type of treatment, and those of skill in the art are capable of adjusting the type of treatment with the dosage, schedule, and duration of treatment.

Biomarkers like TfR1 that can predict the efficacy of certain therapeutic regimen and can be used to identify patients who will receive benefit of a conventional single or combined modality therapy before treatment begins or to modify or design a future treatment plan after treatment. In the same way, those patients who do not receive much benefit from such conventional single or combined modality therapy and can offer them alternative treatment(s) may be identified.

2. Treatment of a Neurological Condition

Disclosed herein, in some embodiments, are methods for treating a neurological condition comprising providing to a subject in need thereof a TfR1-binding protein disclosed herein. The neurological condition may be primary or secondary parkinsonism. In some embodiments, the parkinsonism is multiple system atrophy, progressive supranuclear palsy, corticobasal syndrome, dementia with Lewy bodies, drug-induced parkinsonism, or vascular parkinsonism. The neurological condition may be Alzheimer's disease. TfR1-binding proteins disclosed herein may be useful in, for example, delivery of one or more therapeutic agents across the BBB, thereby treating a neurological condition. In some embodiments, methods for treating a neurological conditions comprise delivering a therapeutic agent linked to a TfR1-binding protein across the BBB of an individual.

3. Treatment of an Autoimmune or Inflammatory Disorder

Disclosed herein, in some embodiments, are methods for treating an autoimmune disorder comprising providing to a subject in need thereof a TfR1-binding protein disclosed herein. TfR1-binding proteins disclosed herein may be useful in, for example, inducing immunosuppression, thereby treating an autoimmune disorder. A TfR1-binding protein may be provided together with one or more additional therapeutics for treatment of an autoimmune disorder.

The autoimmune condition or inflammatory condition amenable for treatment may include, but not be limited to conditions such as diabetes (e.g. Type 1 diabetes), graft rejection, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, Type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, X-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, transmural colitis, and/or autoimmune inflammatory bowel disease), pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus.

4. Treatment of a Viral Infection

Disclosed herein, in some embodiments, are methods for treating a viral infection comprising providing to a subject in need thereof a TfR1-binding protein disclosed herein. A viral infection may be an infection with an arenavirus. In some embodiments, the arenavirus is Junin virus, Machupo virus, Guanarito virus, Sabia virus, or Chapare virus. TfR1-binding proteins disclosed herein may be useful in, for example, preventing a virus from binding to TfR1, thereby preventing cell entry and treating a viral infection.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure. The Examples should not be construed as limiting in any way. The contents of all cited references (including literature references, issued patents, published patent applications, and GenBank Accession numbers as cited throughout this application) are hereby expressly incorporated by reference. When definitions of terms in documents that are incorporated by reference herein conflict with those used herein, the definitions used herein govern.

Example 1—Development of Antibodies Targeting TfR1

Multiple humanized variants (hu128.1) of the mouse 128.1 V regions were designed using the method described in Almagro et al., *Humanization of Antibodies, In: Making and Using Antibodies: A Practical Handbook*, 395-419. Howard and Kaser (Eds.), $2^{nd}$ Edition CRC Press, Boca Raton, FL, USA (2013). The hu128.1 variants and the V regions of the mouse parental antibody were cloned as human IgG1/kappa, allotype G1m3 to yield humanized IgG1 molecules and the chimeric control (ch128.1), transiently expressed in CHO cells, and purified by Evitria AG (Zurich, Switzerland). hu128.1 antibody variants were compared with ch128.1 in ELISA and flow cytometry for antigen (TfR1) binding.

Initially, five humanized $V_H$ chains (H1, H2, H3, H4, and H5) and four humanized $V_L$ chains (L1, L2, L3, and L4) were generated. The humanized $V_H$ chains were designed by combining the amino acid sequence of the CDRs (using Chothia's and Kabat's definition of the CDR1 and Kabat's definition in the CDR2 and CDR3) with the amino acid sequences of human FRs. The humanized $V_L$ chains were generated by combining the amino acid sequences of the mouse CDRs (Kabat's definition) with human FRs.

The human FRs were selected from the repertoire of human functional germline genes compiled at the International Immunogenetics Information System (IMGT). The selection process of the human FRs comprised several criteria, including (1) homology with the mouse V regions, (2) structural similarity of the hypervariable regions between the mouse and human V genes, (3) high use frequency in the known antibody sequences, and (4) human FRs known to be developable. A detailed description of the selection process can be found at Almagro et al., *Humanization of Antibodies, In: Making and Using Antibodies: A Practical Handbook*, 395-419. Howard and Kaser (Eds.), $2^{nd}$ Edition CRC Press, Boca Raton, FL, USA (2013), incorporated by reference herein in its entirety.

Each of the five $V_H$ chains were combined with each of the four $V_L$ chains to produce the following twenty hu128.1 antibodies: H1L1, H1L2, H1L3, H1L4, H2L1, H2L2, H2L3, H2L4, H3L1, H3L2, H3L3, H3L4, H4L1, H4L2, H4L3, H4L4, H5L1, H5L2, H5L3, and H5L4. Sequences for H1-H5 and L1-L4 are provided in Table 7 and FIG. 1.

TABLE 7

| Poly-peptide | SEQ ID NO: | Sequence |
|---|---|---|
| L1 | 1 | EIVLTQSPATLSLSPGERATLSCSASSSIRYIHWYQQKPGQAPRL LIYDTSNLASGTPARFSGSGSGTDFTLTISSLEPEDFAVYYCHQR NSYPWTFGQGTKVEIK |
| L2 | 2 | EIVLTQSPATLSVSPGERATLSCSASSSIRYIHWYQQRPGQAPRL LIYDTSNLASGTPARFSGSGSGTDFTLTISSLEPEDFAVYYCHQR NSYPWTFGQGTKVEIK |
| L3 | 3 | EIVLTQSPDFQSVTPKEKVTITCSASSSIRYIHWYQQRPDQSPKL LIYDTSNLASGVPSRFSGSGSGTDFTLTINSLEAEDAATYYCHQR NSYPWTFGQGTKVEIK |
| L4 | 4 | EIVLTQSPATLSVSPGERATLSCSASSSIRYIHWYQQRPGQAPRL LIYDTSNLASGIPARFSGSGSGTDFTLTISSLEPEDFAVYYCHQR NSYPWTFGPGTKVDIK |
| H1 | 13 | QVQLVQSGAEVKKPGASVKVSCKASGYSFTGYTMNWVRQAP GQGLEWMGRINPHNGGTDYNQKFKDRVTMTRDTSISTAYMEL SRLRSDDTVVYYCARGYYYYSLDYWGQGTLVTVSS |
| H2 | 14 | QVQLVQSGAEVKKPGASMKVSCKASGYSFTGYTMNWVRQAP GENLEWMGRINPHNGGTDYNQKFKDRVPMTRDTSINTAYMEL SRLRSGDSVVYYCARGYYYYSLDYWGQGTSVTVSS |
| H3 | 15 | QVQLVQSGAEVKKPGSSMKVSCKASGYSFTGYTMNWVRQAP GENLEWMGRINPHNGGTDYNQKFKDRVPITADKSTNTAYMEL SSLRSGDSAVYYCARGYYYYSLDYWGQGTLVTVSS |

TABLE 7-continued

| Poly-peptide | SEQ ID NO: | Sequence |
|---|---|---|
| H4 | 16 | QVQLVESGGGVVQPGRSMRLSCAASGYSFTGYTMNWVRQAP GENLEWVARINPHNGGTDYNQKFKDRFPISRDNSKNTLYLQMN SLRAGDSAVYYCARGYYYYSLDYWGQGTTVTVSS |
| H5 | 17 | QVQLVQSGAEVKKPGSSVKVSCKASGYSFTGYTMNWVRQAPG QGLEWMGRINPHNGGTDYAQKFQDRVTITADESTSTAYMELSS LRSEDTAVYYCARGYYYYSLDYWGQGTLVTVSS |

After synthesis, cloning into appropriate vectors, and transient expression of each variant in CHO cells using standard methods, all hu128.1 containing H2, H3, and H4 resulted in low expression yield and could not be processed further. Antibodies containing H1 and H5 showed adequate expression yield after Protein A purification. However, binding to TfR1 as assessed by ELISA was negligible. Binding to TfR1 on the cell surface as assessed by flow cytometry showed only a weak signal. Based on the analysis of the expression, quality of the expression products after purification, and binding profile obtained for this set of humanized variants, new $V_H$ constructs were generated as follows:

H3 without backmutations (named H7)

H4 without backmutations (named H8)

H6=128.1 CDRs combined with the FR of the human germline genes IGHV5-51*01/4 with no backmutations.

From these additional constructs, the following 12 additional hu128.1 antibodies were generated: H6L1, H6L2, H6L3, H6L4 H7L1, H7L2, H7L3, H7L4, H8L1, H8L2, H8L3, H8L4. Sequences for H6, H7, and H8 are provided in Table 8 and FIG. 1.

TABLE 8

| Poly-peptide | SEQ ID NO: | Sequence |
|---|---|---|
| H6 | 18 | EVQLVQSGAEVKKPGESLKISCKGSGYSFTGYTMNWVRQMPG KGLEWMGRINPHNGGTDYNQKFKDQVTISADKSISTAYLQWSS LKASDTAMYYCARGYYYYSLDYWGQGTLVTVSS |
| H7 | 19 | QVQLVQSGAEVKKPGSSVKVSCKASGYSFTGYTMNWVRQAPG QGLEWMGRINPHNGGTDYNQKFKDRVTITADKSTSTAYMELSS LRSEDTAVYYCARGYYYYSLDYWGQGTLVTVSS |
| H8 | 20 | QVQLVESGGGVVQPGRSLRLSCAASGYSFTGYTMNWVRQAPG NGLEWVARINPHNGGTDYNQKFKDRFTISRDNSKNTLYLQMNS LRAEDTAVYYCARGYYYYSLDYWGQGTTVTVSS |

Additionally, variants were generated by combining the mouse $V_H$ domain from the chimeric antibody ch128.1 with each of the $V_L$ humanized variants L1, L2, L3, and L4, yielding the following four hybrid antibodies: ChimL1, ChimL2, ChimL3, ChimL4.

Antibodies comprising H6 and H7 showed significantly lower antigen-binding compared to the chimeric ch128.1 antibody. Antibodies comprising H8 showed no antigen-binding. All four hybrid antibodies showed poor binding to antigen by ELISA and flow cytometry.

These results suggested that the $V_L$ chains L1-L4 led to molecules with poor antigen-binding. To confirm these results, $V_H$ chains H6, H7, and H8 were combined with the mouse $V_L$ chains from the chimeric antibody ch128.1 to generate the following three antibodies: H6Chim, H7Chim, and H8Chim. All three of these hybrid antibodies showed similar antigen-binding as the ch128.1 antibody, confirming that $V_L$ chains L1-L4 were responsible for the impaired antigen-binding.

Based on these observations and analysis of the ch128.1 antibody structure, eight new $V_L$ chains were designed: L5, L6, L7, L8, L9, L10, L11, and L12. These $V_L$ chains were designed based on L1 and L3 and backmutations in the framework 2 (FR2) and framework 3 (FR3) regions to remove non-conservative amino acids introduced during the humanization process of L1 and L3. These new $V_L$ chains L5-L12 were combined with H6 and H8 to generate 16 additional hu128.1 antibodies: H6L5, H6L6, H6L7, H6L8, H6L9, H6L10, H6L11, H6L12 H8L5, H8L6, H8L7, H8L8, H8L9, H8L10, H8L11, and H8L12. Sequences for L5-L12 are provided in Table 9 and FIG. 1.

TABLE 9

| Poly-peptide | SEQ ID NO: | Sequence |
|---|---|---|
| L5 | 5 | EIVLTQSPATLSLSPGERATLSCSASSSIRYIHWYQQKPGQAPRR WIYDTSNLASGTPARFSGSGSGTSYSLTISSLEPEDFAVYYCQQR NSYPWTFGQGTKVEIK |
| L6 | 6 | EIVLTQSPDFQSVTPKEKVTITCSASSSIRYIHWYQQRPDQSPKR WIYDTSNLASGVPSRFSGSGSGTSYSLTINSLEAEDAATYYCQQ RNSYPWTFGQGTKVEIK |
| L7 | 7 | EIVLTQSPATLSLSPGERATLSCSASSSIRYIHWYQQKPGQAPRR WIYDTSNLASGTPARFSGSGSGTSYSLTISSLEPEDFAVYYCHQR NSYPWTFGQGTKVEIK |
| L8 | 8 | EIVLTQSPDFQSVTPKEKVTITCSASSSIRYIHWYQQRPDQSPKR WIYDTSNLASGVPSRFSGSGSGTSYSLTINSLEAEDAATYYCHQ RNSYPWTFGQGTKVEIK |
| L9 | 9 | EIVLTQSPATLSLSPGERATLSCSASSSIRYIHWYQQKPGQAPRR WIYDTSNLASGTPARFSGSGSGTDFTLTISSLEPEDFAVYYCHQR NSYPWTFGQGTKVEIK |
| L10 | 10 | EIVLTQSPDFQSVTPKEKVTITCSASSSIRYIHWYQQRPDQSPKR WIYDTSNLASGVPSRFSGSGSGTDFTLTINSLEAEDAATYYCHQ RNSYPWTFGQGTKVEIK |
| L11 | 11 | EIVLTQSPATLSLSPGERATLSCSASSSIRYIHWYQQKPGQAPRL LIYDTSNLASGTPARFSGSGSGTSYSLTISSLEPEDFAVYYCHQR NSYPWTFGQGTKVEIK |
| L12 | 12 | EIVLTQSPDFQSVTPKEKVTITCSASSSIRYIHWYQQRPDQSPKL LIYDTSNLASGVPSRFSGSGSGTSYSLTINSLEAEDAATYYCHQR NSYPWTFGQGTKVEIK |

All hu128.1 antibody variants containing H6 bound the antigen to varying degrees as demonstrated by ELISA and/or flow cytometry (performed as described in Example 3). H6L11 and H6L12 showed the least consistent results and weakest binding by ELISA. With regards to hu128.1 antibody variants containing H8, in general H8L5, H8L6, H8L7, H8L8, H8L9, and H8L10 showed similar binding levels to the chimeric antibody (ch128.1). H8L11 and H8L12 showed no binding by ELISA and very weak binding by flow cytometry. These results demonstrated that the backmutations at positions 45 (L to R) and 46 (L to W) were critical for optimal binding of the hu128.1 antibody variants to TfR1. A semiquantitative summary of the antigen-binding results from ELISA (using soluble human TfR1) and flow cytometry (using KMS-11 cells) is provided in Table 10.

TABLE 10

| Antibody | Binding (ELISA) | Binding (Flow Cytometry) |
|---|---|---|
| ch128.1 | +++ | +++ |
| H6L5 | +++ | +++ |
| H6L6 | +++ | +++ |
| H6L7 | +++ | +++ |
| H6L8 | +++ | +++ |
| H6L9 | +++ | +++ |
| H6L10 | +++ | +++ |
| H6L11 | ++ | +++ |
| H6L12 | ++ | +++ |
| H8L5 | +++ | +++ |
| H8L6 | +++ | +++ |
| H8L7 | +++ | +++ |
| H8L8 | +++ | +++ |

TABLE 10-continued

| Antibody | Binding (ELISA) | Binding (Flow Cytometry) |
|---|---|---|
| H8L9 | +++ | +++ |
| H8L10 | +++ | +++ |
| H8L11 | – | + |
| H8L12 | – | + |

+++: high binding,
++: medium binding,
+: low binding,
–: no binding

Example 2—Thermal Stability

A thermal stability study of antibodies H6L7, H6L9, H8L9, and H8L10, together with chimeric antibody ch128.1, was performed.

Methods

The Protein Thermal Shift™ Starter Kit (Thermo Fisher Scientific, Inc., Waltham, MA, USA) was used in a thermal stability study of antibodies H6L7, H6L9, H8L9, and H8L10, together with chimeric antibody ch128.1. Protein Thermal Shift dye was diluted from 1000× as provided in the kit to an 8× stock and 2.5 µL was added to 3 µg of antibody per well of a 96-well PCR plate for fast thermocyclers (VWR International, LLC, Wayne, PA, USA). Final concentration of each antibody was 0.15 mg/mL. Each sample was run in quadruplicate and the plate was sealed with MicroAmp® Optical Adhesive Film (Thermo Fisher Scientific, Inc.). The samples were then run on an Applied Biosystems 7500 Fast Real Time PCR system using the assay template from the company. In this system, proteins unfold as the sample is heated over time and the dye binds hydrophobic regions of the protein that are exposed as the protein unfolds and then fluoresces. Data were analyzed using the derivative method to estimate the melting temperature (Tm) from the melt curve using the Protein Thermal Shift Analysis Software from Life Technologies.
Results
H8L9 and H8L10 showed similar thermal stability when compared to ch128.1 as evidenced by the overlapping peaks in the derivative plot (FIG. 2A) and similar Tm values (FIG. 2B). However, the humanized antibodies containing the H6 heavy chain (H6L7 and H6L9) showed increased thermal stability as indicated by the shift to the right in the peak on the derivative plot (FIG. 2A) and higher Tm values (FIG. 2B).

Example 3—Antigen-Binding

Antigen-binding studies of antibodies H6L7, H6L9, H8L9, and H8L10, together with ch128.1, were performed.
ELISA
Methods
Immulon-H2B plates (Thermo Fisher Scientific, Inc.) were coated overnight at 4° C. with soluble 5 μg/mL TfR1 (sCD71) in 50 mM carbonate/bicarbonate buffer, pH 9.3. Human sCD71 was obtained from either Cal Tech (California Institute of Technology, Pasadena, CA, USA) or Kerafast, Inc., while cynomolgus monkey (*Macaca fascicularis*) sCD71 was purchased from Sino Biological, Inc. (Wayne, PA, USA). Plates were washed with PBS and blocked with 3% BSA in PBS. Serial 2-fold dilutions of antibodies (200-3.12 ng/mL) were added to the plate in duplicates and incubated overnight at 4° C. Binding was detected with an AP-conjugated goat anti-human κ antibody (MilliporeSigma) and AP substrate, p-nitrophenyl phosphate disodium (MilliporeSigma), dissolved in diethanolamine buffer (9.6% diethanolamine (v/v), 0.24 mM MgCl$_2$ in water, pH 9.8). Plates were read at absorbance 405 nm using a FilterMax F5 multi-mode microplate reader (Molecular Devices, Sunnyvale, CA, USA).
Results
Antigen binding to human TfR1 or cynomolgus monkey TfR1, as tested by the ELISA assay, showed no difference in binding between the parental chimeric antibody and all four humanized versions (FIGS. 3A-3D). This indicated that the binding affinities of the humanized antibodies is similar to the affinity of the chimeric antibody. These data also showed that the humanized versions of ch128.1 do not lose the cross-reactivity for cynomolgus monkey TfR1 that is exhibited by the chimeric antibody.
Flow Cytometry
Methods
KMS-11 cells (Namba et al., *In Vitro Cell. Dev. Biol.* 25(8):723-729 (1989)), a kind gift from Dr. Lawrence Boise (Emory University, Atlanta, GA, USA), and MM.1S cells (Greenstein et al., *Exp. Hematol.*, 31(4):271-282 (2003)), purchased from the American Type Culture Collection (ATCC, Manassas, VA, USA; ATCC® CRL-2974™) human MM cells were incubated with 2 μg of humanized antibodies or the control antibodies (ch128.1 as a positive control or a negative isotype control IgG1) for 2 hours on ice. Binding was detected using a PE-conjugated anti-human κ antibody. Samples were analyzed on an LSRII analytical flow cytometer (BD Biosciences, San Jose, CA, USA) and 10,000 events were collected. Histograms were created using the FSC Software Version 3 (De Novo Software, Glendale, CA, USA). MM.1S cells were used in the data shown in FIGS. 4A-4F. KMS-11 cells were used for data summarized in Table 10.

58

Results
Binding of all humanized antibodies to human cells expressing the TfR1 was similar to ch128.1 (FIGS. 4A-4F). This was consistent with the ELISA data and showed that the high binding affinity for the antigen (TfR1), described as K$_D$=5.7 nM for ch128.1 (Helguera et al., *J. Virol.*, 86(7):4024-4028 (2012)), was retained following the humanization process.

Figures 5A, 5B:
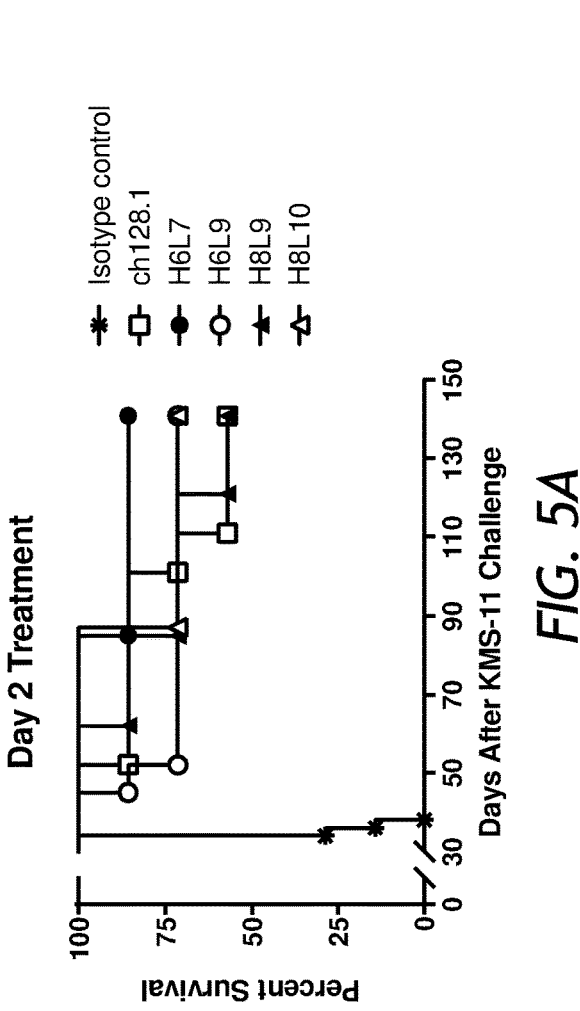
FIGS. 5A and 5B show results from the in vivo efficacy study (day 2 treatment) using KMS-11 cells as described in Example 4. The numbers of animals per group are indicated in parentheses in the left hand column of each table. Median survival and p-values comparing humanized antibody treatment with ch128.1 or the negative control group are also shown.
Figures 6A, 6B:
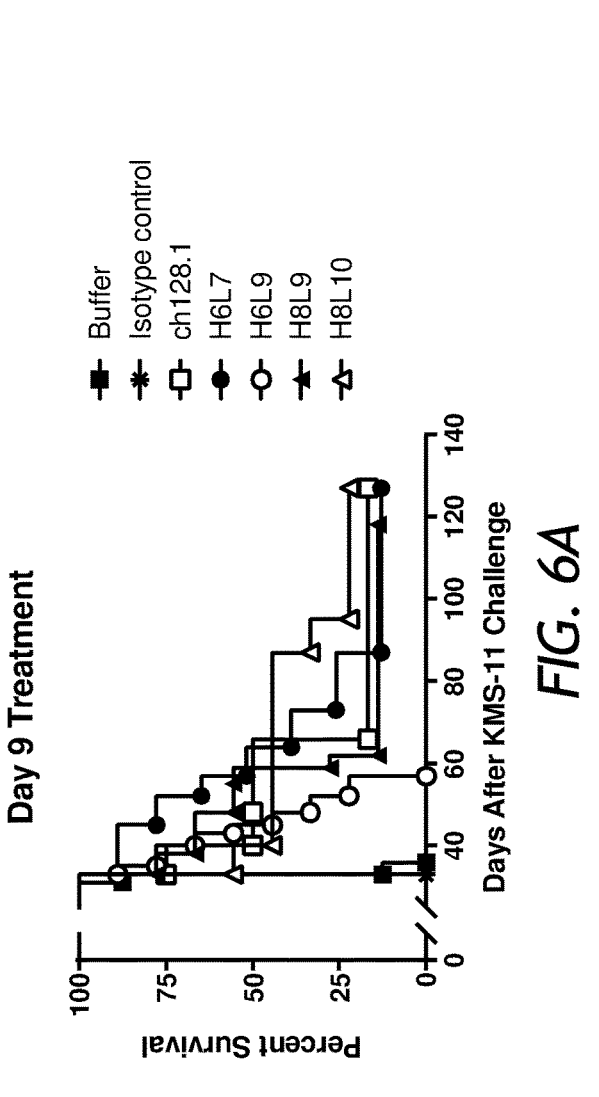
FIGS. 6A and 6B show results from the in vivo efficacy study (day 9 treatment) using KMS-11 cells as described in Example 4. The numbers of animals per group are indicated in parentheses in the left hand column of each table. Median survival and p-values comparing humanized antibody treatment with ch128.1 or the negative control groups are also shown.

Example 4—In Vivo Efficacy in a Disseminated Xenograft Model of Human MM Using KMS-11 Cells In vivo efficacy studies of antibodies H6L7, H6L9, H8L9, and H8L10, together with ch128.1, were performed.
Methods
C.B-17 severe combined immune deficiency (SCID)-Beige mice were obtained and housed in the Defined-Flora Mouse Facility in the Department of Radiation Oncology at UCLA. Female mice 8 to 12 weeks old were exposed to 3 (Gy) total body irradiation using a Gammacell 40 (Best Theratronics, Ltd., Ottawa, Ontario, Canada) on the day before tumor challenge. Five million KMS-11 human MM cells in Hanks' balanced salt solution (HBSS) were injected intravenously via the tail vein. Mice were randomized into treatment groups and treatments were given intravenously in phosphate-buffered saline (PBS) 2 or 9 days after tumor challenge. Antibodies were given at a dose of 100 μg per mouse. PBS alone was injected in the negative control group. Survival was based on the time from tumor challenge to the development of hind-limb paralysis, when mice were euthanized. Survival plots were generated using GraphPad Prism Version 8 (GraphPad Software, Inc., La Jolla, CA, USA). Median survival and differences in survival (log-rank test) were determined using the same software. Results were considered significant if p<0.05.
Results
In the early-stage disease model where mice were treated 2 days after tumor challenge, all humanized antibodies prolonged the survival of the mice and in all cases, median survival was not determined since most animals did not develop tumors (FIGS. 5A and 5B). The anti-tumor activity of all humanized antibodies was significantly different compared to the istoype control antibody, indicating that they had a protective effect. These effects were not statistically significant compared to the chimeric antibody, indicating that the protective effects between the humanized and chimeric antibodies are similar. However, the H6L7-treated group showed the highest number of surviving animals. In the late-stage disease model, where mice were treated 9 days after tumor challenge, the results are similar in that all humanized antibodies showed a significant prolongation of survival compared to either the buffer alone or isotype control treated groups (FIGS. 6A and 6B). In this study, median survival was determined for each treatment group. Again, there were no significant differences in the anti-tumor effects when comparing the humanized antibodies to the chimeric antibody. However, H6L7 and H8L9 showed the longest median survival of all of the treatment groups.

Example 5—In Vivo Efficacy in a Disseminated Xenograft Model of Human MM Using MM.1S Cells In vivo efficacy studies of the H6L7 antibody together with ch128.1 were performed.

Methods

Female SCID-Beige mice 8 to 12 weeks old were exposed to 3 Gy total body irradiation on the day before tumor challenge. Five million MM.1S human MM cells in HBSS were injected intravenously via the tail vein. Mice were randomized into treatment groups and treatments were given in PBS intravenously 9 days after tumor challenge. The IgG1 isotype (negative) control, ch128.1, or H6L7 antibodies were given at a dose of 100 μg per mouse. Survival was based on the time from tumor challenge to the development of hind-limb paralysis, when mice were euthanized. Survival plots were generated using GraphPad Prism Version 8. Median survival and differences in survival (log-rank test) were determined using the same software. Results were considered significant if $p<0.05$.

Results

Figures 7A, 7B:
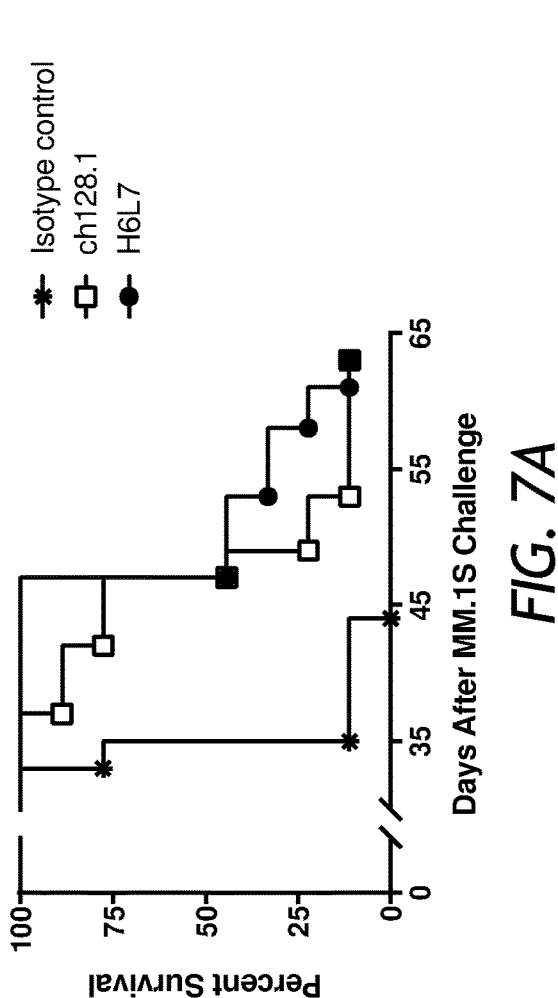
FIGS. 7A and 7B show results from the in vivo efficacy study using MM.1S cells described in Example 5. The numbers of animals per group are indicated in parentheses in the left hand column of each table. Median survival and p-values comparing humanized antibody treatment with ch128.1 or the negative control group are also shown.

In this late-stage disease model using MM.1S cells, both ch128.1 and H6L7 prolonged the survival of the mice compared to the isotype control treated group (FIGS. 7A and 7B).

Example 6—In Vivo Efficacy in a Disseminated Xenograft Model of Human AIDS-NHL Using 2F7-BR44 Cells In vivo efficacy studies of the H6L7 antibody were performed.

Methods

Infection with the human immunodeficiency virus (HIV) and the development of acquired immunodeficiency syndrome (AIDS) increases the risk of developing B-cell lymphomas (Ziegler et al., *Ann. NY Acad. Sci.*, 437:412-419, (1984); Gibson et al., *AIDS*, 28(15): 2313-2318 (2014); and Seaberg et al., *Cancer*, 116(23):5507-5516 (2010)). The human 2F7 cell line is an Epstein-Barr Virus (EBV)-positive B-cell AIDS-associated non-Hodgkin lymphoma (AIDS-NHL) of the Burkitt lymphoma (BL) subtype (ATCC CRL-10237™—Discontinued) (Widney et al., *Tumour Biol.*, 24(2):82-93 (2003); Ng et al., *Blood*, 83(4):1067-1078 (1984)). The 2F7-BR44 clone is variant of 2F7 that forms metastases in the brain of mice when injected intravenously (Wen et al., *Nat. Biomed. Eng.*, 3(9):706-716 (2019)).

Female SCID-Beige mice 8 to 12 weeks old were challenged intravenously via the tail vein with 5 million 2F7-BR44 cells in HBSS. Mice were randomized into treatment groups and treatments were given intravenously in PBS 2 days after tumor challenge. The IgG1 isotype control or H6L7 antibodies were given at a dose of 100 μg per mouse. PBS alone was also used as a negative control group. Survival was based on the time from tumor challenge until the mice became moribund or developed hind-limb paralysis, when mice were euthanized. Survival plots were generated using GraphPad Prism Version 8. Median survival and differences in survival (log-rank test) were determined using the same software. Results were considered significant if $p<0.05$.

Results

Figures 8A, 8B:
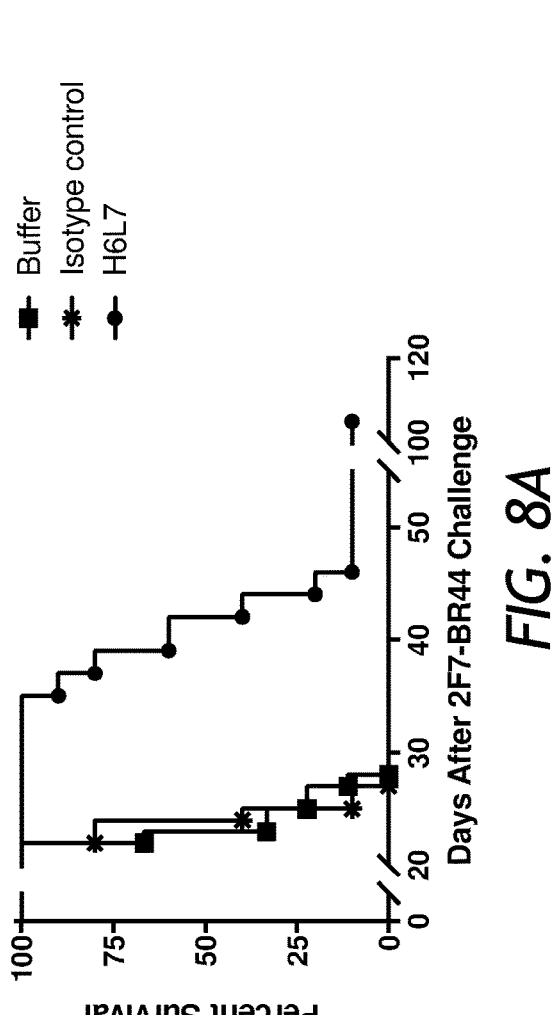
FIGS. 8A and 8B show results from the in vivo efficacy study using 2F7-BR44 cells as described in Example 6. The numbers of animals per group are indicated in parentheses in the left hand column of each table. Median survival and p-values comparing humanized antibody treatment with the negative control groups are also shown.

In this model using 2F7-BR44 cells, H6L7 prolonged the survival of the mice compared to either the PBS or the isotype control treated groups. (FIGS. 8A and 8B)

Example 7—In Vivo Efficacy in a Disseminated Xenograft Model of Human AIDS-NHL Using JB Cells In vivo efficacy studies of the H6L7 antibody were performed.

Methods

The human JB cell line is an EBV-negative B-cell AIDS-NHL of the BL subtype (Moses et al., *Nat. Med.*, 3(11) 1242-1249 (1997)) and were a kind gift from Dr. Ashley Moses (Oregon Health Sciences University, Portland, OR, USA). Female SCID-Beige mice 8 to 12 weeks old were challenged intravenously via the tail vein with 5 million JB cells in HBSS. Mice were randomized into treatment groups and treatments were given intravenously in PBS 2 days after tumor challenge. The IgG1 isotype (negative) control or H6L7 antibodies were given at a dose of 100 μg per mouse. Survival was based on the time from tumor challenge until the mice became moribund or developed hind-limb paralysis, when mice were euthanized. Survival plots were generated using GraphPad Prism Version 8. Median survival and differences in survival (log-rank test) were determined using the same software. Results were considered significant if $p<0.05$.

Results

Figures 9A, 9B:
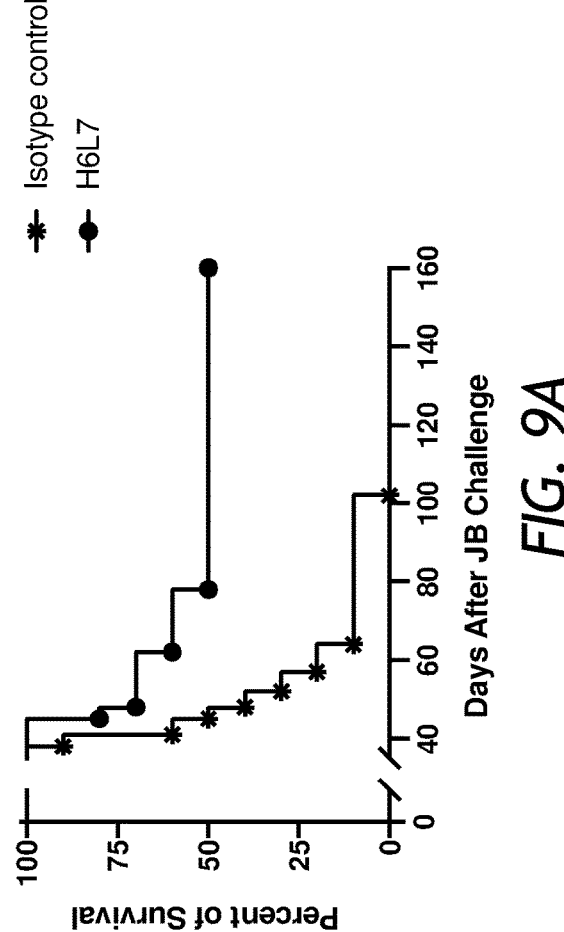
FIGS. 9A and 9B show results from the in vivo efficacy study using JB cells as described in Example 7. The numbers of animals per group are indicated in parentheses in the left hand column of each table. Median survival and p-values comparing humanized antibody treatment with the negative control group are also shown.

In this model using JB cells, H6L7 prolonged the survival of the mice compared to the isotype control treated group (FIGS. 9A and 9B).

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

The references recited in the application, to the extent that they provide exemplary procedural or other details supplementary to those set forth herein, are specifically incorporated herein by reference.

What is claimed is:

1. A transferrin receptor 1 (TfR1)-binding protein comprising:

(a) a light chain variable region comprising SEQ ID NO: 5, SEQ ID NO: 6, SEQ ID NO: 7, SEQ ID NO: 8, SEQ ID NO: 9, or SEQ ID NO: 10, wherein the light chain variable region comprises an arginine, a lysine, or a histidine at amino acid position 45 and a tryptophan, a phenylalanine, a methionine, a valine, an isoleucine, a glycine, or an alanine at amino acid position 46; and (b) a heavy chain variable region comprising SEQ ID NO: 18 or SEQ ID NO: 20.

2. The TfR1-binding protein of claim 1, wherein the light chain variable region comprises an arginine at position 45 relative to SEQ ID NO: 5, SEQ ID NO: 6, SEQ ID NO: 7, SEQ ID NO: 8, SEQ ID NO: 9, or SEQ ID NO: 10.

3. The TfR1-binding protein of claim 1, wherein the light chain variable region comprises a tryptophan at position 46 relative to SEQ ID NO: 5, SEQ ID NO: 6, SEQ ID NO: 7, SEQ ID NO: 8, SEQ ID NO: 9, or SEQ ID NO: 10.

4. The TfR1-binding protein of claim 1, wherein the light chain variable region comprises SEQ ID NO: 5, SEQ ID NO: 6, SEQ ID NO: 7, SEQ ID NO: 8, SEQ ID NO: 9, or SEQ ID NO: 10.

5. The TfR1-binding protein of claim 1, wherein the heavy chain variable region comprises SEQ ID NO: 18 or SEQ ID NO: 20.

6. The TfR1-binding protein of claim 1, wherein the light chain variable region comprises SEQ ID NO: 7 and the heavy chain variable region comprises SEQ ID NO: 18.

7. The TfR1-binding protein of claim 1, wherein the light chain variable region comprises SEQ ID NO: 9 and the heavy chain variable region comprises SEQ ID NO: 18.

8. The TfR1-binding protein of claim 1, wherein the light chain variable region comprises SEQ ID NO: 9 and the heavy chain variable region comprises SEQ ID NO: 20.

9. The TfR1-binding protein of claim 1, wherein the light chain variable region comprises SEQ ID NO: 10 and the heavy chain variable region comprises SEQ ID NO: 20.

10. A TfR1-binding protein comprising: (a) a light chain variable region comprising SEQ ID NO: 5, SEQ ID NO: 6, SEQ ID NO: 7, SEQ ID NO: 8, SEQ ID NO: 9, or SEQ ID NO: 10; and (b) a heavy chain variable region comprising SEQ ID NO: 18 or SEQ ID NO: 20.

11. A cell comprising the TfR1-binding protein of claim 1.

12. The cell of claim 11, wherein the cell comprises the TfR1-binding protein and wherein the cell secretes the TfR1-binding protein outside the cell.

13. The cell of claim 11, wherein the cell comprises the TfR1-binding protein and wherein the TfR1-binding protein is attached to a surface of the cell.

14. A method for treating cancer in a subject comprising providing to the subject a therapeutically effective amount of the TfR1-binding protein of claim 1.

15. The method of claim 14, wherein the cancer is a brain cancer.

16. The method of claim 14, wherein the cancer is a blood cancer.

17. The method of claim 16, wherein the blood cancer is a B-cell malignancy.

18. The method of claim 17, wherein the B-cell malignancy is multiple myeloma or non-Hodgkin lymphoma (NHL).

19. The method of claim 14, wherein the TfR1-binding protein comprises SEQ ID NO: 7 and SEQ ID NO: 18, SEQ ID NO: 9 and SEQ ID NO:18, SEQ ID NO: 9 and SEQ ID NO: 20, or SEQ ID NO: 10 and SEQ ID NO: 20.

20. The method of claim 14, wherein the TfR1-binding protein comprises SEQ ID NO: 7 and SEQ ID NO:18.

* * * * *

SEQUENCE LISTING

```
<160> NUMBER OF SEQ ID NOS: 110

<210> SEQ ID NO 1
<211> LENGTH: 106
<212> TYPE: PRT
<213> ORGANISM: Artificial Sequence
<220> FEATURE:
<223> OTHER INFORMATION: Synthetic peptide
```

-continued

```
<400> SEQUENCE: 1

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Lys Pro Gly Gln Ala Pro Arg Leu Leu Ile Tyr
        35                  40                  45

Asp Thr Ser Asn Leu Ala Ser Gly Thr Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Asn Ser Tyr Pro Trp Thr
                85                  90                  95

Phe Gly Gln Gly Thr Lys Val Glu Ile Lys
            100                 105

<210> SEQ ID NO 2
<211> LENGTH: 106
<212> TYPE: PRT
<213> ORGANISM: Artificial Sequence
<220> FEATURE:
<223> OTHER INFORMATION: Synthetic peptide

<400> SEQUENCE: 2

Glu Ile Val Leu Thr Gln Ser Pro Ala Thr Leu Ser Val Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Arg Pro Gly Gln Ala Pro Arg Leu Leu Ile Tyr
        35                  40                  45

Asp Thr Ser Asn Leu Ala Ser Gly Thr Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Asn Ser Tyr Pro Trp Thr
                85                  90                  95

Phe Gly Gln Gly Thr Lys Val Glu Ile Lys
            100                 105

<210> SEQ ID NO 3
<211> LENGTH: 106
<212> TYPE: PRT
<213> ORGANISM: Artificial Sequence
<220> FEATURE:
<223> OTHER INFORMATION: Synthetic peptide

<400> SEQUENCE: 3

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Arg Tyr Ile
            20                  25                  30

His Trp Tyr Gln Gln Arg Pro Asp Gln Ser Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80
```

-continued

```
Asp Ala Ala Thr Tyr Tyr Cys His Gln Arg Asn Ser Tyr Pro Trp Thr
            85                  90                  95

Phe Gly Gln Gly Thr Lys Val Glu Ile Lys
            100                 105

<210> SEQ ID NO 4
<211> LENGTH: 106
<212> TYPE: PRT
<213> ORGANISM: Artificial Sequence
<220> FEATURE:
<223> OTHER INFORMATION: Synthetic peptide

<400> SEQUENCE: 4

Glu Ile Val Leu Thr Gln Ser Pro Ala Thr Leu Ser Val Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Arg Pro Gly Gln Ala Pro Arg Leu Leu Ile Tyr
        35                  40                  45

Asp Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Asn Ser Tyr Pro Trp Thr
            85                  90                  95

Phe Gly Pro Gly Thr Lys Val Asp Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: Synthetic peptide

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Lys Pro Gly Gln Ala Pro Arg Arg Trp Ile Tyr
        35                  40                  45

Asp Thr Ser Asn Leu Ala Ser Gly Thr Pro Ala Arg Phe Ser Gly Ser
    50                  55                  60

Gly Ser Gly Thr Ser Tyr Ser Leu Thr Ile Ser Ser Leu Glu Pro Glu
65                  70                  75                  80

Asp Phe Ala Val Tyr Tyr Cys Gln Gln Arg Asn Ser Tyr Pro Trp Thr
            85                  90                  95

Phe Gly Gln Gly Thr Lys Val Glu Ile Lys
            100                 105

<210> SEQ ID NO 6
<211> LENGTH: 106
<212> TYPE: PRT
<213> ORGANISM: Artificial Sequence
<220> FEATURE:
<223> OTHER INFORMATION: Synthetic peptide

<400> SEQUENCE: 6

Glu Ile Val Leu Thr Gln Ser Pro Asp Phe Gln Ser Val Thr Pro Lys
```

-continued

```
1               5                   10                  15

Glu Lys Val Thr Ile Thr Cys Ser Ala Ser Ser Ser Ile Arg Tyr Ile
            20                  25                  30

His Trp Tyr Gln Gln Arg Pro Asp Gln Ser Pro Lys Arg Trp Ile Tyr
            35                  40                  45

Asp Thr Ser Asn Leu Ala Ser Gly Val Pro Ser Arg Phe Ser Gly Ser
        50                  55                  60

Gly Ser Gly Thr Ser Tyr Ser Leu Thr Ile Asn Ser Leu Glu Ala Glu
65                  70                  75                  80

Asp Ala Ala Thr Tyr Tyr Cys Gln Gln Arg Asn Ser Tyr Pro Trp Thr
                85                  90                  95

Phe Gly Gln Gly Thr Lys Val Glu Ile Lys
                100                 105

<210> SEQ ID NO 7
<211> LENGTH: 106
<212> TYPE: PRT
<213> ORGANISM: Artificial Sequence
<220> FEATURE:
<223> OTHER INFORMATION: Synthetic peptide

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Lys Pro Gly Gln Ala Pro Arg Arg Trp Ile Tyr
            35                  40                  45

Asp Thr Ser Asn Leu Ala Ser Gly Thr Pro Ala Arg Phe Ser Gly Ser
        50                  55                  60

Gly Ser Gly Thr Ser Tyr Ser Leu Thr Ile Ser Ser Leu Glu Pro Glu
65                  70                  75                  80

Asp Phe Ala Val Tyr Tyr Cys His Gln Arg Asn Ser Tyr Pro Trp Thr
                85                  90                  95

Phe Gly Gln Gly Thr Lys Val Glu Ile Lys
                100                 105

<210> SEQ ID NO 8
<211> LENGTH: 106
<212> TYPE: PRT
<213> ORGANISM: Artificial Sequence
<220> FEATURE:
<223> OTHER INFORMATION: Synthetic peptide

<400> SEQUENCE: 8

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Arg Tyr Ile
            20                  25                  30

His Trp Tyr Gln Gln Arg Pro Asp Gln Ser Pro Lys Arg Trp Ile Tyr
            35                  40                  45

Asp Thr Ser Asn Leu Ala Ser Gly Val Pro Ser Arg Phe Ser Gly Ser
        50                  55                  60

Gly Ser Gly Thr Ser Tyr Ser Leu Thr Ile Asn Ser Leu Glu Ala Glu
65                  70                  75                  80

Asp Ala Ala Thr Tyr Tyr Cys His Gln Arg Asn Ser Tyr Pro Trp Thr
                85                  90                  95
```

```
Phe Gly Gln Gly Thr Lys Val Glu Ile Lys
            100                 105

<210> SEQ ID NO 9
<211> LENGTH: 106
<212> TYPE: PRT
<213> ORGANISM: Artificial Sequence
<220> FEATURE:
<223> OTHER INFORMATION: Synthetic peptide

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Arg Tyr Ile
            20                  25                  30

His Trp Tyr Gln Gln Lys Pro Gly Gln Ala Pro Arg Arg Trp Ile Tyr
        35                  40                  45

Asp Thr Ser Asn Leu Ala Ser Gly Thr Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Asn Ser Tyr Pro Trp Thr
                85                  90                  95

Phe Gly Gln Gly Thr Lys Val Glu Ile Lys
            100                 105

<210> SEQ ID NO 10
<211> LENGTH: 106
<212> TYPE: PRT
<213> ORGANISM: Artificial Sequence
<220> FEATURE:
<223> OTHER INFORMATION: Synthetic peptide

<400> SEQUENCE: 10

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Arg Tyr Ile
            20                  25                  30

His Trp Tyr Gln Gln Arg Pro Asp Gln Ser Pro Lys Arg Trp Ile Tyr
        35                  40                  45

Asp Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys His Gln Arg Asn Ser Tyr Pro Trp Thr
                85                  90                  95

Phe Gly Gln Gly Thr Lys Val Glu Ile Lys
            100                 105

<210> SEQ ID NO 11
<211> LENGTH: 106
<212> TYPE: PRT
<213> ORGANISM: Artificial Sequence
<220> FEATURE:
<223> OTHER INFORMATION: Synthetic peptide

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Arg Tyr Ile
```

-continued

```
                20              25              30

His Trp Tyr Gln Gln Lys Pro Gly Gln Ala Pro Arg Leu Leu Ile Tyr
        35              40              45

Asp Thr Ser Asn Leu Ala Ser Gly Thr Pro Ala Arg Phe Ser Gly Ser
    50              55              60

Gly Ser Gly Thr Ser Tyr Ser Leu Thr Ile Ser Ser Leu Glu Pro Glu
65              70              75              80

Asp Phe Ala Val Tyr Tyr Cys His Gln Arg Asn Ser Tyr Pro Trp Thr
                85              90              95

Phe Gly Gln Gly Thr Lys Val Glu Ile Lys
            100             105
```

```
<210> SEQ ID NO 12
<211> LENGTH: 106
<212> TYPE: PRT
<213> ORGANISM: Artificial Sequence
<220> FEATURE:
<223> OTHER INFORMATION: Synthetic peptide

<400> SEQUENCE: 12

Glu Ile Val Leu Thr Gln Ser Pro Asp Phe Gln Ser Val Thr Pro Lys
1               5               10              15

Glu Lys Val Thr Ile Thr Cys Ser Ala Ser Ser Ser Ile Arg Tyr Ile
                20              25              30

His Trp Tyr Gln Gln Arg Pro Asp Gln Ser Pro Lys Leu Leu Ile Tyr
        35              40              45

Asp Thr Ser Asn Leu Ala Ser Gly Val Pro Ser Arg Phe Ser Gly Ser
    50              55              60

Gly Ser Gly Thr Ser Tyr Ser Leu Thr Ile Asn Ser Leu Glu Ala Glu
65              70              75              80

Asp Ala Ala Thr Tyr Tyr Cys His Gln Arg Asn Ser Tyr Pro Trp Thr
                85              90              95

Phe Gly Gln Gly Thr Lys Val Glu Ile Lys
            100             105
```

```
<210> SEQ ID NO 13
<211> LENGTH: 118
<212> TYPE: PRT
<213> ORGANISM: Artificial Sequence
<220> FEATURE:
<223> OTHER INFORMATION: Synthetic peptide

<400> SEQUENCE: 13

Gln Val Gln Leu Val Gln Ser Gly Ala Glu Val Lys Lys Pro Gly Ala
1               5               10              15

Ser Val Lys Val Ser Cys Lys Ala Ser Gly Tyr Ser Phe Thr Gly Tyr
                20              25              30

Thr Met Asn Trp Val Arg Gln Ala Pro Gly Gln Gly Leu Glu Trp Met
        35              40              45

Gly Arg Ile Asn Pro His Asn Gly Gly Thr Asp Tyr Asn Gln Lys Phe
    50              55              60

Lys Asp Arg Val Thr Met Thr Arg Asp Thr Ser Ile Ser Thr Ala Tyr
65              70              75              80

Met Glu Leu Ser Arg Leu Arg Ser Asp Asp Thr Val Val Tyr Tyr Cys
                85              90              95

Ala Arg Gly Tyr Tyr Tyr Tyr Ser Leu Asp Tyr Trp Gly Gln Gly Thr
            100             105             110
```

Leu Val Thr Val Ser Ser
  115

<210> SEQ ID NO 14
<211> LENGTH: 118
<212> TYPE: PRT
<213> ORGANISM: Artificial Sequence
<220> FEATURE:
<223> OTHER INFORMATION: Synthetic peptide

<400> SEQUENCE: 14

Gln Val Gln Leu Val Gln Ser Gly Ala Glu Val Lys Lys Pro Gly Ala
1     5        10        15

Ser Met Lys Val Ser Cys Lys Ala Ser Gly Tyr Ser Phe Thr Gly Tyr
      20       25        30

Thr Met Asn Trp Val Arg Gln Ala Pro Gly Glu Asn Leu Glu Trp Met
     35       40       45

Gly Arg Ile Asn Pro His Asn Gly Gly Thr Asp Tyr Asn Gln Lys Phe
  50      55       60

Lys Asp Arg Val Pro Met Thr Arg Asp Thr Ser Ile Asn Thr Ala Tyr
65      70       75       80

Met Glu Leu Ser Arg Leu Arg Ser Gly Asp Ser Val Val Tyr Tyr Cys
      85      90       95

Ala Arg Gly Tyr Tyr Tyr Tyr Ser Leu Asp Tyr Trp Gly Gln Gly Thr
     100      105      110

Ser Val Thr Val Ser Ser
  115

<210> SEQ ID NO 15
<211> LENGTH: 118
<212> TYPE: PRT
<213> ORGANISM: Artificial Sequence
<220> FEATURE:
<223> OTHER INFORMATION: Synthetic peptide

<400> SEQUENCE: 15

Gln Val Gln Leu Val Gln Ser Gly Ala Glu Val Lys Lys Pro Gly Ser
1     5        10        15

Ser Met Lys Val Ser Cys Lys Ala Ser Gly Tyr Ser Phe Thr Gly Tyr
      20       25        30

Thr Met Asn Trp Val Arg Gln Ala Pro Gly Glu Asn Leu Glu Trp Met
     35       40       45

Gly Arg Ile Asn Pro His Asn Gly Gly Thr Asp Tyr Asn Gln Lys Phe
  50      55       60

Lys Asp Arg Val Pro Ile Thr Ala Asp Lys Ser Thr Asn Thr Ala Tyr
65      70       75       80

Met Glu Leu Ser Ser Leu Arg Ser Gly Asp Ser Ala Val Tyr Tyr Cys
      85      90       95

Ala Arg Gly Tyr Tyr Tyr Tyr Ser Leu Asp Tyr Trp Gly Gln Gly Thr
     100      105      110

Leu Val Thr Val Ser Ser
  115

<210> SEQ ID NO 16
<211> LENGTH: 118
<212> TYPE: PRT
<213> ORGANISM: Artificial Sequence
<220> FEATURE:
<223> OTHER INFORMATION: Synthetic peptide -continued

```
<400> SEQUENCE: 16

Gln Val Gln Leu Val Glu Ser Gly Gly Gly Val Val Gln Pro Gly Arg
1               5                   10                  15

Ser Met Arg Leu Ser Cys Ala Ala Ser Gly Tyr Ser Phe Thr Gly Tyr
                20                  25                  30

Thr Met Asn Trp Val Arg Gln Ala Pro Gly Glu Asn Leu Glu Trp Val
            35                  40                  45

Ala Arg Ile Asn Pro His Asn Gly Gly Thr Asp Tyr Asn Gln Lys Phe
        50                  55                  60

Lys Asp Arg Phe Pro Ile Ser Arg Asp Asn Ser Lys Asn Thr Leu Tyr
65                  70                  75                  80

Leu Gln Met Asn Ser Leu Arg Ala Gly Asp Ser Ala Val Tyr Tyr Cys
                85                  90                  95

Ala Arg Gly Tyr Tyr Tyr Tyr Ser Leu Asp Tyr Trp Gly Gln Gly Thr
            100                 105                 110

Thr Val Thr Val Ser Ser
        115

<210> SEQ ID NO 17
<211> LENGTH: 118
<212> TYPE: PRT
<213> ORGANISM: Artificial Sequence
<220> FEATURE:
<223> OTHER INFORMATION: Synthetic peptide

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Arg Ile Asn Pro His Asn Gly Gly Thr Asp Tyr Ala Gln Lys Phe
        50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Tyr Tyr Ser Leu Asp Tyr Trp Gly Gln Gly Thr
            100                 105                 110

Leu Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Synthetic peptide

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
                20                  25                  30

Thr Met Asn Trp Val Arg Gln Met Pro Gly Lys Gly Leu Glu Trp Met
            35                  40                  45
```

```
Gly Arg Ile Asn Pro His Asn Gly Gly Thr Asp Tyr Asn Gln Lys Phe
        50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Gly Tyr Tyr Tyr Tyr Ser Leu Asp Tyr Trp Gly Gln Gly Thr
                100                 105                 110

Leu Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Synthetic peptide

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Arg Ile Asn Pro His Asn Gly Gly Thr Asp Tyr Asn Gln Lys Phe
        50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Tyr Tyr Tyr Tyr Ser Leu Asp Tyr Trp Gly Gln Gly Thr
                100                 105                 110

Leu Val Thr Val Ser Ser
        115

<210> SEQ ID NO 20
<211> LENGTH: 118
<212> TYPE: PRT
<213> ORGANISM: Artificial Sequence
<220> FEATURE:
<223> OTHER INFORMATION: Synthetic peptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Asn Gly Leu Glu Trp Val
            35                  40                  45

Ala Arg Ile Asn Pro His Asn Gly Gly Thr Asp Tyr Asn Gln Lys Phe
        50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Tyr Tyr Tyr Tyr Ser Leu Asp Tyr Trp Gly Gln Gly Thr
                100                 105                 110
```

Thr Val Thr Val Ser Ser
        115

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Ser Ala Ser Ser Ser Ile Arg Tyr Ile His
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Asp Thr Ser Asn Leu Ala Ser Gly Val Pro Ala
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

His Gln Arg Asn Ser Tyr Pro Trp
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Gly Tyr Ser Phe Thr Gly Tyr Thr Met Asn
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide

<400> SEQUENCE: 25

Arg Ile Asn Pro His Asn Gly Gly Thr Asp Tyr Asn Gln Lys Phe Lys
1               5                   10                  15

Asp

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 26

Gly Tyr Tyr Tyr Tyr Ser Leu Asp Tyr
1               5

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Trp Tyr Gln Gln Lys Pro Gly Gln Ala Pro Arg Leu Leu Ile Tyr
1               5                   10                  15

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Arg Phe Ser Gly Ser Gly Ser Gly Thr Asp Phe Thr Leu Thr Ile Ser
1               5                   10                  15

Ser Leu Glu Pro Glu Asp Phe Ala Val Tyr Tyr Cys
            20                  25

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

<400> SEQUENCE: 30

Thr Phe Gly Gln Gly Thr Lys Val Glu Ile Lys
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Synthetic peptide

<400> SEQUENCE: 31

Glu Ile Val Leu Thr Gln Ser Pro Ala Thr Leu Ser Val Ser Pro Gly
1               5                   10                  15

Glu Arg Ala Thr Leu Ser Cys
            20
```

-continued

```
<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Trp Tyr Gln Gln Arg Pro Gly Gln Ala Pro Arg Leu Leu Ile Tyr
1               5                   10                  15

<210> SEQ ID NO 33
<211> LENGTH: 28
<212> TYPE: PRT
<213> ORGANISM: Artificial Sequence
<220> FEATURE:
<223> OTHER INFORMATION: Synthetic peptide

<400> SEQUENCE: 33

Arg Phe Ser Gly Ser Gly Ser Gly Thr Asp Phe Thr Leu Thr Ile Ser
1               5                   10                  15

Ser Leu Glu Pro Glu Asp Phe Ala Val Tyr Tyr Cys
            20                  25

<210> SEQ ID NO 34
<211> LENGTH: 11
<212> TYPE: PRT
<213> ORGANISM: Artificial Sequence
<220> FEATURE:
<223> OTHER INFORMATION: Synthetic peptide

<400> SEQUENCE: 34

Thr Phe Gly Gln Gly Thr Lys Val Glu Ile Lys
1               5                   10

<210> SEQ ID NO 35
<211> LENGTH: 23
<212> TYPE: PRT
<213> ORGANISM: Artificial Sequence
<220> FEATURE:
<223> OTHER INFORMATION: Synthetic peptide

<400> SEQUENCE: 35

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide

<400> SEQUENCE: 36

Trp Tyr Gln Gln Arg Pro Asp Gln Ser Pro Lys Leu Leu Ile Tyr
1               5                   10                  15

<210> SEQ ID NO 37
<211> LENGTH: 28
<212> TYPE: PRT
<213> ORGANISM: Artificial Sequence
<220> FEATURE:
<223> OTHER INFORMATION: Synthetic peptide
```

-continued

```
<400> SEQUENCE: 37

Arg Phe Ser Gly Ser Gly Ser Gly Thr Asp Phe Thr Leu Thr Ile Asn
1               5                   10                  15

Ser Leu Glu Ala Glu Asp Ala Ala Thr Tyr Tyr Cys
            20                  25

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide

<400> SEQUENCE: 38

Thr Phe Gly Gln Gly Thr Lys Val Glu Ile Lys
1               5                   10

<210> SEQ ID NO 39
<211> LENGTH: 23
<212> TYPE: PRT
<213> ORGANISM: Artificial Sequence
<220> FEATURE:
<223> OTHER INFORMATION: Synthetic peptide

<400> SEQUENCE: 39

Glu Ile Val Leu Thr Gln Ser Pro Ala Thr Leu Ser Val Ser Pro Gly
1               5                   10                  15

Glu Arg Ala Thr Leu Ser Cys
            20

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Trp Tyr Gln Gln Arg Pro Gly Gln Ala Pro Arg Leu Leu Ile Tyr
1               5                   10                  15

<210> SEQ ID NO 41
<211> LENGTH: 28
<212> TYPE: PRT
<213> ORGANISM: Artificial Sequence
<220> FEATURE:
<223> OTHER INFORMATION: Synthetic peptide

<400> SEQUENCE: 41

Arg Phe Ser Gly Ser Gly Ser Gly Thr Asp Phe Thr Leu Thr Ile Ser
1               5                   10                  15

Ser Leu Glu Pro Glu Asp Phe Ala Val Tyr Tyr Cys
            20                  25

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide

<400> SEQUENCE: 42

Thr Phe Gly Pro Gly Thr Lys Val Asp Ile Lys
1               5                   10
```

```
<210> SEQ ID NO 43
<211> LENGTH: 23
<212> TYPE: PRT
<213> ORGANISM: Artificial Sequence
<220> FEATURE:
<223> OTHER INFORMATION: Synthetic peptide

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44

Trp Tyr Gln Gln Lys Pro Gly Gln Ala Pro Arg Arg Trp Ile Tyr
1               5                   10                  15

<210> SEQ ID NO 45
<211> LENGTH: 28
<212> TYPE: PRT
<213> ORGANISM: Artificial Sequence
<220> FEATURE:
<223> OTHER INFORMATION: Synthetic peptide

<400> SEQUENCE: 45

Arg Phe Ser Gly Ser Gly Ser Gly Thr Ser Tyr Ser Leu Thr Ile Ser
1               5                   10                  15

Ser Leu Glu Pro Glu Asp Phe Ala Val Tyr Tyr Cys
            20                  25

<210> SEQ ID NO 46
<211> LENGTH: 11
<212> TYPE: PRT
<213> ORGANISM: Artificial Sequence
<220> FEATURE:
<223> OTHER INFORMATION: Synthetic peptide

<400> SEQUENCE: 46

Thr Phe Gly Gln Gly Thr Lys Val Glu Ile Lys
1               5                   10

<210> SEQ ID NO 47
<211> LENGTH: 23
<212> TYPE: PRT
<213> ORGANISM: Artificial Sequence
<220> FEATURE:
<223> OTHER INFORMATION: Synthetic peptide

<400> SEQUENCE: 47

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 48
<211> LENGTH: 15
<212> TYPE: PRT
<213> ORGANISM: Artificial Sequence
```

<220> FEATURE:
<223> OTHER INFORMATION: Synthetic peptide

<400> SEQUENCE: 48

Trp Tyr Gln Gln Arg Pro Asp Gln Ser Pro Lys Arg Trp Ile Tyr
1               5                   10                  15

<210> SEQ ID NO 49
<211> LENGTH: 28
<212> TYPE: PRT
<213> ORGANISM: Artificial Sequence
<220> FEATURE:
<223> OTHER INFORMATION: Synthetic peptide

<400> SEQUENCE: 49

Arg Phe Ser Gly Ser Gly Ser Gly Thr Ser Tyr Ser Leu Thr Ile Asn
1               5                   10                  15

Ser Leu Glu Ala Glu Asp Ala Ala Thr Tyr Tyr Cys
            20                  25

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Thr Phe Gly Gln Gly Thr Lys Val Glu Ile Lys
1               5                   10

<210> SEQ ID NO 51
<211> LENGTH: 23
<212> TYPE: PRT
<213> ORGANISM: Artificial Sequence
<220> FEATURE:
<223> OTHER INFORMATION: Synthetic peptide

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52

Trp Tyr Gln Gln Lys Pro Gly Gln Ala Pro Arg Arg Trp Ile Tyr
1               5                   10                  15

<210> SEQ ID NO 53
<211> LENGTH: 28
<212> TYPE: PRT
<213> ORGANISM: Artificial Sequence
<220> FEATURE:
<223> OTHER INFORMATION: Synthetic peptide

<400> SEQUENCE: 53

Arg Phe Ser Gly Ser Gly Ser Gly Thr Ser Tyr Ser Leu Thr Ile Ser
1               5                   10                  15

Ser Leu Glu Pro Glu Asp Phe Ala Val Tyr Tyr Cys
            20                          25

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide

<400> SEQUENCE: 54

Thr Phe Gly Gln Gly Thr Lys Val Glu Ile Lys
1               5                   10

<210> SEQ ID NO 55
<211> LENGTH: 23
<212> TYPE: PRT
<213> ORGANISM: Artificial Sequence
<220> FEATURE:
<223> OTHER INFORMATION: Synthetic peptide

<400> SEQUENCE: 55

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide

<400> SEQUENCE: 56

Trp Tyr Gln Gln Arg Pro Asp Gln Ser Pro Lys Arg Trp Ile Tyr
1               5                   10                  15

<210> SEQ ID NO 57
<211> LENGTH: 28
<212> TYPE: PRT
<213> ORGANISM: Artificial Sequence
<220> FEATURE:
<223> OTHER INFORMATION: Synthetic peptide

<400> SEQUENCE: 57

Arg Phe Ser Gly Ser Gly Ser Gly Thr Ser Tyr Ser Leu Thr Ile Asn
1               5                   10                  15

Ser Leu Glu Ala Glu Asp Ala Ala Thr Tyr Tyr Cys
            20                          25

<210> SEQ ID NO 58
<211> LENGTH: 11
<212> TYPE: PRT
<213> ORGANISM: Artificial Sequence
<220> FEATURE:
<223> OTHER INFORMATION: Synthetic peptide

<400> SEQUENCE: 58

Thr Phe Gly Gln Gly Thr Lys Val Glu Ile Lys
1               5                   10

<210> SEQ ID NO 59
<211> LENGTH: 23
<212> TYPE: PRT
<213> ORGANISM: Artificial Sequence -continued
<220> FEATURE:
<223> OTHER INFORMATION: Synthetic peptide

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide

<400> SEQUENCE: 60

Trp Tyr Gln Gln Lys Pro Gly Gln Ala Pro Arg Arg Trp Ile Tyr
1               5                   10                  15

<210> SEQ ID NO 61
<211> LENGTH: 28
<212> TYPE: PRT
<213> ORGANISM: Artificial Sequence
<220> FEATURE:
<223> OTHER INFORMATION: Synthetic peptide

<400> SEQUENCE: 61

Arg Phe Ser Gly Ser Gly Ser Gly Thr Asp Phe Thr Leu Thr Ile Ser
1               5                   10                  15

Ser Leu Glu Pro Glu Asp Phe Ala Val Tyr Tyr Cys
            20                  25

<210> SEQ ID NO 62
<211> LENGTH: 11
<212> TYPE: PRT
<213> ORGANISM: Artificial Sequence
<220> FEATURE:
<223> OTHER INFORMATION: Synthetic peptide

<400> SEQUENCE: 62

Thr Phe Gly Gln Gly Thr Lys Val Glu Ile Lys
1               5                   10

<210> SEQ ID NO 63
<211> LENGTH: 23
<212> TYPE: PRT
<213> ORGANISM: Artificial Sequence
<220> FEATURE:
<223> OTHER INFORMATION: Synthetic peptide

<400> SEQUENCE: 63

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide

<400> SEQUENCE: 64

-continued

```
Trp Tyr Gln Gln Arg Pro Asp Gln Ser Pro Lys Arg Trp Ile Tyr
1               5                   10                  15

<210> SEQ ID NO 65
<211> LENGTH: 28
<212> TYPE: PRT
<213> ORGANISM: Artificial Sequence
<220> FEATURE:
<223> OTHER INFORMATION: Synthetic peptide

<400> SEQUENCE: 65

Arg Phe Ser Gly Ser Gly Ser Gly Thr Asp Phe Thr Leu Thr Ile Asn
1               5                   10                  15

Ser Leu Glu Ala Glu Asp Ala Ala Thr Tyr Tyr Cys
            20                  25

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide

<400> SEQUENCE: 66

Thr Phe Gly Gln Gly Thr Lys Val Glu Ile Lys
1               5                   10

<210> SEQ ID NO 67
<211> LENGTH: 23
<212> TYPE: PRT
<213> ORGANISM: Artificial Sequence
<220> FEATURE:
<223> OTHER INFORMATION: Synthetic peptide

<400> SEQUENCE: 67

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide

<400> SEQUENCE: 68

Trp Tyr Gln Gln Lys Pro Gly Gln Ala Pro Arg Leu Leu Ile Tyr
1               5                   10                  15

<210> SEQ ID NO 69
<211> LENGTH: 28
<212> TYPE: PRT
<213> ORGANISM: Artificial Sequence
<220> FEATURE:
<223> OTHER INFORMATION: Synthetic peptide

<400> SEQUENCE: 69

Arg Phe Ser Gly Ser Gly Ser Gly Thr Ser Tyr Ser Leu Thr Ile Ser
1               5                   10                  15

Ser Leu Glu Pro Glu Asp Phe Ala Val Tyr Tyr Cys
            20                  25

<210> SEQ ID NO 70
```

-continued

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 70

Thr Phe Gly Gln Gly Thr Lys Val Glu Ile Lys
1               5                   10

<210> SEQ ID NO 71
<211> LENGTH: 23
<212> TYPE: PRT
<213> ORGANISM: Artificial Sequence
<220> FEATURE:
<223> OTHER INFORMATION: Synthetic peptide

<400> SEQUENCE: 71

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide

<400> SEQUENCE: 72

Trp Tyr Gln Gln Arg Pro Asp Gln Ser Pro Lys Leu Leu Ile Tyr
1               5                   10                  15

<210> SEQ ID NO 73
<211> LENGTH: 28
<212> TYPE: PRT
<213> ORGANISM: Artificial Sequence
<220> FEATURE:
<223> OTHER INFORMATION: Synthetic peptide

<400> SEQUENCE: 73

Arg Phe Ser Gly Ser Gly Ser Gly Thr Ser Tyr Ser Leu Thr Ile Asn
1               5                   10                  15

Ser Leu Glu Ala Glu Asp Ala Ala Thr Tyr Tyr Cys
            20                  25

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide

<400> SEQUENCE: 74

Thr Phe Gly Gln Gly Thr Lys Val Glu Ile Lys
1               5                   10

<210> SEQ ID NO 75
<211> LENGTH: 25
<212> TYPE: PRT
<213> ORGANISM: Artificial Sequence
<220> FEATURE:
<223> OTHER INFORMATION: Synthetic peptide

<400> SEQUENCE: 75
```

```
Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 76
<211> LENGTH: 14
<212> TYPE: PRT
<213> ORGANISM: Artificial Sequence
<220> FEATURE:
<223> OTHER INFORMATION: Synthetic peptide

<400> SEQUENCE: 76

Trp Val Arg Gln Ala Pro Gly Gln Gly Leu Glu Trp Met Gly
1               5                   10

<210> SEQ ID NO 77
<211> LENGTH: 32
<212> TYPE: PRT
<213> ORGANISM: Artificial Sequence
<220> FEATURE:
<223> OTHER INFORMATION: Synthetic peptide

<400> SEQUENCE: 77

Arg Val Thr Met Thr Arg Asp Thr Ser Ile Ser Thr Ala Tyr Met Glu
1               5                   10                  15

Leu Ser Arg Leu Arg Ser Asp Asp Thr Val Val Tyr Tyr Cys Ala Arg
            20                  25                  30

<210> SEQ ID NO 78
<211> LENGTH: 11
<212> TYPE: PRT
<213> ORGANISM: Artificial Sequence
<220> FEATURE:
<223> OTHER INFORMATION: Synthetic peptide

<400> SEQUENCE: 78

Trp Gly Gln Gly Thr Leu Val Thr Val Ser Ser
1               5                   10

<210> SEQ ID NO 79
<211> LENGTH: 25
<212> TYPE: PRT
<213> ORGANISM: Artificial Sequence
<220> FEATURE:
<223> OTHER INFORMATION: Synthetic peptide

<400> SEQUENCE: 79

Gln Val Gln Leu Val Gln Ser Gly Ala Glu Val Lys Lys Pro Gly Ala
1               5                   10                  15

Ser Met Lys Val Ser Cys Lys Ala Ser
            20                  25

<210> SEQ ID NO 80
<211> LENGTH: 14
<212> TYPE: PRT
<213> ORGANISM: Artificial Sequence
<220> FEATURE:
<223> OTHER INFORMATION: Synthetic peptide

<400> SEQUENCE: 80

Trp Val Arg Gln Ala Pro Gly Glu Asn Leu Glu Trp Met Gly
1               5                   10

<210> SEQ ID NO 81
```

-continued

```
<211> LENGTH: 32
<212> TYPE: PRT
<213> ORGANISM: Artificial Sequence
<220> FEATURE:
<223> OTHER INFORMATION: Synthetic peptide

<400> SEQUENCE: 81

Arg Val Pro Met Thr Arg Asp Thr Ser Ile Asn Thr Ala Tyr Met Glu
1               5                   10                  15

Leu Ser Arg Leu Arg Ser Gly Asp Ser Val Val Tyr Tyr Cys Ala Arg
            20                  25                  30

<210> SEQ ID NO 82
<211> LENGTH: 11
<212> TYPE: PRT
<213> ORGANISM: Artificial Sequence
<220> FEATURE:
<223> OTHER INFORMATION: Synthetic peptide

<400> SEQUENCE: 82

Trp Gly Gln Gly Thr Ser Val Thr Val Ser Ser
1               5                   10

<210> SEQ ID NO 83
<211> LENGTH: 25
<212> TYPE: PRT
<213> ORGANISM: Artificial Sequence
<220> FEATURE:
<223> OTHER INFORMATION: Synthetic peptide

<400> SEQUENCE: 83

Gln Val Gln Leu Val Gln Ser Gly Ala Glu Val Lys Lys Pro Gly Ser
1               5                   10                  15

Ser Met Lys Val Ser Cys Lys Ala Ser
            20                  25

<210> SEQ ID NO 84
<211> LENGTH: 14
<212> TYPE: PRT
<213> ORGANISM: Artificial Sequence
<220> FEATURE:
<223> OTHER INFORMATION: Synthetic peptide

<400> SEQUENCE: 84

Trp Val Arg Gln Ala Pro Gly Glu Asn Leu Glu Trp Met Gly
1               5                   10

<210> SEQ ID NO 85
<211> LENGTH: 32
<212> TYPE: PRT
<213> ORGANISM: Artificial Sequence
<220> FEATURE:
<223> OTHER INFORMATION: Synthetic peptide

<400> SEQUENCE: 85

Arg Val Pro Ile Thr Ala Asp Lys Ser Thr Asn Thr Ala Tyr Met Glu
1               5                   10                  15

Leu Ser Ser Leu Arg Ser Gly Asp Ser Ala Val Tyr Tyr Cys Ala Arg
            20                  25                  30

<210> SEQ ID NO 86
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 86

Trp Gly Gln Gly Thr Leu Val Thr Val Ser Ser
1               5                   10

<210> SEQ ID NO 87
<211> LENGTH: 25
<212> TYPE: PRT
<213> ORGANISM: Artificial Sequence
<220> FEATURE:
<223> OTHER INFORMATION: Synthetic peptide

<400> SEQUENCE: 87

Gln Val Gln Leu Val Glu Ser Gly Gly Gly Val Val Gln Pro Gly Arg
1               5                   10                  15

Ser Met Arg Leu Ser Cys Ala Ala Ser
            20                  25

<210> SEQ ID NO 88
<211> LENGTH: 14
<212> TYPE: PRT
<213> ORGANISM: Artificial Sequence
<220> FEATURE:
<223> OTHER INFORMATION: Synthetic peptide

<400> SEQUENCE: 88

Trp Val Arg Gln Ala Pro Gly Glu Asn Leu Glu Trp Val Ala
1               5                   10

<210> SEQ ID NO 89
<211> LENGTH: 32
<212> TYPE: PRT
<213> ORGANISM: Artificial Sequence
<220> FEATURE:
<223> OTHER INFORMATION: Synthetic peptide

<400> SEQUENCE: 89

Arg Phe Pro Ile Ser Arg Asp Asn Ser Lys Asn Thr Leu Tyr Leu Gln
1               5                   10                  15

Met Asn Ser Leu Arg Ala Gly Asp Ser Ala Val Tyr Tyr Cys Ala Arg
            20                  25                  30

<210> SEQ ID NO 90
<211> LENGTH: 11
<212> TYPE: PRT
<213> ORGANISM: Artificial Sequence
<220> FEATURE:
<223> OTHER INFORMATION: Synthetic peptide

<400> SEQUENCE: 90

Trp Gly Gln Gly Thr Thr Val Thr Val Ser Ser
1               5                   10

<210> SEQ ID NO 91
<211> LENGTH: 25
<212> TYPE: PRT
<213> ORGANISM: Artificial Sequence
<220> FEATURE:
<223> OTHER INFORMATION: Synthetic peptide

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser
            20                  25

```
<210> SEQ ID NO 92
<211> LENGTH: 14
<212> TYPE: PRT
<213> ORGANISM: Artificial Sequence
<220> FEATURE:
<223> OTHER INFORMATION: Synthetic peptide

<400> SEQUENCE: 92

Trp Val Arg Gln Ala Pro Gly Gln Gly Leu Glu Trp Met Gly
1               5                   10

<210> SEQ ID NO 93
<211> LENGTH: 32
<212> TYPE: PRT
<213> ORGANISM: Artificial Sequence
<220> FEATURE:
<223> OTHER INFORMATION: Synthetic peptide

<400> SEQUENCE: 93

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 94
<211> LENGTH: 11
<212> TYPE: PRT
<213> ORGANISM: Artificial Sequence
<220> FEATURE:
<223> OTHER INFORMATION: Synthetic peptide

<400> SEQUENCE: 94

Trp Gly Gln Gly Thr Leu Val Thr Val Ser Ser
1               5                   10

<210> SEQ ID NO 95
<211> LENGTH: 25
<212> TYPE: PRT
<213> ORGANISM: Artificial Sequence
<220> FEATURE:
<223> OTHER INFORMATION: Synthetic peptide

<400> SEQUENCE: 95

Glu Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 96
<211> LENGTH: 14
<212> TYPE: PRT
<213> ORGANISM: Artificial Sequence
<220> FEATURE:
<223> OTHER INFORMATION: Synthetic peptide

<400> SEQUENCE: 96

Trp Val Arg Gln Met Pro Gly Lys Gly Leu Glu Trp Met Gly
1               5                   10

<210> SEQ ID NO 97
<211> LENGTH: 32
<212> TYPE: PRT
<213> ORGANISM: Artificial Sequence
<220> FEATURE:
<223> OTHER INFORMATION: Synthetic peptide
```

<400> SEQUENCE: 97

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
                20                  25                  30

<210> SEQ ID NO 98
<211> LENGTH: 11
<212> TYPE: PRT
<213> ORGANISM: Artificial Sequence
<220> FEATURE:
<223> OTHER INFORMATION: Synthetic peptide

<400> SEQUENCE: 98

Trp Gly Gln Gly Thr Leu Val Thr Val Ser Ser
1               5                   10

<210> SEQ ID NO 99
<211> LENGTH: 25
<212> TYPE: PRT
<213> ORGANISM: Artificial Sequence
<220> FEATURE:
<223> OTHER INFORMATION: Synthetic peptide

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser
                20                  25

<210> SEQ ID NO 100
<211> LENGTH: 14
<212> TYPE: PRT
<213> ORGANISM: Artificial Sequence
<220> FEATURE:
<223> OTHER INFORMATION: Synthetic peptide

<400> SEQUENCE: 100

Trp Val Arg Gln Ala Pro Gly Gln Gly Leu Glu Trp Met Gly
1               5                   10

<210> SEQ ID NO 101
<211> LENGTH: 32
<212> TYPE: PRT
<213> ORGANISM: Artificial Sequence
<220> FEATURE:
<223> OTHER INFORMATION: Synthetic peptide

<400> SEQUENCE: 101

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 102
<211> LENGTH: 11
<212> TYPE: PRT
<213> ORGANISM: Artificial Sequence
<220> FEATURE:
<223> OTHER INFORMATION: Synthetic peptide

<400> SEQUENCE: 102

Trp Gly Gln Gly Thr Leu Val Thr Val Ser Ser
1               5                   10

<210> SEQ ID NO 103
<211> LENGTH: 25
<212> TYPE: PRT
<213> ORGANISM: Artificial Sequence
<220> FEATURE:
<223> OTHER INFORMATION: Synthetic peptide

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 104
<211> LENGTH: 14
<212> TYPE: PRT
<213> ORGANISM: Artificial Sequence
<220> FEATURE:
<223> OTHER INFORMATION: Synthetic peptide

<400> SEQUENCE: 104

Trp Val Arg Gln Ala Pro Gly Asn Gly Leu Glu Trp Val Ala
1               5                   10

<210> SEQ ID NO 105
<211> LENGTH: 32
<212> TYPE: PRT
<213> ORGANISM: Artificial Sequence
<220> FEATURE:
<223> OTHER INFORMATION: Synthetic peptide

<400> SEQUENCE: 105

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 106
<211> LENGTH: 11
<212> TYPE: PRT
<213> ORGANISM: Artificial Sequence
<220> FEATURE:
<223> OTHER INFORMATION: Synthetic peptide

<400> SEQUENCE: 106

Trp Gly Gln Gly Thr Thr Val Thr Val Ser Ser
1               5                   10

<210> SEQ ID NO 107
<211> LENGTH: 106
<212> TYPE: PRT
<213> ORGANISM: Artificial Sequence
<220> FEATURE:
<223> OTHER INFORMATION: Synthetic peptide

<400> SEQUENCE: 107

Gln Ile Val Leu Thr Gln Ser Pro Ala Ile Met Ser Val Ser Pro Gly
1               5                   10                  15

Glu Lys Val Thr Met Thr Cys Ser Ala Ser Ser Ser Ile Arg Tyr Ile
            20                  25                  30

His Trp Tyr Gln Gln Arg Pro Gly Thr Ser Pro Lys Arg Trp Ile Tyr
        35                  40                  45

Asp Thr Ser Asn Leu Ala Ser Gly Val Pro Ala Arg Phe Ser Gly Ser

-continued

```
                50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Asn Ser Tyr Pro Trp Thr
                85                  90                  95

Phe Gly Gly Gly Thr Arg Leu Glu Ile Arg
            100                 105

<210> SEQ ID NO 108
<211> LENGTH: 118
<212> TYPE: PRT
<213> ORGANISM: Artificial Sequence
<220> FEATURE:
<223> OTHER INFORMATION: Synthetic peptide

<400> SEQUENCE: 108

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Glu Asn Leu Glu Trp Ile
            35                  40                  45

Gly Arg Ile Asn Pro His Asn Gly Gly Thr Asp Tyr Asn Gln Lys Phe
        50                  55                  60

Lys Asp Lys Ala Pro Leu Thr Val Asp Lys Ser Ser Asn Thr Ala Tyr
65                  70                  75                  80

Met Glu Leu Leu Ser Leu Thr Ser Gly Asp Ser Ala Val Tyr Tyr Cys
                85                  90                  95

Ala Arg Gly Tyr Tyr Tyr Tyr Ser Leu Asp Tyr Trp Gly Gln Gly Thr
                100                 105                 110

Ser Val Thr Val Ser Ser
        115

<210> SEQ ID NO 109
<211> LENGTH: 8
<212> TYPE: PRT
<213> ORGANISM: Artificial Sequence
<220> FEATURE:
<223> OTHER INFORMATION: Synthetic peptide

<400> SEQUENCE: 109

Gln Gln Arg Asn Ser Tyr Pro Trp
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic peptide

<400> SEQUENCE: 110

Arg Ile Asn Pro His Asn Gly Gly Thr Asp Tyr Ala Gln Lys Phe Gln
1               5                   10                  15

Asp
```